(12) United States Patent
Turner et al.

(10) Patent No.: US 10,023,878 B2
(45) Date of Patent: Jul. 17, 2018

(54) METHOD FOR THE ALTERATION OF PLANTS USING CLE POLYPEPTIDES/PEPTIDES

(71) Applicant: Plant Bioscience Limited, Norwich, Norfolk (GB)

(72) Inventors: Simon Turner, Manchester (GB); Peter Etchells, Manchester (GB)

(73) Assignee: STORA ENSO OYJ, Helsinki (FI)

(*) Notice: Subject to any disclaimer, the term of this patent is extended or adjusted under 35 U.S.C. 154(b) by 269 days.

(21) Appl. No.: 14/253,428

(22) Filed: Apr. 15, 2014

(65) Prior Publication Data

US 2014/0345001 A1 Nov. 20, 2014

Related U.S. Application Data

(63) Continuation of application No. 13/062,916, filed as application No. PCT/GB2009/051153 on Sep. 9, 2009, now abandoned.

(30) Foreign Application Priority Data

Sep. 9, 2008 (GB) .................................. 0816461.8

(51) Int. Cl.
| | |
|---|---|
| C12N 15/82 | (2006.01) |
| A01N 37/46 | (2006.01) |
| C07K 14/415 | (2006.01) |
| A01H 5/00 | (2018.01) |

(52) U.S. Cl.
CPC ........... *C12N 15/8291* (2013.01); *A01H 5/00* (2013.01); *A01N 37/46* (2013.01); *C07K 14/415* (2013.01); *C12N 15/8218* (2013.01); *C12N 15/8261* (2013.01); *Y02A 40/146* (2018.01)

(58) Field of Classification Search
None
See application file for complete search history.

(56) References Cited

FOREIGN PATENT DOCUMENTS

EP 1586645 A2 10/2005

OTHER PUBLICATIONS

Strabala et al., 2006, Plant Physiology 140: 1331-1344.*
Fisher et al., 2007, Current Opinion in Plant Biology 17: 1061-1066.*
Meng et al., 2010, Molecular Plant 3: 760-772.*
Ito et al., 2006, Science 313: 842-845.*
Whitford et al., 2008, Proceedings of the National Academy of Sciences USA 105: 18625-18630.*
Keskin et al., 2004, Protein Science 13: 1043-1055.*
Thornton et al., 2000, Nature Structural Biology, structural genomic supplement, Nov. 2000: 991-994.*
Guo et al., 2004, Proceedings of the National Academy of Sciences USA 101: 9205-9210.*
Zeitler et al., 2013, PLoS ONE 8(8): e71687.doi:10.1371/journal.pone.0071687.*
Hirakawa et al., 2008, Proceedings of the National Academy of Sciences USA 105: 15208-15213.*
Fiers et al., CLE peptide ligands and their roles in establishing meristems, Current Opinion in Plant Biology, 2007, 10:39-43.
Fisher et al., PXY a receptor-like kinase essential for maintaining polarity during plant vascular-tissue development, Current Biology, 2007, 17:1061-1066.
Fukuda et al., Peptide signalling in vascular development, Current Opinion in Plant Biology, 2007, 10:477-482.
Hirakawa et al., Non-cell autonomous control of vascular stem cell fate by a CLE peptide/receptor system, Proceedings of the National Academy of Sciences of the United States of America, Sep. 2008, 105(39):15208-15213.
Ito et al., Dodeca-CLE peptides as suppressors of plant stem cell differentiation, Science (Washington D.C.), Aug. 2006, 313(5788):842-845.
Kinoshita et al., Gain-of-function phonotypes of chemically synthetic CLAVATA3/ESR-related (CLE) peptides in *Arabidopsis thaliana* and *Oryza sativa*, Plant and Cell Physiology, Dec. 2007 48(12):1821-1825.
Meng et al. The Roles of Different CLE Domains in *Arabidopsis* CLE Polypeptide Activity and Functional Specificity. (2010). 3(4):760-772, Molecular Plant 3: 760-772.
Miwa et al., The Receptor-like kinase SOL2 mediates CLE signaling in *Arabidopsis*, Plant and Cell Physiology, Nov. 2008, 49(11):1752-1757.
Seiburth, Plant development: PXY and polar cell division in the procambium, Current Biology, 2007, 17:R594-R596.
Strabala et al., Gain-of-function phonotypes of many CLAVATA3/ESR genes, including four new family members, correlate with tandem variations in the conserved CLAVATA3/ESR domain, Plant Physiology, 2006, 140:1331-1344.
Whitford et al., Plant CLE peptides from two distinct functional classes synergistically induce division of vascular cells, Proceedings of The National Academy of Sciences of the United States of America, Nov. 2008, 105(47):18625-18630.
UnitProtKB Accession No. Q84W98. Retrieved from the internet: <http://www.uniprot.org/uniprot/Q84W98> on May 15, 2013.

* cited by examiner

*Primary Examiner* — Amjad Abraham
*Assistant Examiner* — Bratislav Stankovic
(74) *Attorney, Agent, or Firm* — Linda B. Huber; Nixon Peabody LLP

(57) ABSTRACT

The present invention relates to altering the biomass and/or structure of a plant, in order to maximize its potential as a source of feedstock or increase its potential as a feedstock for the paper industry. CLE41 and/or CLE42 are used to manipulate growth and structure of the vascular tissue of the plant. The present invention also provides plants in which the levels of CLE41 and/or CLE42 are increased compared to those of a native plant grown under identical conditions, and parts of such plants. Also provided are methods for using such plants or plant parts in the production of plant derived products such as paper or biofuels.

5 Claims, 24 Drawing Sheets

Fig. 12

FIGURE 13A CLE41 protein sequence

MATSNDQTNTKSSHSRTLLLLFIFLSLLLFSSLTIPMTRHQSTSMVAPFKRVLLESS
VPASSTMDLRPKASTRRSRTSRRREFGNDAHEVPSGPNPISN

FIGURE 13B CLE41 DNA sequence

ATGGCAACATCAAATGACCAAACCAATACTAAATCATCACATTCTCGTACTCT
TCTCCTTCTCTTCATCTTCTTATCCCTCCTTCTCTTCAGTAGCCTTACAATCCCC
ATGACTCGTCATCAGTCCACATCTATGGTTGCTCCCTTCAAGAGGGTTCTCC
TCGAATCTTCAGTTCCAGCTTCATCAACAATGGATCTACGTCCAAAGGCTAGC
ACACGACGCAGCCGCACTTCTAGAAGGAGAGAGTTTGGAAATGATGCTCATG
AGGTTCCTAGTGGTCCAAACCCTATTTCCAACTAG

FIGURE 14A CLE42 protein sequence
MRSPHITISLVFLFFLFLIIQTHQRTIDQTHQIGSNVQHVSDMAVTSPEGKRRER
FRVRRPMTTWLKGKMIGANEHGVPSGPNPISNR FIGURE 14B CLE42 DNA sequence
ATGAGATCTCCTCACATCACCATTTCACTTGTTTTCTTGTTCTTTCTTTTTCT
AATCATCCAAACCCATCAAAGAACCATTGATCAAACTCACCAGATGGCT
CCAATGTTCAACATGTCAGTGACATGGCGGTGACTTCGCCTGAAGGGAAA
AGAAGAGAGAGGTTTAGAGTTCGGCGGCCGATGACGACATGGCTGAAGG
GAAAGATGATCGGTGCCAATGAACATGGAGTCCCAAGTGGTCCAAATCCC
ATCTCCAATAGGTAG FIGURE 15A PXY protein sequence
MKKKNISPSLVLHPLLLLLLPFFAFNSLALKFSPQLLSLLSLKTSLSGPPSAFQDWKVPVNGQND
AVWCSWSGVVCDNVTAQVISLDLSHRNLSGRIPIQIRYLSSLLYLNLSGNSLEGSFPTSIFDLTKL
TTLDISRNSFDSSFPPGISKLKFLKVFNAFSNNFEGLLPSDVSRLRFLEELNFGGSYFEGEIPAAY
GGLQRLKFIHLAGNVLGGKLPPRLGLLTELQHMEIGYNHFNGNIPSEFALLSNLKYFDVSNCSLS
GSLPQELGNLSNLETLFLFQNGFTGEIPESYSNLKSLKLLDFSSNQLSGSIPSGFSTLKNLTWLS
LISNNLSGEVPEGIGELPELTTLFLWNNNFTGVLPHKLGSNGKLETMDVSNNSFTGTIPSSLCHG
NKLYKLILFSNMFEGELPKSLTRCESLWRFRSQNNRLNGTIPIGFGSLRNLTFVDLSNNRFTDQIP
ADFATAPVLQYLNLSTNFFHRKLPENIWKAPNLQIFSASFSNLIGEIPNYVGCKSFYRIELQGNSL
NGTIPWDIGHCEKLLCLNLSQNHLNGIIPWEISTLPSIADVDLSHNLLTGTIPSDFGSSKTITTFNV
SYNQLIGPIPSGSFAHLNPSFFSSNEGLCGDLVGKPCNSDRFNAGNADIDGHHKEERPKKTAGA
IVWILAAAIGVGFFVLVAATRCFQKSYGNRVDGGGRNGGDIGPWKLTAFQRLNFTADDVVECLS
KTDNILGMGSTGTVYKAEMPNGEIAVKKLWGKNKENGKIRRRKSGVLAEVDVLGNVRHRNIVR
LLGCCTNRDCTMLLYEYMPNGSLDDLLHGGDKTMTAAAEWTALYQIAIGVAQGICYLHHDCDPV
IVHRDLKPSNILLDADFEARVADFGVAKLIQTDESMSVVAGSYGYIAPEYAYTLQVDKKSDIYSYG
VILLEITGKRSVEPEFGEGNSIVDWVRSKLKTKEDVEEVLDKSMGRSCSLIREEMKQMLRIALL
CTSRSPTDRPPMRDVLLILQEAKPKRKTVGDNVIVVGDVNDVNFEDVCSVDVGHDVKCQRIGV FIGURE 15B PXY DNA sequence without intron
ATGAAAAAGAAGAACATTTCTCCTTCTCTTGTTCTTCATCCCCTTCTCCTTCTTCTACTTCCT
TTCTTTGCTTTCAATTCCTTAGCTCTCAAGTTTTCACCTCAACTCTTGTCTCTCCTTTCCCTT
AAAACATCTCTCTCTGGCCCTCCCTCTGCCTTTCAAGACTGGAAAGTCCCCGTTAACGGTC
AAAACGACGCCGTTTGGTGTTCTTGGTCCGGTGTAGTCTGTGATAATGTAACGGCTCAAGT
CATTTCCCTCGACCTCTCTCACCGGAACCTCTCTGGTCGTATTCCTATACAGATTCGTTACT
TGTCGAGCTTACTCTACTTAAATCTCAGTGGGAATTCTTTGGAAGGTTCGTTTCCAACTTCT
ATCTTTGATCTCACCAAGCTCACTACCCTCGACATCAGCCGTAACTCGTTCGACTCGAGTT
TTCCTCCCGGAATCTCCAAGCTTAAGTTCTTAAAAGTCTTCAATGCGTTCAGCAACAACTTC
GAAGGTCTATTACCTAGTGACGTGTCTCGTCTTCGTTTCTTGGAAGAGCTTAACTTTGGTG
GAAGTTACTTTGAAGGAGAGATTCCAGCAGCTTACGGTGGTTTACAGAGATTGAAGTTTAT
TCATTTAGCTGGAAATGTCCTCGGAGGTAAACTACCTCCTAGATTAGGACTCTTAACAGAGC
TCCAACACATGGAAATCGGTTATAATCACTTCAACGGAAACATACCTTCGGAGTTTGCCTTA
CTCTCAAATCTCAAGTACTTTGACGTTTCCAATTGCAGCCTCTCTGGTTCTCTGCCTCAAG
AACTCGGGAATCTCTCAAACCTAGAGACTTTATTTCTATTCCAAAACGGTTTCACCGGTGAA
ATCCCAGAGAGTTATAGCAACTTGAAATCCCTCAAGCTTCTCGATTTTTCGAGTAATCAGCT
TTCTGGTAGTATCCCATCAGGCTTCTCGACCTTGAAGAACCTCACATGGCTAAGCTTAATCA
GCAATAACCTCTCAGGTGAAGTACCTGAAGGAATCGGTGAACTCCCTGAGCTTACTACATT
GTTTCTATGGAACAATAACTTCACCGGAGTTTTGCCACACAAGCTTGGATCAAACGGTAAA
CTTGAGACAATGGACGTCTCTAACAATTCATTCACCGGAACAATCCCTTCTTCTCTCTGCCA
TGGAAACAAGCTATACAAACTCATCCTCTTCTCCAACATGTTTGAAGGTGAGCTACCAAAG
AGCTTGACTCGTTGCGAATCTCTATGGCGGTTTCGGAGTCAAAACAATCGATTAAACGGCA
CAATTCCGATCGGATTCGGCTCTCTACGTAACCTCACTTTCGTTGATTTAAGCAACAACAGA
TTCACCGATCAAATTCCGGCGGATTTCGCCACCGCTCCTGTTCTTCAGTACTTGAATCTCT
CAACCAATTTCTTCCACAGGAAACTACCGGAAAACATATGGAAAGCTCCGAATCTACAGAT
CTTCTCAGCGAGTTTCAGCAATTTGATCGGTGAAATCCCAAATTACGTTGGATGCAAAAGC
TTCTACAGGATTGAACTACAAGGAAACTCACTCAACGGAACGATTCCATGGGACATCGGAC
ATTGCGAGAAGCTTCTCTGTTTGAATCTCAGCCAAAATCATCTCAACGGAATCATTCCATGG
GAGATTTCAACTCTTCCGTCAATCGCCGACGTAGATCTTTCTCATAATCTCTTAACCGGAAC
AATCCCTTCCGATTTCGGAAGCTCTAAGACGATCACAACCTTCAACGTTTCGTATAATCAGC
TAATCGGTCCGATTCCAAGTGGTTCTTTCGCTCATCTGAATCCGTCGTTCTTCTCCTCAAAC
GAAGGACTCTGTGGAGATCTCGTCGGAAAACCTTGCAATTCTGATAGGTTTAACGCCGGA
AATGCAGATATAGACGGTCATCATAAAGAGGAACGACCTAAGAAAACAGCCGGAGCTATTG
TTTGGATATTGGCGGCGGCGATTGGGGTTGGATTCTTCGTCCTTGTAGCCGCCACTAGATG
CTTCCAGAAAAGCTACGGAAACAGAGTCGACGGTGGTGGAAGAAACGGCGGAGATATAG
GACCGTGGAAGCTAACGGCTTTTCAGAGACTAAACTTCACGGCGGATGATGTGGTTGAGT
GTCTCTCAAAGACTGATAACATCCTCGGAATGGGATCAACAGGAACAGTGTACAAAGCAGA
GATGCCTAATGGAGAAATAATCGCCGTGAAAAAACTTTGGGGAAAAACAAAGAGAACGG
CAAAATCCGGCGGCGGAAGAGCGGCGTATTGGCGGAGGTTGATGTTCTAGGGAACGTAC
GTCACCGGAACATCGTTCGTCTCCTTGGATGTTGCACGAATCGAGATTGCACGATGCTTTT
ATACGAATACATGCCTAATGGAAGCTTAGACGATCTTCTTCACGGTGGGGATAAGACGATG
ACCGCGGCGGCGGAATGGACGGCTTTGTATCAGATCGCGATTGGAGTGGCTCAAGGGAT
CTGTTATCTCCACCATGATTGTGATCCGGTGATTGTACACCGTGACCTGAAACCTAGCAATA
TCCTCCTCGACGCCGATTTCGAGGCGCGTGTGGCGGACTTCGGCGTCGCGAAGCTTATT
CAAACCGACGAATCCATGTCCGTCGTCGCCGGTTCGTACGGTTACATTGCACCAGAATATG
CTTACACTTTACAAGTGGATAAAAGAGTGATATCTATAGCTATGGAGTGATTTTATTAGAGAT
AATCACCGGAAAAGATCGGTGGAACCGGAATTTGGAGAAGGTAACAGTATCGTGGATTG
GGTTAGATCAAAGTTGAAGACGAAAGAAGATGTAGAAGAAGTTCTAGACAAAAGCATGGGT
AGGTCGTGTAGTCTTATAAGAGAAGAGATGAAACAAATGTTGAGAATTGCGTTGTTGTGTAC
AAGCCGGAGTCCGACAGACAGACCGCCGATGAGAGATGTGTTGTTGATTCTTCAAGAGGC
AAAGCCAAAGAGGAAGACAGTAGGGGATAATGTGATCGTCGTTGGTGATGTTAATGATGTC
AATTTCGAAGATGTTTGTAGTGTTGATGTTGGTCATGATGTTAAATGTCAAAGGATTGGGGT
GTGA FIGURE 15C: PXY DNA sequence with intron
ATGAAAAAGAAGAACATTTCTCCTTCTCTTGTTCTTCATCCCCTTCTCCTTCTTCTACTTCCTT
TCTTTGCTTTCAATTCCTTAGCTCTCAAGTTTTCACCTCAACTCTTGTCTCTCCTTTCCCTTAA
AACATCTCTCTCTGGCCCTCCCTCTGCCTTTCAAGACTGGAAAGTCCCCGTTAACGGTCAA
AACGACGCCGTTTGGTGTTCTTGGTCCGGTGTAGTCTGTGATAATGTAACGGCTCAAGTCAT
TTCCCTCGACCTCTCTCACCGGAACCTCTCTGGTCGTATTCCTATACAGATTCGTTACTTGTC
GAGCTTACTCTACTTAAATCTCAGTGGGAATTCTTTGGAAGGTTCGTTTCCAACTTCTATCTT
TGATCTCACCAAGCTCACTACCCTCGACATCAGCCGTAACTCGTTCGACTCGAGTTTTCCTC
CCGGAATCTCCAAGCTTAAGTTCTTAAAAGTCTTCAATGCGTTCAGCAACAACTTCGAAGGT
CTATTACCTAGTGACGTGTCTCGTCTTCGTTTCTTGGAAGAGCTTAACTTTGGTGGAAGTTA
CTTTGAAGGAGAGATTCCAGCAGCTTACGGTGGTTACAGAGATTGAAGTTTATTCATTTAGC
TGGAAATGTCCTCGGAGGTAAACTACCTCCTAGATTAGGACTCTTAACAGAGCTCCAACACA
TGGAAATCGGTTATAATCACTTCAACGGAAACATACCTTCGGAGTTTGCCTTACTCTCAAATC
TCAAGTACTTTGACGTTTCCAATTGCAGCCTCTCTGGTTCTCTGCCTCAAGAACTCGGGAAT
CTCTCAAACCTAGAGACTTTATTTCTATTCCAAAACGGTTTCACCGGTGAAATCCCAGAGAG
TTATAGCAACTTGAAATCCCTCAAGCTTCTCGATTTTTCGAGTAATCAGCTTTCTGGTAGTATC
CCATCAGGCTTCTCGACCTTGAAGAACCTCACATGGCTAAGCTTAATCAGCAATAACCTCTC
AGGTGAAGTACCTGAAGGAATCGGTGAACTCCCTGAGCTTACTACATTGTTTCTATGGAACA
ATAACTTCACCGGAGTTTTGCCACACAAGCTTGGATCAAACGGTAAACTTGAGACAATGGAC
GTCTCTAACAATTCATTCACCGGAACAATCCCTTCTTCTCTGCCATGGAAACAAGCTATAC
AAACTCATCCTCTTCTCCAACATGTTTGAAGGTGAGCTACCAAAGAGCTTGACTCGTTGCGA
ATCTCTATGGCGGTTTCGGAGTCAAAACAATCGATTAAACGGCACAATTCCGATCGGATTCG
GCTCTCTACGTAACCTCACTTTCGTTGATTTAAGCAACAACAGATTCACCGATCAAATTCCGG
CGGATTTCGCCACCGCTCCTGTTCTTCAGTACTTGAATCTCTCAACCAATTTCTTCCACAGG
AAACTACCGGAAAACATATGGAAAGCTCCGAATCTACAGATCTTCTCAGCGAGTTTCAGCAA
TTTGATCGGTGAAATCCCAAATTACGTTGGATGCAAAAGCTTCTACAGGATTGAACTACAAG
GAAACTCACTCAACGGAACGATTCCATGGGACATCGGACATTGCGAGAAGCTTCTCTGTTT
GAATCTCAGCCAAAATCATCTCAACGGAATCATTCCATGGGAGATTTCAACTCTTCCGTCAAT
CGCCGACGTAGATCTTTCTCATAATCTCTTAACCGGAACAATCCCTTCCGATTCGGAAGCT
CTAAGACGATCACAACCTTCAACGTTTCGTATAATCAGCTAATCGGTCGTCGTTGGATTCCAAGTGGTT
CTTTCGCTCATCTGAATCCGTCGTTCTTCTCCTCAAACGAAGGACTCTGTGGAGATCTCGTC
GGAAAACCTTGCAATTCTGATAGGTTTAACGCCGGAAATGCAGATATAGACGGTCATCATAAA
GAGGAACGACCTAAGAAAACGCGGAGCTATTGTTTGGATATTGGCGGCGGCGATTGGG
GTTGGATTCTTCGTCCTTGTAGCCGCCACTAGATGCTTCCAGAAAAGCTACGGAAACAGAG
TCGACGGTGGTGGAAGAAACGGCGGAGATATAGGACCGTGGAAGCTAACGGCTTTTCAGA
GACTAAACTTCACGGCGGATGATGTGGTTGAGTGTCTCTCAAAGACTGATAACATCCTCGGA
ATGGGATCAACAGGAACAGTGTACAAAGCAGAGATGCCTAATGGAGAAATAATCGCCGTGA
AAAAACTTTGGGGAAAAAACAAAGAGAACGGCAAAATCCGGCGGCGGAAGAGCGGCGTAT
TGGCGGAGGTTGATGTTCTAGGGAACGTACGTCACCGGAACATCGTTCGTCTCCTTGGATG
TTGCACGAATCGAGATTGCACGATGCTTTTATACGAATACATGCCTAATGGAAGCTTAGACGA
TCTTCTTCACGGTGGGGATAAGACGATGACCGCGGCGGCGGAATGGACGGCTTTGTATCA
GATCGCGATTGGAGTGGCTCAAGGGATCTGTTATCTCCACCATGATTGTGATCCGGTGATTG
TACACCGTGACCTGAAACCTAGCAATATCCTCCTCGACGCCGATTTCGAGGCGCGTGTGGC
GGACTTCGGCGTCGCGAAGCTTATTCAAACCGACGAATCCATGTCCGTCGTCGCCGGTTC
GTACGGTTACATTGCACCAGgtacccttaactttttttgattattcttttacttttcccaaatttaaattttgtactttttgtccctttgttt
ttattattcgaatttttgtccgtttgttaaacatctttttgttgggatgacaacatctgacaaatatgactaaaatttttaattttgtttgtttttggttaca
gAATATGCTTACACTTTACAAGTGGATAAAAAGAGTGATATCTATAGCTATGGAGTGATTTTATT
AGAGATAATCACCGGAAAAAGATCGGTGGAACCGGAATTTGGAGAAGGTAACAGTATCGTG
GATTGGGTTAGATCAAAGTTGAAGACGAAAGAAGATGTAGAAGAAGTTCTAGACAAAAGCAT
GGGTAGGTCGTGTAGTCTTATAAGAGAAGAGATGAAACAAATGTTGAGAATTGCGTTGTTGT
GTACAAGCCGGAGTCCGACAGACAGACCGCCGATGAGAGATGTGTTGTTGATTCTTCAAGA
GGCAAAGCCAAAGAGGAAGACAGTAGGGGATAATGTGATCGTCGTTGGTGATGTTAATGAT
GTCAATTTCGAAGATGTTTGTAGTGTTGATGTTGGTCATGATGTTAAATGTCAAAGGATTGGG
GTGTGA

FIG. 16A 1. 35S promoter
CCTGTCCTCTCCAAATGAAATGAACTTCCTTATATAGAGGAAGGGTCTTGCGA
AGGATAGTGGGATTGTGCGTCATCCCTTACGTCAGTGGAGATATCACATCAAT
CCACTTGCTTTGAAGACGTGGTTGGAACGTCTTCTTTTTCCACGATGCTCCTC
GTGGGTGGGGGTCCATCTTTGGGACCACTGTCGGCAGAGGCATCTTGAACGA
TAGCCTTTCCTTTATCGCAATGATGGCATTTGTAGGTGCCACCTTCCTTTTCTA
CTGTCCTTTTGATGAAGTGACAGATAGCTGGGCAATGGAATCCGAGGAGGTT
TCCCGATATTACCCTTTGTTGAAAAGTCTCAATAGCCCTTTGGTCTTCTGAGA
CTGTATCTTTGATATTCTTGGAGTAGACGAGAGTGTCGTGCTCCACCATGTTG
ACGAAGATTTTCTTCTTGTCATTGAGTCGTAAAAGACTCTGTATGAACTGTTC
GCCAGTCTTCACGGCGAGTTCTGTTAGATCCTCGATCTGAATTTTTGACTCCA
TGGGAATTC

FIG. 16B

2. IRX3 promoter
AAAAATAAGTAAAAGATCTTTTAGTTGTTTGCTTTGTATGTTGCGAACAGTTT
GATTCTGTTTTTCTTTTTCCTTTTTTGGGTAATTTTCTTATAACTTTTTTCATA
GTTTCGATTATTTGGATAAAATTTTCAGATTGAGGATCATTTTATTTATTTATTA
GTGTAGTCTAATTTAGTTGTATAACTATAAAATTGTTGTTTGTTTCCGAATCATA
AGTTTTTTTTTTTTTGGTTTTGTATTGATAGGTGCAAGAGACTCAAAATTCTG
GTTTCGATGTTAACAGAATTCAAGTAGCTGCCCACTTGATTCGATTTGTTTTG
TATTTGGAAACAACCATGGCTGGTCAAGGCCCAGCCCGTTGTGCTTCTGAAC
CTGCCTAGTCCCATGGACTAGATCTTTATCCGCAGACTCCAAAAGAAAAAGG
ATTGGCGCAGAGGAATTGTCATGGAAACAGAATGAACAAGAAAGGGTGAAG
AAGATCAAAGGCATATATGATCTTTACATTCTCTTTAGCTTATGTATGCAGAAA
ATTCACCTAATTAAGGACAGGGAACGTAACTTGGCTTGCACTCCTCTCACCA
AACCTTACCCCCTAACTAATTTTAATTCAAAATTACTAGTATTTTGGCCGATCA
CTTTATATAATAAGATACCAGATTTATTATATTTACGAATTATCAGCATGCATATA
CTGTATATAGTTTTTTTTTTGTTAAAGGGTAAATAATAGGATCCTTTTGAATA
AAATGAACATATATAATTAGTATAATGAAAACAGAAGGAAATGAGATTAGGAC
AGTAAGTAAAATGAGAGAGACCTGCAAAGGATAAAAAAGAGAAGCTTAAGG
AAACCGCGACGATGAAAGAAAGACATGTCATCAGCTGATGGATGTGAGTGAT
GAGTTTGTTGCAGTTGTGTAGAAATTTTTACTAAAACAGTTGTTTTTACAAAA
AAGAAATAATATAAAACGAAAGCTTAGCTTGAAGGCAATGGAGACTCTACAA
CAAACTATGTACCATACAGAGAGAGAAACTAAAAGCTTTTCACACATAAAAA
CCAAACTTATTCGTCTCTCATTGATCACCGTTTTGTTCTCTCAAGATCGCTGCT
AATCT

FIG. 16C

3. LRR promoter
GTGTTTTTGGACATAATGATTTGAATGATATTAAACAAAAAAAAGGCATCTTAT
TGTAATTAAATTAATAAAGTAATGGACGTTTTTGTTAGTGAGACGCCTGAACTT
GTCATGACATACAGACATACCAATTCCATTCATGCAGGAGAATGTTGAATAATG
TGAGGGAACGTGAATAGAGGAACTATTTTTGGGTAAATGCAATCACATCCTCT
CATTCTCAAACCTCCAAACCAAAATGTGTAGTTTTCTTCCTCTCCAAGAAACA
ATACTCTTATGACTGCAATACCACACTTTAGTCTGTGTGTGTTTTTAATAGAAT
GGTATAAAGAAGCATACTGAAATGGTGTTTTTAAATGAAAGATCAAATCACAA
CAATATCCAAAACCTAAAATAAAAAGATTGTGGGCTTATTTATTAGGCCCATAG
TCTTTATTCTTTAAGGGCAAACTTTCAGAGATGCGGGTCTACATTATTTGGCCC
GAACCAGTAAAACCTGCAGGCTTCTAGAGAAACCCATACGAATGGCGAGTTA
CCGGTCAGAAGCGTAATCACCGGTCCTTAAATTTCATTTCCAGGCGAACGATT
TGGAAAAGTCGGTGTCGTTAAGAAAAGACAATTCCTACCCTTTTGTCGTCAT
TTGTTTGCTAATTGCTACCTTTATAATGTAAGGGAGGAGTGGAGTTGCTATTAT
TATTCCGACATTTAAGTGTTATGTGTTTGTCGGATCGGATTCTATCTTAAGAATC
TTATCTTATTCCCCCCGAATATCATTGACTTTGTCTTAAATCTTAATTTGTTATGT
TTGCACTTAAACTCTCTCTTTTCGTTAGTGCACACAACTCGTATTCCATCAAA
ATCAATGATAAAATAATTCTTACCAAATTAACAAAAAGTGAATAAATATCACAT
TATTCATACTAATCTTCATGATATCATCACAAGAATAATGTGTGCACACAAAAA
ACCACTGTTTGTTTCCGCGTGAAGTGAACTCTCAAGAGTCTCCAATGTTGACC
AAATCAAACAACCTCTTAACTTCTTTGACCAACAATTTTTAAAACCATGAAAT
AAGTTACATACGAAGACTTGACTTGTTTCTTTCTCTTAAAAATCAAAGTTTAA
CTGCTTCAGAGTTTAATTTTCAATGTGTCCATATACAATTCATTTTAAATCTAAA
GCAAATTCCTCTTCTTTTTTTTCCTTTAATTTATTTTATTTTTTATGGAGTGAGTT
GAGTTCTGTATACATTCTTTGTAAATGGAAAAAATAAAAAAACAGCTTGATT
AAAAAAAATAAAGAAATTGAGAAAAAGACAAGAATTTAAATAATAATAAAAT
AATGTAAAAAGAAAGTGAACAACAAAAAAAGACACAAAAAAGTAAAACTGA
AAAGGAGTATTTCTCTGTCATTTCCCACACCAATCGCATAATCGATTTCTTCCA
ACTTCAATAAAGGGGAACCAACGTAACCCTAATTTTGCTTTCTCCTCTTTGTTC
AGAAAATTTTCCCTTTACTCTCAAATTCCTTTTCGATTTCCCTCTCTTAAACCT
CCGAAAGCTCAC

FIG. 16D

4. Nodulin promoter
GAGGGTTGTCATGTCAGCTAAACAGCAGAAAAATAAAAGAATGTGGGAGACA
GGCTTTGCCCTTTTACACATTTTAAGCTCTCTTCTTTATTTTCTAAAAACACTAT
AGTACACAGTTAAAAATTTGCGGGCCCTTTGTTTAATCGATTTAGATTTAACCA
ACAGCTTCATAGTCGTTTCTTCTTGTTAGAAATCAATAAATGAAAAGTTGGTTG
TTTTGAAAGCATATAATTAACTAACAATGTATCATGTTGTGAAACAAAAGCTGA
TGATAAATGTTAAATATAGTGTCCAAAATTTTGGGAATGTCTTCAAATTTTGATT
TTAAAACATATGAGATGTACCAACATCCACAAAATGTTTGTGAAGTTGTGACTT
AGTGAGACGTTGTCACTTTATTATCTCGTTTTGGTAACGGTAAGTGCATGTGAA
CGTGTTTGATTATAAGTTTAACCCGACTTTGTTTACGTGGTCATAGTTTCCAATA
AGGCTAAGTAGAATAGTGTATGATAGTTTTCAATTCAAGAGTCTTTTTTTTCCAA
GAAAATCCGAAAACACAATCGTTTATTTTAATATCTCAAAAGAAATCATATTTCT
TAGGTAAAACTATCATACGTTGAGTTTTTCTTTCTCCTTTTGCGATTTTCCCTGA
AATATATTTATGTTGTGTGTGTGCTTTGTAAACAAAATAATAATGAACGTAATAA
TAGTAAAACAAAAAGTAACCTATATTATTATCATACTTGATATAACCCAATAGAG
AAATAATAATATAAATTAAAATTTTATTTCCCAATTCAAAAATCATAATCAAGGA
GTGAATGCTGCCAGTAGACCAAAGTAACAATATTTGGTGTGTACATCAAATGAT
AGGAAACAACAAAAACTCATTAATATACCTAAATCCATATATATATATATATATATA
TATTTCAATATTTCACATTGTTATAATTAGGTTTAATAGATACCATATTAGAAATCT
CAGTATGGTGGTTC

FIG. 16E 5. 35S Terminator
GGAATTAGAAATTTTATTGATAGAAGTATTTTACAAATACAAATACATACTAAGG
GTTTCTTATATGCTCAACACATGAGCGAAACCCTATAAGAACCCTAATTCCCTTA
TCTGGGAACTACTCACACATTATTATAGAGAGAGATAGATTTGTAGAGAGAGAC
TGGTGATTTCAGCG

FIG. 16F

6. NOS Terminator
GATCGTTCAAACATTTGGCAATAAAGTTTCTTAAGATTGAATCCTGTTGCCGGT
CTTGCGATGATTATCATATAATTTCTGTTGAATTACGTTAAGCATGTAATAATTAA
CATGTAATGCATGACGTTATTTATGAGATGGGTTTTTATGATTAGAGTCCCGCAA
TTATACATTTAATACGCGATAGAAAACAAAATATAGCGCGCAAACTAGGATAAA
TTATCGCGCGCGGTGTCATCTATGTTACTAGATCGG

Wild type, 35S::CLE41, 35S::CLE41 35S::PXY, 35S::PXY plant (LHS-RHS) at 50 days

Hypocotyls cross section 35S::CLE41 35S::PXY (A), 35S::CLE41 (B), 35S::PXY (C), Wild type (D) section Wild type (A), 35S::CLE41 (B), 35S::CLE42 (C), 35S::PXY (D) and 35S::CLE41 35S::PXY (E). bar scale 0.5mm

SEQUENCE LISTING

<160> NUMBER OF SEQ ID NOS: 63

<210> SEQ ID NO 1
<211> LENGTH: 131
<212> TYPE: PRT
<213> ORGANISM: Populus tremula x Populus tremuloides

<400> SEQUENCE: 1

Met Asp Ile Glu Pro Leu Trp Ala Leu Gly Gly Trp Phe Leu Phe Ser
1               5                   10                  15

Ile Thr Cys Met Ala Thr Pro Lys Ser Gln Ser Thr Ile Ser Glu Thr
            20                  25                  30

Phe Lys Arg Ser His His Phe Phe Leu Phe Leu Ala Leu Leu Phe Val
        35                  40                  45

Phe Ile Leu Leu Thr Ser Pro Ser Lys Pro Ile Asn Pro Thr Asn Thr
    50                  55                  60

Val Ala Ser Ile Ser Ile Lys Arg Leu Leu Leu Glu Ser Ser Glu Pro
65                  70                  75                  80

Ala Ser Thr Thr Met Asn Leu His Pro Lys His Thr Gln Gly Thr Arg
                    85                  90                  95

Thr Ser Ser Ser Ser Ser Pro Pro Ser Ser Lys Ser Thr Arg Lys
            100                 105                 110

Lys Phe Gly Ala Gln Ala His Glu Val Pro Ser Gly Pro Asn Pro Ile
        115                 120                 125

Ser Asn Arg
    130

<210> SEQ ID NO 2
<211> LENGTH: 113
<212> TYPE: PRT
<213> ORGANISM: Populus tremula x Populus tremuloides

<400> SEQUENCE: 2

Met Ala Thr Pro Lys Thr Gln Ser Thr Thr Ile Ser Asp His Gln Thr
1               5                   10                  15

Cys Thr Lys Ala His His Phe Leu Ser Leu Leu Ala Leu Leu Phe Ile
            20                  25                  30

Phe Ile Leu Leu Thr Thr Ser Thr Lys Pro Ile Asn Pro Thr Asn Met
        35                  40                  45

Ala Ala Ser Ile Ser Ile Lys Arg Leu Leu Leu Glu Ser Ser Glu Pro
    50                  55                  60

Ala Ser Thr Thr Met Asn Leu His Pro Lys Gln Thr Gln Asp Ala Arg
65                  70                  75                  80

Thr Ser Ser Ser Ser Thr Ser Ser Lys Ser Thr Arg Thr Lys Phe
                85                  90                  95

Gly Ala Ala Ala His Glu Val Pro Ser Gly Pro Asn Pro Ile Ser Asn
            100                 105                 110

Arg

<210> SEQ ID NO 3
<211> LENGTH: 99
<212> TYPE: PRT
<213> ORGANISM: Arabidopsis thaliana

<400> SEQUENCE: 3

Met Ala Thr Ser Asn Asp Gln Thr Asn Thr Lys Ser Ser His Ser Arg
1               5                   10                  15

Thr Leu Leu Leu Leu Phe Ile Phe Leu Ser Leu Leu Leu Phe Ser Ser
            20                  25                  30

Leu Thr Ile Pro Met Thr Arg His Gln Ser Thr Ser Met Val Ala Pro
        35                  40                  45

Phe Lys Arg Val Leu Leu Glu Ser Ser Val Pro Ala Ser Ser Thr Met
    50                  55                  60

Asp Leu Arg Pro Lys Ala Ser Thr Arg Arg Ser Arg Thr Ser Arg Arg
65                  70                  75                  80

Arg Glu Phe Gly Asn Asp Ala His Glu Val Pro Ser Gly Pro Asn Pro
                85                  90                  95

Ile Ser Asn

<210> SEQ ID NO 4
<211> LENGTH: 110
<212> TYPE: PRT
<213> ORGANISM: Arabidopsis thaliana

<400> SEQUENCE: 4

```
Met Ile Thr Ile Asp Gln Thr Ser Ile Lys Ser Leu His Phe His Gln
1               5                   10                  15

Val Ile Arg Leu Ile Ile Thr Ile Phe Leu Ala Phe Leu Phe Leu
            20                  25                  30

Ile Gly Pro Thr Ser Ser Met Asn His Leu His Glu Ser Ser Ser Lys
            35                  40                  45

Asn Thr Met Ala Pro Ser Lys Arg Phe Leu Leu Gln Pro Ser Thr Pro
        50                  55                  60

Ser Ser Ser Thr Met Lys Met Arg Pro Thr Ala His Pro Arg Arg Ser
65                  70                  75                  80

Gly Thr Ser Ser Ser Ala Arg Lys Arg Arg Arg Glu Phe Arg Ala
                85                  90                  95

Glu Ala His Glu Val Pro Ser Gly Pro Asn Pro Ile Ser Asn
            100                 105                 110
```

<210> SEQ ID NO 5
<211> LENGTH: 115
<212> TYPE: PRT
<213> ORGANISM: Populus tremula x Populus tremuloides

<400> SEQUENCE: 5

```
Met Ala Ser Asp Val Gly Ser Pro Tyr Pro Thr Ser Leu Thr Ile Leu
1               5                   10                  15

Phe Phe Leu Leu Ile Met Ser His Thr Thr Met Ala Thr Lys Glu His
            20                  25                  30

Arg Phe Leu Leu Gly Thr Ser Arg Asp Gly Glu Ile Lys Lys Asn Asp
            35                  40                  45

Met Glu Tyr Phe Ala Asn Arg Arg His Asp Met Gly Asn Ala Lys Thr
        50                  55                  60

Val Ser Lys Ala Asn Ile Ile His Ile Pro Pro Pro Ser Ser Arg Arg
65                  70                  75                  80

Arg Gly Arg Phe Arg Ala His Arg Ser Pro Leu Pro Trp Gln Glu Gly
                85                  90                  95

Val Glu Asn Asp Ser Ala His Glu Val Pro Ser Gly Pro Asn Pro Ile
            100                 105                 110

Ser Asn Arg
        115
```

<210> SEQ ID NO 6
<211> LENGTH: 115
<212> TYPE: PRT
<213> ORGANISM: Populus tremula x Populus tremuloides

<400> SEQUENCE: 6

```
Met Ala Ser Asp Val Gly Ser Pro Asn Leu Thr Ser Leu Thr Ile Leu
1               5                   10                  15

Phe Phe Leu Leu Ile Met Phe His Thr Thr Met Ala Asn Lys Asp His
            20                  25                  30

Arg Phe Leu Leu Ser Thr Thr Arg Asp Gly Gly Tyr Phe Lys Lys Ser
            35                  40                  45

Leu Met Glu Phe Ser Thr Thr Arg Pro Asp Met Gly Asn Ala Lys Thr
        50                  55                  60

Val Ser Lys Ala Asn Val Ile His Ile Pro Pro Gln Ser Ser Arg Arg
65                  70                  75                  80

Arg Gly Arg Phe Arg Ala His Arg Ser Pro Leu Pro Trp Gln Glu Gly
                85                  90                  95
```

```
Ile Phe Ser Ala Ser Ala His Glu Val Pro Ser Gly Pro Asn Pro Ile
                100                 105                 110

Ser Asn Arg
        115

<210> SEQ ID NO 7
<211> LENGTH: 45
<212> TYPE: PRT
<213> ORGANISM: Populus tremula x Populus tremuloides

<400> SEQUENCE: 7

Met Gln Met Ile Asp Ala Phe Thr Leu Leu Val Leu Ser Phe Met Leu
1               5                   10                  15

Arg His Lys Gln Val Ala Glu Lys Arg Ile His Lys Ser Pro Ser Gly
                20                  25                  30

Pro Asn Pro Val Gly Asn His Asn Pro Pro Ser Lys Gln
            35                  40                  45

<210> SEQ ID NO 8
<211> LENGTH: 76
<212> TYPE: PRT
<213> ORGANISM: Arabidopsis thaliana

<400> SEQUENCE: 8

Met Arg Arg His Asp Ile Ile Ile Lys Leu Leu Leu Met Cys Leu
1               5                   10                  15

Leu Leu Ser Arg Phe Val Thr Arg Glu Cys Gln Glu Val His Phe Lys
                20                  25                  30

Ile Gly Pro Ala Lys Ile Ile Ala Lys Pro Asn Asn Ala Arg Val Asn
            35                  40                  45

Pro Thr Trp Gly Glu Glu Lys Lys Trp His Lys His Pro Ser Gly Pro
        50                  55                  60

Asn Pro Thr Gly Asn Arg His Pro Pro Val Lys His
65                  70                  75

<210> SEQ ID NO 9
<211> LENGTH: 104
<212> TYPE: PRT
<213> ORGANISM: Oryza sativa

<400> SEQUENCE: 9

Met Ala Arg Ala Arg Trp Ile Gly Asp Gly Arg Arg Pro Ala Ala Ala
1               5                   10                  15

Leu Pro Leu Leu Gly Leu Cys Ala Phe Leu Cys Ala Val Met Leu Val
                20                  25                  30

Val Ser Leu Ala Pro Pro Gly Glu Glu Glu Glu Ala Lys Val
            35                  40                  45

Arg Ser Ser Ser Leu Pro Ala Ala Thr Ser Val Pro Ala Gly Gly
    50                  55                  60

Arg Arg Leu Leu Leu Pro Ala Ala Arg Thr Arg Arg Phe Arg Pro Arg
65                  70                  75                  80

Arg Trp Asn Ser Ala Gly Ile Asp Asp Ser Lys His Glu Val Pro Ser
                85                  90                  95

Gly Pro Asn Pro Asp Ser Asn Arg
            100

<210> SEQ ID NO 10
<211> LENGTH: 88
<212> TYPE: PRT
```

<213> ORGANISM: Arabidopsis thaliana

<400> SEQUENCE: 10

Met Arg Ser Pro His Ile Thr Ile Ser Leu Val Phe Leu Phe Phe Leu
1               5                   10                  15

Phe Leu Ile Ile Gln Thr His Gln Arg Thr Ile Asp Gln Thr His Gln
            20                  25                  30

Ile Gly Ser Asn Val Gln His Val Ser Asp Met Ala Val Thr Ser Pro
        35                  40                  45

Glu Gly Lys Arg Arg Glu Arg Phe Arg Val Arg Arg Pro Met Thr Thr
50                  55                  60

Trp Leu Lys Gly Lys Met Ile Gly Ala Asn Glu His Gly Val Pro Ser
65                  70                  75                  80

Gly Pro Asn Pro Ile Ser Asn Arg
                85

<210> SEQ ID NO 11
<211> LENGTH: 120
<212> TYPE: PRT
<213> ORGANISM: Oryza sativa

<400> SEQUENCE: 11

Met Asp Thr Ala Arg Pro Val His Pro Leu Arg Val His Gly Glu Ser
1               5                   10                  15

Ile Arg Gly Leu Leu Leu Leu Leu Leu Phe Val Val Gln Cys Ser
            20                  25                  30

Leu Leu Ser Cys Cys Leu Ala His Ala Ala Ala Ala Asp Ala Val
        35                  40                  45

Asp Arg Asp Asp Pro Val Val Thr Ala Thr Ala Gly Arg Gly Arg Arg
50                  55                  60

Phe Leu Pro Ser Pro Ala Leu Gln Leu His Ser Val Gln Val Asn Val
65                  70                  75                  80

Ala Ala His Pro Trp Ser Lys Glu Arg Arg Ser Arg Arg Arg Arg
            85                  90                  95

Arg Arg Arg Ala Ala Thr Leu Met Ala Val Ser Lys His Gln Val Pro
            100                 105                 110

Thr Gly Ala Asn Pro Asp Ser Asn
        115                 120

<210> SEQ ID NO 12
<211> LENGTH: 144
<212> TYPE: PRT
<213> ORGANISM: Artificial Sequence
<220> FEATURE:
<223> OTHER INFORMATION: Consensus gene for CLE41 protein derived from
      Arabidopsis thaliana.
<220> FEATURE:
<221> NAME/KEY: MISC_FEATURE
<222> LOCATION: (1)..(19)
<223> OTHER INFORMATION: Xaa can be any naturally occurring amino acid.
<220> FEATURE:
<221> NAME/KEY: MISC_FEATURE
<222> LOCATION: (23)..(30)
<223> OTHER INFORMATION: Xaa can be any naturally occurring amino acid.
<220> FEATURE:
<221> NAME/KEY: MISC_FEATURE
<222> LOCATION: (32)..(37)
<223> OTHER INFORMATION: Xaa can be any naturally occurring amino acid.
<220> FEATURE:
<221> NAME/KEY: MISC_FEATURE
<222> LOCATION: (40)..(40)
<223> OTHER INFORMATION: Xaa can be any naturally occurring amino acid.
<220> FEATURE:

```
<221> NAME/KEY: MISC_FEATURE
<222> LOCATION: (43)..(45)
<223> OTHER INFORMATION: Xaa can be any naturally occurring amino acid.
<220> FEATURE:
<221> NAME/KEY: MISC_FEATURE
<222> LOCATION: (50)..(53)
<223> OTHER INFORMATION: Xaa can be any naturally occurring amino acid.
<220> FEATURE:
<221> NAME/KEY: MISC_FEATURE
<222> LOCATION: (56)..(82)
<223> OTHER INFORMATION: Xaa can be any naturally occurring amino acid.
<220> FEATURE:
<221> NAME/KEY: MISC_FEATURE
<222> LOCATION: (86)..(87)
<223> OTHER INFORMATION: Xaa can be any naturally occurring amino acid.
<220> FEATURE:
<221> NAME/KEY: MISC_FEATURE
<222> LOCATION: (89)..(89)
<223> OTHER INFORMATION: Xaa can be any naturally occurring amino acid.
<220> FEATURE:
<221> NAME/KEY: MISC_FEATURE
<222> LOCATION: (92)..(92)
<223> OTHER INFORMATION: Xaa can be any naturally occurring amino acid.
<220> FEATURE:
<221> NAME/KEY: MISC_FEATURE
<222> LOCATION: (94)..(94)
<223> OTHER INFORMATION: Any amino acid.
<220> FEATURE:
<221> NAME/KEY: MISC_FEATURE
<222> LOCATION: (96)..(96)
<223> OTHER INFORMATION: Xaa can be any naturally occurring amino acid.
<220> FEATURE:
<221> NAME/KEY: MISC_FEATURE
<222> LOCATION: (99)..(99)
<223> OTHER INFORMATION: Xaa can be any naturally occurring amino acid.
<220> FEATURE:
<221> NAME/KEY: MISC_FEATURE
<222> LOCATION: (102)..(119)
<223> OTHER INFORMATION: Xaa can be any naturally occurring amino acid.
<220> FEATURE:
<221> NAME/KEY: MISC_FEATURE
<222> LOCATION: (121)..(123)
<223> OTHER INFORMATION: Xaa can be any naturally occurring amino acid.
<220> FEATURE:
<221> NAME/KEY: MISC_FEATURE
<222> LOCATION: (138)..(144)
<223> OTHER INFORMATION: Xaa can be any naturally occurring amino acid.

<400> SEQUENCE: 12

Xaa Xaa Xaa Xaa Xaa Xaa Xaa Xaa Xaa Xaa Xaa Xaa Xaa Xaa Xaa
1               5                   10                  15

Xaa Xaa Xaa Met Ala Thr Xaa Xaa Xaa Xaa Xaa Xaa Xaa Ser Xaa
            20                  25                  30

Xaa Xaa Xaa Xaa Xaa Leu Leu Xaa Leu Phe Xaa Xaa Xaa Leu Ala Leu
        35                  40                  45

Leu Xaa Xaa Xaa Xaa Leu Leu Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Ser Ser Val Xaa Xaa Ser Xaa Thr Met Xaa Leu Xaa Pro Xaa
                85                  90                  95

Ala Ser Xaa Arg Arg Xaa Xaa Xaa Xaa Xaa Xaa Xaa Xaa Xaa
            100                 105                 110

Xaa Xaa Xaa Xaa Xaa Xaa Xaa Phe Xaa Xaa Xaa Ala His Glu Val Pro
        115                 120                 125

Ser Gly Pro Asn Pro Ile Ser Asn Arg Xaa Xaa Xaa Xaa Xaa Xaa
    130                 135                 140

<210> SEQ ID NO 13
```

<211> LENGTH: 313
<212> TYPE: PRT
<213> ORGANISM: Oryza sativa

<400> SEQUENCE: 13

```
Val Lys Glu Ala Asn Val Val Gly Met Gly Ala Thr Gly Val Val Tyr
 1               5                  10                  15

Lys Ala Glu Leu Pro Arg Ala Arg Ala Val Ile Ala Val Lys Lys Leu
            20                  25                  30

Trp Arg Pro Ala Ala Ala Glu Ala Ala Ala Ala Pro Glu Leu
        35                  40                  45

Thr Ala Glu Val Leu Lys Glu Val Gly Leu Leu Gly Arg Leu Arg His
    50                  55                  60

Arg Asn Ile Val Arg Leu Leu Gly Tyr Met His Asn Glu Ala Asp Ala
 65                  70                  75                  80

Met Met Leu Tyr Glu Phe Met Pro Asn Gly Ser Leu Trp Glu Ala Leu
                85                  90                  95

His Gly Pro Pro Glu Arg Arg Thr Leu Val Asp Trp Val Ser Arg Tyr
            100                 105                 110

Asp Val Ala Ala Gly Val Ala Gln Gly Leu Ala Tyr Leu His His Asp
        115                 120                 125

Cys His Pro Val Ile His Arg Asp Ile Lys Ser Asn Asn Ile Leu
    130                 135                 140

Leu Asp Ala Asn Met Glu Ala Arg Ile Ala Asp Phe Gly Leu Ala Arg
145                 150                 155                 160

Ala Leu Gly Arg Ala Gly Glu Ser Val Ser Val Ala Gly Ser Tyr
                165                 170                 175

Gly Tyr Ile Ala Pro Glu Tyr Gly Tyr Thr Met Lys Val Asp Gln Lys
            180                 185                 190

Ser Asp Thr Tyr Ser Tyr Gly Val Val Leu Met Glu Leu Ile Thr Gly
        195                 200                 205

Arg Arg Ala Val Glu Ala Ala Phe Gly Glu Gly Gln Asp Ile Val Gly
    210                 215                 220

Trp Val Arg Asn Lys Ile Arg Ser Asn Thr Val Glu Asp His Leu Asp
225                 230                 235                 240

Gly Gln Leu Val Gly Ala Gly Cys Pro His Val Arg Glu Glu Met Leu
                245                 250                 255

Leu Val Leu Arg Thr Ala Val Leu Cys Thr Ala Arg Leu Pro Arg Asp
            260                 265                 270

Arg Pro Ser Met Arg Asp Val Ile Thr Met Leu Gly Glu Ala Lys Pro
        275                 280                 285

Arg Arg Lys Ser Gly Ser Ser Thr Gly Ser Ala Ser Ala Lys Ala Pro
    290                 295                 300

Thr Pro Ala Pro Pro Ala Val Ala Ala
305                 310
```

<210> SEQ ID NO 14
<211> LENGTH: 305
<212> TYPE: PRT
<213> ORGANISM: Oryza sativa

<400> SEQUENCE: 14

```
Ile Lys Glu Ala Asn Ile Val Gly Met Gly Gly Thr Gly Val Val Tyr
 1               5                  10                  15

Arg Ala Asp Met Pro Arg His His Ala Val Val Ala Val Lys Lys Leu
            20                  25                  30
```

Trp Arg Ala Ala Gly Cys Pro Glu Glu Ala Thr Thr Val Asp Gly Arg
         35                  40                  45

Thr Asp Val Glu Ala Gly Gly Glu Phe Ala Ala Glu Val Lys Leu Leu
 50                  55                  60

Gly Arg Leu Arg His Arg Asn Val Val Arg Met Leu Gly Tyr Val Ser
 65                  70                  75                  80

Asn Asn Leu Asp Thr Met Val Ile Tyr Glu Tyr Met Val Asn Gly Ser
                 85                  90                  95

Leu Trp Asp Ala Leu His Gly Gln Arg Lys Gly Lys Met Leu Met Asp
                 100                 105                 110

Trp Val Ser Arg Tyr Asn Val Ala Ala Gly Val Ala Gly Leu Ala
                 115                 120                 125

Tyr Leu His His Asp Cys Arg Pro Val Ile His Arg Asp Val Lys
 130                 135                 140

Ser Ser Asn Val Leu Leu Asp Asp Asn Met Asp Ala Lys Ile Ala Asp
 145                 150                 155                 160

Phe Gly Leu Ala Arg Val Met Ala Arg Ala His Glu Thr Val Ser Val
                 165                 170                 175

Val Ala Gly Ser Tyr Gly Tyr Ile Ala Pro Glu Tyr Gly Tyr Thr Leu
                 180                 185                 190

Lys Val Asp Gln Lys Ser Asp Ile Tyr Ser Phe Gly Val Val Leu Met
                 195                 200                 205

Glu Leu Leu Thr Gly Arg Arg Pro Ile Glu Pro Glu Tyr Gly Glu Ser
 210                 215                 220

Gln Asp Ile Val Gly Trp Ile Arg Glu Arg Leu Arg Ser Asn Thr Gly
 225                 230                 235                 240

Val Glu Glu Leu Leu Asp Ala Ser Val Gly Gly Arg Val Asp His Val
                 245                 250                 255

Arg Glu Glu Met Leu Leu Val Leu Arg Val Ala Val Leu Cys Thr Ala
                 260                 265                 270

Lys Ser Pro Lys Asp Arg Pro Thr Met Arg Asp Val Val Thr Met Leu
 275                 280                 285

Gly Glu Ala Lys Pro Arg Arg Lys Ser Ser Ser Ala Thr Val Ala Ala
 290                 295                 300

Thr
305

<210> SEQ ID NO 15
<211> LENGTH: 309
<212> TYPE: PRT
<213> ORGANISM: Oryza sativa

<400> SEQUENCE: 15

Gly Ser Asp Gly Ile Val Gly Ala Gly Ser Ser Gly Thr Val Tyr Arg
 1               5                   10                  15

Ala Lys Met Pro Asn Gly Glu Val Ile Ala Val Lys Lys Leu Trp Gln
                 20                  25                  30

Ala Pro Ala Ala Gln Lys Glu Ala Ala Ala Pro Thr Glu Gln Asn Gln
                 35                  40                  45

Lys Leu Arg Gln Asp Ser Asp Gly Gly Gly Gly Lys Arg Thr Val
             50                  55                  60

Ala Glu Val Glu Val Leu Gly His Leu Arg His Arg Asn Ile Val Arg
 65                  70                  75                  80

Leu Leu Gly Trp Cys Thr Asn Gly Glu Ser Thr Met Leu Leu Tyr Glu

```
                        85                  90                  95
Tyr Met Pro Asn Gly Ser Leu Asp Glu Leu Leu His Gly Ala Ala Ala
                100                 105                 110

Lys Ala Arg Pro Gly Trp Asp Ala Arg Tyr Lys Ile Ala Val Gly Val
                115                 120                 125

Ala Gln Gly Val Ser Tyr Leu His His Asp Cys Leu Pro Ala Ile Ala
            130                 135                 140

His Arg Asp Ile Lys Pro Ser Asn Ile Leu Leu Asp Asp Met Glu
145                 150                 155                 160

Ala Arg Val Ala Asp Phe Gly Val Ala Lys Ala Leu Gln Ser Ala Ala
                165                 170                 175

Pro Met Ser Val Val Ala Gly Ser Cys Gly Tyr Ile Ala Pro Glu Tyr
            180                 185                 190

Thr Tyr Thr Leu Lys Val Asn Glu Lys Ser Asp Val Tyr Ser Pro Gly
                195                 200                 205

Val Val Leu Leu Glu Ile Leu Thr Gly Arg Arg Ser Val Glu Ala Glu
            210                 215                 220

Tyr Gly Glu Gly Asn Asn Ile Val Asp Trp Val Arg Arg Lys Val Ala
225                 230                 235                 240

Gly Gly Gly Val Gly Asp Val Ile Asp Ala Ala Trp Ala Asp Asn
                245                 250                 255

Asp Val Gly Gly Thr Arg Asp Glu Met Ala Leu Ala Leu Arg Val Ala
            260                 265                 270

Leu Leu Cys Thr Ser Arg Cys Pro Gln Glu Arg Pro Ser Met Arg Glu
                275                 280                 285

Val Leu Ser Met Leu Gln Glu Ala Arg Pro Lys Arg Lys Asn Ser Ala
            290                 295                 300

Lys Lys Gln Val Lys
305

<210> SEQ ID NO 16
<211> LENGTH: 305
<212> TYPE: PRT
<213> ORGANISM: Populus tremula x Populus tremuloides

<400> SEQUENCE: 16

Met Ser Asp Lys Ile Leu Gly Met Gly Ser Thr Gly Thr Val Tyr Lys
1               5                   10                  15

Ala Glu Met Pro Gly Gly Glu Ile Ile Ala Val Lys Lys Leu Trp Gly
                20                  25                  30

Lys His Lys Glu Asn Ile Arg Arg Arg Gly Val Leu Ala Glu Val
            35                  40                  45

Asp Val Leu Gly Asn Val Arg His Arg Asn Ile Val Arg Leu Leu Gly
        50                  55                  60

Cys Cys Ser Asn Arg Glu Cys Thr Met Leu Leu Tyr Glu Tyr Met Pro
65                  70                  75                  80

Asn Gly Asn Leu His Asp Leu Leu His Gly Lys Asn Lys Gly Asp Asn
                85                  90                  95

Leu Val Gly Asp Trp Leu Thr Arg Tyr Lys Ile Ala Leu Gly Val Ala
                100                 105                 110

Gln Gly Ile Cys Tyr Leu His His Asp Cys Asp Pro Val Ile Val His
            115                 120                 125

Arg Asp Leu Lys Pro Ser Asn Ile Leu Leu Asp Gly Glu Met Glu Ala
        130                 135                 140
```

```
Arg Val Arg Asp Phe Gly Val Ala Lys Leu Ile Gln Ser Asp Glu Ser
145                 150                 155                 160

Met Ser Val Ile Ala Gly Ser Tyr Gly Tyr Ile Ala Pro Glu Tyr Ala
                165                 170                 175

Tyr Thr Leu Gln Val Asp Glu Lys Ser Asp Ile Tyr Ser Tyr Gly Val
            180                 185                 190

Val Leu Met Glu Ile Ile Ser Gly Lys Arg Ser Val Asp Ala Glu Phe
        195                 200                 205

Gly Asp Gly Asn Ser Ile Val Asp Trp Val Arg Ser Lys Ile Lys Ala
    210                 215                 220

Lys Asp Gly Val Asn Asp Ile Leu Asp Lys Asp Ala Gly Ala Ser Ile
225                 230                 235                 240

Ala Ser Val Arg Glu Glu Met Met Gln Met Leu Arg Ile Ala Leu Leu
                245                 250                 255

Cys Thr Ser Arg Asn Pro Ala Asp Arg Pro Ser Met Arg Asp Val Val
            260                 265                 270

Leu Met Leu Gln Glu Ala Lys Pro Lys Arg Lys Leu Pro Gly Ser Ile
        275                 280                 285

Val Ser Val Gly Ser Gly Asp His Ile Val Thr Val Asp Gly Ala Ile
    290                 295                 300

Ala
305

<210> SEQ ID NO 17
<211> LENGTH: 251
<212> TYPE: PRT
<213> ORGANISM: Populus tremula x Populus tremuloides

<400> SEQUENCE: 17

Lys Thr Asp Asn Ile Leu Gly Met Gly Ser Thr Gly Thr Val Tyr Lys
1               5                   10                  15

Ala Glu Met Pro Asn Gly Glu Ile Ile Ala Val Lys Lys Leu Trp Gly
                20                  25                  30

Lys Asn Lys Glu Asn Gly Lys Ile Arg Arg Arg Lys Ser Gly Val Leu
            35                  40                  45

Ala Glu Val Asp Val Leu Gly Asn Val Arg His Arg Asn Ile Val Arg
        50                  55                  60

Leu Leu Gly Cys Cys Thr Asn Arg Asp Cys Thr Met Leu Leu Tyr Glu
65                  70                  75                  80

Tyr Met Pro Asn Gly Ser Leu Asp Asp Leu Leu His Gly Gly Asp Lys
                85                  90                  95

Thr Met Thr Ala Ala Ala Glu Trp Thr Ala Leu Tyr Gln Ile Ala Ile
            100                 105                 110

Gly Val Ala Gln Gly Ile Cys Tyr Leu His His Asp Cys Asp Pro Val
        115                 120                 125

Ile Val His Arg Asp Leu Lys Pro Ser Asn Ile Leu Leu Asp Ala Asp
    130                 135                 140

Phe Glu Ala Arg Val Ala Asp Phe Gly Val Ala Lys Leu Ile Gln Thr
145                 150                 155                 160

Asp Glu Ser Met Ser Val Ala Gly Ser Tyr Gly Tyr Ile Ala Pro
                165                 170                 175

Glu Tyr Ala Tyr Thr Leu Gln Val Asp Lys Lys Ser Asp Ile Tyr Ser
            180                 185                 190

Tyr Gly Val Ile Leu Leu Glu Ile Ile Thr Gly Lys Arg Ser Val Glu
        195                 200                 205
```

Pro Glu Phe Gly Glu Gly Asn Ser Ile Val Asp Trp Val Arg Ser Lys
    210                 215                 220

Leu Lys Thr Lys Glu Asp Val Glu Val Leu Asp Lys Ser Met Gly
225             230                 235                 240

Arg Ser Cys Ser Leu Ile Arg Glu Glu Met Lys
            245                 250

<210> SEQ ID NO 18
<211> LENGTH: 287
<212> TYPE: PRT
<213> ORGANISM: Populus tremula x Populus tremuloides

<400> SEQUENCE: 18

Ile Lys Glu Ser Asn Ile Ile Gly Met Gly Ala Ile Gly Ile Val Tyr
1               5                   10                  15

Lys Ala Glu Val Met Arg Arg Pro Leu Leu Thr Val Ala Val Lys Lys
                20                  25                  30

Leu Trp Arg Ser Pro Ser Pro Gln Asn Asp Ile Glu Asp His His Gln
        35                  40                  45

Glu Glu Asp Glu Glu Asp Asp Ile Leu Arg Glu Val Asn Leu Leu Gly
    50                  55                  60

Gly Leu Arg His Arg Asn Ile Val Lys Ile Leu Gly Tyr Val His Asn
65                  70                  75                  80

Glu Arg Glu Val Met Met Val Tyr Glu Tyr Met Pro Asn Gly Asn Leu
                85                  90                  95

Gly Thr Ala Leu His Ser Lys Asp Glu Lys Phe Leu Leu Arg Asp Trp
            100                 105                 110

Leu Ser Arg Tyr Asn Val Ala Val Gly Val Val Gln Gly Leu Asn Tyr
        115                 120                 125

Leu His Asn Asp Cys Tyr Pro Pro Ile Ile His Arg Asp Ile Lys Ser
    130                 135                 140

Asn Asn Ile Leu Leu Asp Ser Asn Leu Glu Ala Arg Ile Ala Asp Phe
145                 150                 155                 160

Gly Leu Ala Lys Met Met Leu His Lys Asn Glu Thr Val Ser Met Val
                165                 170                 175

Ala Gly Ser Tyr Gly Tyr Ile Ala Pro Glu Tyr Gly Tyr Thr Leu Lys
            180                 185                 190

Ile Asp Glu Lys Ser Asp Ile Tyr Ser Leu Gly Val Val Leu Leu Glu
        195                 200                 205

Leu Val Thr Gly Lys Met Pro Ile Asp Pro Ser Phe Glu Asp Ser Ile
    210                 215                 220

Asp Val Val Glu Trp Ile Arg Arg Lys Val Lys Lys Asn Glu Ser Leu
225                 230                 235                 240

Glu Glu Val Ile Asp Ala Ser Ile Ala Gly Asp Cys Lys His Val Ile
                245                 250                 255

Glu Glu Met Leu Leu Ala Leu Arg Ile Ala Leu Leu Cys Thr Ala Lys
            260                 265                 270

Leu Pro Lys Asp Arg Pro Ser Ile Arg Asp Val Ile Thr Met Leu
        275                 280                 285

<210> SEQ ID NO 19
<211> LENGTH: 276
<212> TYPE: PRT
<213> ORGANISM: Populus tremula x Populus tremuloides

<400> SEQUENCE: 19

```
Lys Glu Ser Asn Met Ile Gly Met Gly Ala Thr Gly Ile Val Tyr Lys
1               5                   10                  15

Ala Glu Met Ser Arg Ser Ser Thr Val Leu Ala Val Lys Lys Leu Trp
            20                  25                  30

Arg Ser Ala Ala Asp Ile Glu Asp Gly Thr Thr Gly Asp Phe Val Gly
        35                  40                  45

Glu Val Asn Leu Leu Gly Lys Leu Arg His Arg Asn Ile Val Arg Leu
    50                  55                  60

Leu Gly Phe Leu Tyr Asn Asp Lys Asn Met Met Ile Val Tyr Glu Phe
65                  70                  75                  80

Met Leu Asn Gly Asn Leu Gly Asp Ala Ile His Gly Lys Asn Ala Ala
                85                  90                  95

Gly Arg Leu Leu Val Asp Trp Val Ser Arg Tyr Asn Ile Ala Leu Gly
            100                 105                 110

Val Ala His Gly Leu Tyr Leu His His Asp Cys His Pro Pro Val Ile
        115                 120                 125

His Arg Asp Ile Lys Ser Asn Asn Ile Leu Leu Asp Ala Asn Leu Asp
    130                 135                 140

Ala Arg Ile Ala Asp Phe Gly Leu Ala Arg Met Met Ala Arg Lys Lys
145                 150                 155                 160

Glu Thr Val Ser Met Val Ala Gly Ser Tyr Gly Tyr Ile Ala Pro Glu
                165                 170                 175

Tyr Gly Tyr Thr Leu Lys Val Asp Glu Lys Ile Asp Ile Tyr Ser Tyr
            180                 185                 190

Gly Val Val Leu Leu Glu Leu Thr Gly Arg Arg Leu Glu Pro Glu
        195                 200                 205

Phe Gly Glu Ser Val Asp Ile Val Glu Trp Val Arg Arg Lys Ile Arg
210                 215                 220

Asp Asn Ile Ser Leu Glu Glu Ala Leu Asp Pro Asn Val Gly Asn Cys
225                 230                 235                 240

Arg Tyr Val Gln Glu Glu Met Leu Leu Val Leu Gln Ile Ala Leu Leu
                245                 250                 255

Cys Thr Thr Lys Leu Pro Lys Asp Arg Pro Ser Met Arg Asp Val Ile
            260                 265                 270

Ser Met Leu Gly
        275

<210> SEQ ID NO 20
<211> LENGTH: 308
<212> TYPE: PRT
<213> ORGANISM: Artificial Sequence
<220> FEATURE:
<223> OTHER INFORMATION: Consensus artificial amino acid sequence for
      PXY protein dervied from Arabidopsis thaliana.
<220> FEATURE:
<221> NAME/KEY: MISC_FEATURE
<222> LOCATION: (1)..(1)
<223> OTHER INFORMATION: Xaa can be any naturally occurring amino acid.
<220> FEATURE:
<221> NAME/KEY: MISC_FEATURE
<222> LOCATION: (23)..(26)
<223> OTHER INFORMATION: Xaa can be any naturally occurring amino acid.
<220> FEATURE:
<221> NAME/KEY: MISC_FEATURE
<222> LOCATION: (37)..(37)
<223> OTHER INFORMATION: Xaa can be any naturally occurring amino acid.
<220> FEATURE:
<221> NAME/KEY: MISC_FEATURE
<222> LOCATION: (39)..(48)
<223> OTHER INFORMATION: Xaa can be any naturally occurring amino acid.
```

```
<220> FEATURE:
<221> NAME/KEY: MISC_FEATURE
<222> LOCATION: (50)..(64)
<223> OTHER INFORMATION: Xaa can be any naturally occurring amino acid.
<220> FEATURE:
<221> NAME/KEY: MISC_FEATURE
<222> LOCATION: (71)..(71)
<223> OTHER INFORMATION: Xaa can be any naturally occurring amino acid.
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: MISC_FEATURE
<222> LOCATION: (91)..(93)
<223> OTHER INFORMATION: Xaa can be any naturally occurring amino acid.
<220> FEATURE:
<221> NAME/KEY: MISC_FEATURE
<222> LOCATION: (107)..(107)
<223> OTHER INFORMATION: Any amino acid.
<220> FEATURE:
<221> NAME/KEY: MISC_FEATURE
<222> LOCATION: (113)..(115)
<223> OTHER INFORMATION: Xaa can be any naturally occurring amino acid.
<220> FEATURE:
<221> NAME/KEY: MISC_FEATURE
<222> LOCATION: (117)..(117)
<223> OTHER INFORMATION: Xaa can be any naturally occurring amino acid.
<220> FEATURE:
<221> NAME/KEY: MISC_FEATURE
<222> LOCATION: (121)..(121)
<223> OTHER INFORMATION: Xaa can be any naturally occurring amino acid.
<220> FEATURE:
<221> NAME/KEY: MISC_FEATURE
<222> LOCATION: (145)..(145)
<223> OTHER INFORMATION: Xaa can be any naturally occurring amino acid.
<220> FEATURE:
<221> NAME/KEY: MISC_FEATURE
<222> LOCATION: (178)..(181)
<223> OTHER INFORMATION: Xaa can be any naturally occurring amino acid.
<220> FEATURE:
<221> NAME/KEY: MISC_FEATURE
<222> LOCATION: (243)..(243)
<223> OTHER INFORMATION: Any amino acid.
<220> FEATURE:
<221> NAME/KEY: MISC_FEATURE
<222> LOCATION: (247)..(248)
<223> OTHER INFORMATION: Xaa can be any naturally occurring amino acid.
<220> FEATURE:
<221> NAME/KEY: MISC_FEATURE
<222> LOCATION: (250)..(250)
<223> OTHER INFORMATION: Xaa can be any naturally occurring amino acid.
<220> FEATURE:
<221> NAME/KEY: MISC_FEATURE
<222> LOCATION: (252)..(252)
<223> OTHER INFORMATION: Xaa can be any naturally occurring amino acid.
<220> FEATURE:
<221> NAME/KEY: MISC_FEATURE
<222> LOCATION: (254)..(254)
<223> OTHER INFORMATION: Xaa can be any naturally occurring amino acid.
<220> FEATURE:
<221> NAME/KEY: MISC_FEATURE
<222> LOCATION: (257)..(257)
<223> OTHER INFORMATION: Xaa can be any naturally occurring amino acid.
<220> FEATURE:
<221> NAME/KEY: MISC_FEATURE
<222> LOCATION: (261)..(264)
<223> OTHER INFORMATION: Xaa can be any naturally occurring amino acid.
<220> FEATURE:
<221> NAME/KEY: MISC_FEATURE
<222> LOCATION: (266)..(266)
<223> OTHER INFORMATION: Xaa can be any naturally occurring amino acid.
<220> FEATURE:
<221> NAME/KEY: MISC_FEATURE
<222> LOCATION: (286)..(286)
<223> OTHER INFORMATION: Xaa can be any naturally occurring amino acid.
<220> FEATURE:
<221> NAME/KEY: MISC_FEATURE
<222> LOCATION: (301)..(301)
```

<223> OTHER INFORMATION: Xaa can be any naturally occurring amino acid.

<400> SEQUENCE: 20

Xaa Lys Glu Ala Asn Ile Val Gly Met Gly Ala Thr Gly Ile Val Tyr
1               5                   10                  15

Lys Ala Glu Met Pro Arg Xaa Xaa Xaa Xaa Val Ile Ala Val Lys Lys
            20                  25                  30

Leu Trp Arg Ala Xaa Ala Xaa Xaa Xaa Xaa Xaa Xaa Xaa Xaa Xaa Xaa
        35                  40                  45

Glu Xaa Xaa Xaa Xaa Xaa Xaa Xaa Xaa Xaa Xaa Xaa Xaa Xaa Xaa Xaa
50                  55                  60

Asp Val Leu Ala Glu Val Xaa Leu Leu Gly Xaa Leu Arg His Arg Asn
65                  70                  75                  80

Ile Val Arg Leu Leu Gly Tyr Val Ser Asn Xaa Xaa Xaa Thr Met Leu
                85                  90                  95

Leu Tyr Glu Tyr Met Pro Asn Gly Ser Leu Xaa Asp Ala Leu His Gly
            100                 105                 110

Xaa Xaa Xaa Ala Xaa Lys Leu Leu Xaa Asp Trp Val Ser Arg Tyr Asn
            115                 120                 125

Ile Ala Leu Gly Val Ala Gln Gly Leu Ala Tyr Leu His His Asp Cys
130                 135                 140

Xaa Pro Pro Ile Ile His Arg Asp Ile Lys Ser Ser Asn Ile Leu Leu
145                 150                 155                 160

Asp Ala Asn Met Glu Ala Arg Ile Ala Asp Phe Gly Leu Ala Lys Leu
                165                 170                 175

Met Xaa Xaa Xaa Glu Ser Val Ser Val Val Ala Gly Ser Tyr Gly
            180                 185                 190

Tyr Ile Ala Pro Glu Tyr Gly Tyr Thr Leu Lys Val Asp Glu Lys Ser
            195                 200                 205

Asp Ile Tyr Ser Tyr Gly Val Val Leu Leu Glu Leu Ile Thr Gly Arg
210                 215                 220

Arg Ser Val Glu Pro Glu Phe Gly Glu Gly Asn Asp Ile Val Asp Trp
225                 230                 235                 240

Val Arg Xaa Lys Ile Lys Xaa Xaa Asn Xaa Val Xaa Glu Xaa Leu Asp
                245                 250                 255

Xaa Ala Ala Val Ala Xaa Xaa Xaa Cys Xaa His Val Arg Glu Glu Met
            260                 265                 270

Leu Leu Val Leu Arg Ile Ala Leu Leu Cys Thr Ala Lys Xaa Pro Lys
            275                 280                 285

Asp Arg Pro Ser Met Arg Asp Val Ile Thr Met Leu Xaa Glu Ala Lys
            290                 295                 300

Pro Lys Arg Lys
305

<210> SEQ ID NO 21
<211> LENGTH: 99
<212> TYPE: PRT
<213> ORGANISM: Arabidopsis thaliana

<400> SEQUENCE: 21

Met Ala Thr Ser Asn Asp Gln Thr Asn Thr Lys Ser Ser His Ser Arg
1               5                   10                  15

Thr Leu Leu Leu Leu Phe Ile Phe Leu Ser Leu Leu Leu Phe Ser Ser
            20                  25                  30

Leu Thr Ile Pro Met Thr Arg His Gln Ser Thr Ser Met Val Ala Pro

```
                35                  40                  45
Phe Lys Arg Val Leu Leu Glu Ser Ser Val Pro Ala Ser Ser Thr Met
 50                  55                  60

Asp Leu Arg Pro Lys Ala Ser Thr Arg Ser Arg Thr Ser Arg Arg
 65                  70                  75                  80

Arg Glu Phe Gly Asn Asp Ala His Glu Val Pro Ser Gly Pro Asn Pro
                 85                  90                  95

Ile Ser Asn

<210> SEQ ID NO 22
<211> LENGTH: 300
<212> TYPE: DNA
<213> ORGANISM: Arabidopsis thaliana

<400> SEQUENCE: 22
atggcaacat caaatgacca aaccaatact aaatcatcac attctcgtac tcttctcctt       60
ctcttcatct tcttatccct ccttctcttc agtagcctta caatcccat gactcgtcat      120 cagtccacat ctatggttgc tcccttcaag agggttctcc tcgaatcttc agttccagct      180
tcatcaacaa tggatctacg tccaaaggct agcacacgac gcagccgcac ttctagaagg      240
agagagtttg gaaatgatgc tcatgaggtt cctagtggtc caaaccctat ttccaactag      300

<210> SEQ ID NO 23
<211> LENGTH: 88
<212> TYPE: PRT
<213> ORGANISM: Arabidopsis thaliana

<400> SEQUENCE: 23

Met Arg Ser Pro His Ile Thr Ile Ser Leu Val Phe Leu Phe Phe Leu
 1               5                  10                  15

Phe Leu Ile Ile Gln Thr His Gln Arg Thr Ile Asp Gln Thr His Gln
                 20                  25                  30

Ile Gly Ser Asn Val Gln His Val Ser Asp Met Ala Val Thr Ser Pro
             35                  40                  45

Glu Gly Lys Arg Arg Glu Arg Phe Arg Val Arg Pro Met Thr Thr
 50                  55                  60

Trp Leu Lys Gly Lys Met Ile Gly Ala Asn Glu His Gly Val Pro Ser
 65                  70                  75                  80

Gly Pro Asn Pro Ile Ser Asn Arg
                 85

<210> SEQ ID NO 24
<211> LENGTH: 267
<212> TYPE: DNA
<213> ORGANISM: Arabidopsis thaliana

<400> SEQUENCE: 24
atgagatctc ctcacatcac catttcactt gttttcttgt tctttctttt tctaatcatc       60
caaacccatc aaagaaccat tgatcaaact caccagattg gctccaatgt tcaacatgtc      120
agtgacatgg cggtgacttc gcctgaaggg aaaagaagag agaggtttag agttcggcgg      180
ccgatgacga catggctgaa gggaaagatg atcggtgcca atgaacatgg agtcccaagt      240
ggtccaaatc ccatctccaa taggtag                                          267

<210> SEQ ID NO 25
<211> LENGTH: 1041
<212> TYPE: PRT
```

<213> ORGANISM: Arabidopsis thaliana

<400> SEQUENCE: 25

```
Met Lys Lys Lys Asn Ile Ser Pro Ser Leu Val Leu His Pro Leu Leu
1               5                   10                  15
Leu Leu Leu Leu Pro Phe Phe Ala Phe Asn Ser Leu Ala Leu Lys Phe
            20                  25                  30
Ser Pro Gln Leu Leu Ser Leu Leu Ser Leu Lys Thr Ser Leu Ser Gly
        35                  40                  45
Pro Pro Ser Ala Phe Gln Asp Trp Lys Val Pro Val Asn Gly Gln Asn
    50                  55                  60
Asp Ala Val Trp Cys Ser Trp Ser Gly Val Val Cys Asp Asn Val Thr
65                  70                  75                  80
Ala Gln Val Ile Ser Leu Asp Leu Ser His Arg Asn Leu Ser Gly Arg
                85                  90                  95
Ile Pro Ile Gln Ile Arg Tyr Leu Ser Leu Leu Tyr Leu Asn Leu
            100                 105                 110
Ser Gly Asn Ser Leu Glu Gly Ser Phe Pro Thr Ser Ile Phe Asp Leu
        115                 120                 125
Thr Lys Leu Thr Thr Leu Asp Ile Ser Arg Asn Ser Phe Asp Ser Ser
130                 135                 140
Phe Pro Pro Gly Ile Ser Lys Leu Lys Phe Leu Lys Val Phe Asn Ala
145                 150                 155                 160
Phe Ser Asn Asn Phe Glu Gly Leu Leu Pro Ser Asp Val Ser Arg Leu
                165                 170                 175
Arg Phe Leu Glu Glu Leu Asn Phe Gly Gly Ser Tyr Phe Glu Gly Glu
            180                 185                 190
Ile Pro Ala Ala Tyr Gly Gly Leu Gln Arg Leu Lys Phe Ile His Leu
        195                 200                 205
Ala Gly Asn Val Leu Gly Gly Lys Leu Pro Pro Arg Leu Gly Leu Leu
    210                 215                 220
Thr Glu Leu Gln His Met Glu Ile Gly Tyr Asn His Phe Asn Gly Asn
225                 230                 235                 240
Ile Pro Ser Glu Phe Ala Leu Leu Ser Asn Leu Lys Tyr Phe Asp Val
                245                 250                 255
Ser Asn Cys Ser Leu Ser Gly Ser Leu Pro Gln Glu Leu Gly Asn Leu
            260                 265                 270
Ser Asn Leu Glu Thr Leu Phe Leu Phe Gln Asn Gly Phe Thr Gly Glu
        275                 280                 285
Ile Pro Glu Ser Tyr Ser Asn Leu Lys Ser Leu Lys Leu Leu Asp Phe
    290                 295                 300
Ser Ser Asn Gln Leu Ser Gly Ser Ile Pro Ser Gly Phe Ser Thr Leu
305                 310                 315                 320
Lys Asn Leu Thr Trp Leu Ser Leu Ile Ser Asn Asn Leu Ser Gly Glu
                325                 330                 335
Val Pro Glu Gly Ile Gly Glu Leu Pro Glu Leu Thr Thr Leu Phe Leu
            340                 345                 350
Trp Asn Asn Asn Phe Thr Gly Val Leu Pro His Lys Leu Gly Ser Asn
        355                 360                 365
Gly Lys Leu Glu Thr Met Asp Val Ser Asn Asn Ser Phe Thr Gly Thr
    370                 375                 380
Ile Pro Ser Ser Leu Cys His Gly Asn Lys Leu Tyr Lys Leu Ile Leu
385                 390                 395                 400
```

```
Phe Ser Asn Met Phe Glu Gly Glu Leu Pro Lys Ser Leu Thr Arg Cys
                405                 410                 415

Glu Ser Leu Trp Arg Phe Arg Ser Gln Asn Asn Arg Leu Asn Gly Thr
            420                 425                 430

Ile Pro Ile Gly Phe Gly Ser Leu Arg Asn Leu Thr Phe Val Asp Leu
        435                 440                 445

Ser Asn Asn Arg Phe Thr Asp Gln Ile Pro Ala Asp Phe Ala Thr Ala
450                 455                 460

Pro Val Leu Gln Tyr Leu Asn Leu Ser Thr Asn Phe Phe His Arg Lys
465                 470                 475                 480

Leu Pro Glu Asn Ile Trp Lys Ala Pro Asn Leu Gln Ile Phe Ser Ala
            485                 490                 495

Ser Phe Ser Asn Leu Ile Gly Glu Ile Pro Asn Tyr Val Gly Cys Lys
            500                 505                 510

Ser Phe Tyr Arg Ile Glu Leu Gln Gly Asn Ser Leu Asn Gly Thr Ile
            515                 520                 525

Pro Trp Asp Ile Gly His Cys Glu Lys Leu Leu Cys Leu Asn Leu Ser
        530                 535                 540

Gln Asn His Leu Asn Gly Ile Ile Pro Trp Glu Ile Ser Thr Leu Pro
545                 550                 555                 560

Ser Ile Ala Asp Val Asp Leu Ser His Asn Leu Leu Thr Gly Thr Ile
            565                 570                 575

Pro Ser Asp Phe Gly Ser Ser Lys Thr Ile Thr Thr Phe Asn Val Ser
            580                 585                 590

Tyr Asn Gln Leu Ile Gly Pro Ile Pro Ser Gly Ser Phe Ala His Leu
        595                 600                 605

Asn Pro Ser Phe Phe Ser Ser Asn Glu Gly Leu Cys Gly Asp Leu Val
610                 615                 620

Gly Lys Pro Cys Asn Ser Asp Arg Phe Asn Ala Gly Asn Ala Asp Ile
625                 630                 635                 640

Asp Gly His His Lys Glu Glu Arg Pro Lys Lys Thr Ala Gly Ala Ile
            645                 650                 655

Val Trp Ile Leu Ala Ala Ala Ile Gly Val Gly Phe Phe Val Leu Val
        660                 665                 670

Ala Ala Thr Arg Cys Phe Gln Lys Ser Tyr Gly Asn Arg Val Asp Gly
        675                 680                 685

Gly Gly Arg Asn Gly Gly Asp Ile Gly Pro Trp Lys Leu Thr Ala Phe
    690                 695                 700

Gln Arg Leu Asn Phe Thr Ala Asp Asp Val Val Glu Cys Leu Ser Lys
705                 710                 715                 720

Thr Asp Asn Ile Leu Gly Met Gly Ser Thr Gly Thr Val Tyr Lys Ala
                725                 730                 735

Glu Met Pro Asn Gly Glu Ile Ile Ala Val Lys Lys Leu Trp Gly Lys
            740                 745                 750

Asn Lys Glu Asn Gly Lys Ile Arg Arg Lys Ser Gly Val Leu Ala
            755                 760                 765

Glu Val Asp Val Leu Gly Asn Val Arg His Arg Asn Ile Val Arg Leu
    770                 775                 780

Leu Gly Cys Cys Thr Asn Arg Asp Cys Thr Met Leu Leu Tyr Glu Tyr
785                 790                 795                 800

Met Pro Asn Gly Ser Leu Asp Asp Leu Leu His Gly Gly Asp Lys Thr
                805                 810                 815

Met Thr Ala Ala Ala Glu Trp Thr Ala Leu Tyr Gln Ile Ala Ile Gly
```

```
             820             825             830
Val Ala Gln Gly Ile Cys Tyr Leu His His Asp Cys Asp Pro Val Ile
                835             840             845
Val His Arg Asp Leu Lys Pro Ser Asn Ile Leu Leu Asp Ala Asp Phe
    850             855             860
Glu Ala Arg Val Ala Asp Phe Gly Val Ala Lys Leu Ile Gln Thr Asp
865             870             875             880
Glu Ser Met Ser Val Val Ala Gly Ser Tyr Gly Tyr Ile Ala Pro Glu
                885             890             895
Tyr Ala Tyr Thr Leu Gln Val Asp Lys Lys Ser Asp Ile Tyr Ser Tyr
            900             905             910
Gly Val Ile Leu Leu Glu Ile Ile Thr Gly Lys Arg Ser Val Glu Pro
            915             920             925
Glu Phe Gly Glu Gly Asn Ser Ile Val Asp Trp Val Arg Ser Lys Leu
        930             935             940
Lys Thr Lys Glu Asp Val Glu Glu Val Leu Asp Lys Ser Met Gly Arg
945             950             955             960
Ser Cys Ser Leu Ile Arg Glu Glu Met Lys Gln Met Leu Arg Ile Ala
                965             970             975
Leu Leu Cys Thr Ser Arg Ser Pro Thr Asp Arg Pro Pro Met Arg Asp
            980             985             990
Val Leu Leu Ile Leu Gln Glu Ala  Lys Pro Lys Arg Lys  Thr Val Gly
            995             1000            1005
Asp Asn  Val Ile Val Val Gly  Asp Val Asn Asp Val  Asn Phe Glu
    1010            1015            1020
Asp Val  Cys Ser Val Asp Val  Gly His Asp Val Lys  Cys Gln Arg
    1025            1030            1035
Ile Gly  Val
    1040

<210> SEQ ID NO 26
<211> LENGTH: 3126
<212> TYPE: DNA
<213> ORGANISM: Arabidopsis thaliana

<400> SEQUENCE: 26
atgaaaaaga agaacatttc tccttctctt gttcttcatc cccttctcct tcttctactt      60 ccttctttg  ctttcaattc cttagctctc aagttttcac ctcaactctt gtctctcctt     120
tcccttaaaa catctctctc tggccctccc tctgcctttc aagactggaa agtcccccgtt    180 aacggtcaaa cgacgccgt  ttggtgttct tggtccggtg tagtctgtga taatgtaacg     240
gctcaagtca tttccctcga cctctctcac cggaacctct ctggtcgtat tcctatacag     300
attcgttact tgtcgagctt actctactta aatctcagtg ggaattcttt ggaaggttcg     360
tttccaactt ctatctttga tctcaccaag ctcactaccc tcgacatcag ccgtaactcg     420
ttcgactcga gttttcctcc cggaatctcc aagcttaagt tcttaaaagt cttcaatgcg     480
ttcagcaaca acttcgaagg tctattacct agtgacgtgt ctcgtcttcg tttcttggaa     540
gagcttaact ttggtggaag ttactttgaa ggagagattc cagcagctta cggtggttta     600
cagagattga agtttattca tttagctgga aatgtcctcg gaggtaaact acctcctaga     660
ttaggactct taacagagct ccaacacatg gaaatcggtt ataatcactt caacggaaac     720
ataccttcgg agtttgcctt actctcaaat ctcaagtact tgacgtttc  caattgcagc     780 ctctctggtt ctctgcctca agaactcggg aatctctcaa acctagagac tttatttcta     840
```

```
ttccaaaacg gtttcaccgg tgaaatccca gagagttata gcaacttgaa atccctcaag    900
cttctcgatt tttcgagtaa tcagctttct ggtagtatcc catcaggctt ctcgaccttg    960
aagaacctca catggctaag cttaatcagc aataacctct caggtgaagt acctgaagga   1020
atcggtgaac tccctgagct tactacattg tttctatgga acaataactt caccggagtt   1080
ttgccacaca agcttggatc aaacggtaaa cttgagacaa tggacgtctc taacaattca   1140
ttcaccggaa caatcccttc ttctctctgc catggaaaca agctatacaa actcatcctc   1200
ttctccaaca tgtttgaagg tgagctacca aagagcttga ctcgttgcga atctctatgg   1260
cggtttcgga gtcaaaacaa tcgattaaac ggcacaattc cgatcggatt cggctctcta   1320
cgtaacctca ctttcgttga tttaagcaac aacagattca ccgatcaaat tccggcggat   1380
ttcgccaccg ctcctgttct tcagtacttg aatctctcaa ccaatttctt ccacaggaaa   1440
ctaccggaaa acatatggaa agctccgaat ctacagatct tctcagcgag tttcagcaat   1500
ttgatcggtg aaatcccaaa ttacgttgga tgcaaaagct tctacaggat tgaactacaa   1560
ggaaactcac tcaacggaac gattccatgg gacatcggac attgcgagaa gcttctctgt   1620
ttgaatctca gccaaaatca tctcaacgga atcattccat gggagatttc aactcttccg   1680
tcaatcgccg acgtagatct ttctcataat ctcttaaccg gaacaatccc ttccgatttc   1740
ggaagctcta agacgatcac aaccttcaac gtttcgtata atcagctaat cggtccgatt   1800
ccaagtggtt ctttcgctca tctgaatccg tcgttcttct cctcaaacga aggactctgt   1860
ggagatctcg tcggaaaacc ttgcaattct gataggttta acgccggaaa tgcagatata   1920
gacggtcatc ataaagagga acgacctaag aaaacagccg gagctattgt ttggatattg   1980
gcggcggcga ttggggttgg attcttcgtc cttgtagccg ccactagatg cttccagaaa   2040
agctacggaa acagagtcga cggtggtgga agaaacggcg gagatatagg accgtggaag   2100
ctaacggctt ttcagagact aaacttcacg gcggatgatg tggttgagtg tctctcaaag   2160
actgataaca tcctcggaat gggatcaaca ggaacagtgt acaaagcaga gatgcctaat   2220
ggagaaataa tcgccgtgaa aaaactttgg ggaaaaaaca aagagaacgg caaaatccgg   2280
cggcggaaga gcggcgtatt ggcggaggtt gatgttctag ggaacgtacg tcaccggaac   2340
atcgttcgtc tccttggatg ttgcacgaat cgagattgca cgatgctttt atacgaatac   2400
atgcctaatg gaagcttaga cgatcttctt cacggtgggg ataagacgat gaccgcggcg   2460
gcggaatgga cggctttgta tcagatcgcg attggagtgg ctcaagggat ctgttatctc   2520
caccatgatt gtgatccggt gattgtacac cgtgacctga aacctagcaa tatcctcctc   2580
gacgccgatt tcgaggcgcg tgtggcggac ttcgcgtcg cgaagcttat tcaaaccgac   2640
gaatccatgt ccgtcgtcgc cggttcgtac ggttacattg caccagaata tgcttacact   2700
ttacaagtgg ataaaagag tgatatctat agctatggag tgattttatt agagataatc   2760
accggaaaaa gatcggtgga accggaattt ggagaaggta acagtatcgt ggattgggtt   2820
agatcaaagt tgaagacgaa agaagatgta gaagaagttc tagacaaaag catgggtagg   2880
tcgtgtagtc ttataagaga agagatgaaa caaatgttga gaattgcgtt gttgtgtaca   2940
agccggagtc cgacagacag accgccgatg agagatgtgt tgttgattct tcaagaggca   3000
aagccaaaga ggaagacagt aggggataat gtgatcgtcg ttggtgatgt taatgatgtc   3060
aatttcgaag atgtttgtag tgttgatgtt ggtcatgatg ttaaatgtca aaggattggg   3120
gtgtga                                                              3126
```

<210> SEQ ID NO 27
<211> LENGTH: 3302
<212> TYPE: DNA
<213> ORGANISM: Arabidopsis thaliana

<400> SEQUENCE: 27

| | | | | | | |
|---|---|---|---|---|---|---|
| atgaaaaaga | agaacatttc | tccttctctt | gttcttcatc | cccttctcct | tcttctactt | 60 |
| cctttctttg | ctttcaattc | cttagctctc | aagttttcac | ctcaactctt | gtctctcctt | 120 |
| tcccttaaaa | catctctctc | tggccctccc | tctgcctttc | aagactggaa | agtcccgtt | 180 |
| aacggtcaaa | acgacgccgt | ttggtgttct | tggtccggtg | tagtctgtga | taatgtaacg | 240 |
| gctcaagtca | tttccctcga | cctctctcac | cggaacctct | ctggtcgtat | tcctatacag | 300 |
| attcgttact | tgtcgagctt | actctactta | aatctcagtg | ggaattcttt | ggaaggttcg | 360 |
| tttccaactt | ctatctttga | tctcaccaag | ctcactaccc | tcgacatcag | ccgtaactcg | 420 |
| ttcgactcga | gttttcctcc | cggaatctcc | aagcttaagt | tcttaaaagt | cttcaatgcg | 480 |
| ttcagcaaca | acttcgaagg | tctattacct | agtgacgtgt | ctcgtcttcg | tttcttggaa | 540 |
| gagcttaact | ttggtggaag | ttactttgaa | ggagagattc | cagcagctta | cggtggttta | 600 |
| cagagattga | agtttattca | tttagctgga | atgtcctcg | gaggtaaact | acctcctaga | 660 |
| ttaggactct | taacagagct | ccaacacatg | gaaatcggtt | ataatcactt | caacggaaac | 720 |
| ataccttcgg | agtttgcctt | actctcaaat | ctcaagtact | tgacgtttc | caattgcagc | 780 |
| ctctctggtt | ctctgcctca | agaactcggg | aatctctcaa | acctagagac | tttatttcta | 840 |
| ttccaaaacg | gtttcaccgg | tgaaatccca | gagagttata | gcaacttgaa | atccctcaag | 900 |
| cttctcgatt | tttcgagtaa | tcagctttct | ggtagtatcc | catcaggctt | ctcgaccttg | 960 |
| aagaacctca | catggctaag | cttaatcagc | aataacctct | caggtgaagt | acctgaagga | 1020 |
| atcggtgaac | tccctgagct | tactacattg | tttctatgga | acaataactt | caccggagtt | 1080 |
| ttgccacaca | agcttggatc | aaacggtaaa | cttgagacaa | tggacgtctc | taacaattca | 1140 |
| ttcaccggaa | caatcccttc | ttctctctgc | catggaaaca | agctatacaa | actcatcctc | 1200 |
| ttctccaaca | tgtttgaagg | tgagctacca | aagagcttga | ctcgttgcga | atctctatgg | 1260 |
| cggtttcgga | gtcaaaacaa | tcgattaaac | ggcacaattc | cgatcggatt | cggctctcta | 1320 |
| cgtaacctca | ctttcgttga | tttaagcaac | aacagattca | ccgatcaaat | tccggcggat | 1380 |
| ttcgccaccg | ctcctgttct | tcagtacttg | aatctctcaa | ccaatttctt | ccacaggaaa | 1440 |
| ctaccggaaa | acatatggaa | agctccgaat | ctacagatct | tctcagcgag | tttcagcaat | 1500 |
| ttgatcggtg | aaatcccaaa | ttacgttgga | tgcaaaagct | tctacaggat | tgaactacaa | 1560 |
| ggaaactcac | tcaacggaac | gattccatgg | gacatcggac | attgcgagaa | gcttctctgt | 1620 |
| ttgaatctca | gccaaaatca | tctcaacgga | atcattccat | gggagatttc | aactcttccg | 1680 |
| tcaatcgccg | acgtagatct | ttctcataat | ctcttaaccg | gaacaatccc | ttccgatttc | 1740 |
| ggaagctcta | agacgatcac | aaccttcaac | gtttcgtata | tcagctaat | cggtccgatt | 1800 |
| ccaagtggtt | ctttcgctca | tctgaatccg | tcgttcttct | cctcaaacga | aggactctgt | 1860 |
| ggagatctcg | tcggaaaacc | ttgcaattct | gataggttta | acgccggaaa | tgcagatata | 1920 |
| gacggtcatc | ataaagagga | acgacctaag | aaaacagccg | gagctattgt | ttggatattg | 1980 |
| gcggcggcga | ttggggttgg | attcttcgtc | cttgtagccg | ccactagatg | cttccagaaa | 2040 |
| agctacggaa | acagagtcga | cggtggtgga | agaaacggcg | gagatatagg | accgtggaag | 2100 |
| ctaacggctt | ttcagagact | aaacttcacg | gcggatgatg | tggttgagtg | tctctcaaag | 2160 |

```
actgataaca tcctcggaat gggatcaaca ggaacagtgt acaaagcaga gatgcctaat    2220
ggagaaataa tcgccgtgaa aaactttgg ggaaaaaaca aagagaacgg caaaatccgg     2280
cggcggaaga gcggcgtatt ggcggaggtt gatgttctag gaacgtacg tcaccggaac     2340 atcgttcgtc tccttggatg ttgcacgaat cgagattgca cgatgctttt atacgaatac    2400
atgcctaatg gaagcttaga cgatcttctt cacggtgggg ataagacgat gaccgcggcg    2460
gcggaatgga cggctttgta tcagatcgcg attggagtgg ctcaagggat ctgttatctc    2520
caccatgatt gtgatccggt gattgtacac cgtgacctga aacctagcaa tatcctcctc    2580
gacgccgatt cgaggcgcg tgtggcggac ttcggcgtcg cgaagcttat tcaaaccgac     2640
gaatccatgt ccgtcgtcgc cggttcgtac ggttacattg caccaggtac ccttaacttt    2700
ttttgattat tctttacttt ccccaaattt taaattttgt actttttttgt cccttttgttt   2760 ttattattcg aattttgtcc gtttgttaaa cattcttttt gttgggatga caacatctga    2820
caaatatgac taaaattta attttgtttg ttttggttac agaatatgct tacactttac     2880
aagtggataa aaagagtgat atctatagct atggagtgat tttattagag ataatcaccg    2940
gaaaaagatc ggtggaaccg gaatttggag aaggtaacag tatcgtggat tgggttagat    3000
caaagttgaa gacgaaagaa gatgtagaag aagttctaga caaaagcatg ggtaggtcgt    3060
gtagtcttat aagagaagag atgaaacaaa tgttgagaat tgcgttgttg tgtacaagcc    3120
ggagtccgac agacagaccg ccgatgagag atgtgttgtt gattcttcaa gaggcaaagc    3180
caaagaggaa gacagtaggg gataatgtga tcgtcgttgg tgatgttaat gatgtcaatt    3240
tcgaagatgt ttgtagtgtt gatgttggtc atgatgttaa atgtcaaagg attggggtgt    3300
ga                                                                  3302

<210> SEQ ID NO 28
<211> LENGTH: 345
<212> TYPE: DNA
<213> ORGANISM: Cauliflower mosaic virus

<400> SEQUENCE: 28
tgagactttt caacaaaggg taatatccgg aaacctcctc ggattccatt gcccagctat     60
ctgtcacttt attgtgaaga tagtggaaaa ggaaggtggc tcctacaaat gccatcattg    120
cgataaagga aaggccatcg ttgaagatgc ctctgccgac agtggtccca agatggacc     180 cccacccac gaggagcatc gtggaaaaag aagacgttcc aaccacgtct caaagcaag     240 tggattgatg tgatatctcc actgacgtaa gggatgacgc acaatcccac tatccttcgc    300
aagacccttc ctctatataa ggaagttcat ttcatttgga gagga                    345

<210> SEQ ID NO 29
<211> LENGTH: 1122
<212> TYPE: DNA
<213> ORGANISM: Arabidopsis thaliana

<400> SEQUENCE: 29
aaaaataagt aaaagatctt ttagttgttt gctttgtatg ttgcgaacag tttgattctg     60 ttttctttt tccttttttt gggtaatttt cttataactt ttttcatagt ttcgattatt     120
tggataaaat tttcagattg aggatcattt tatttattta ttagtgtagt ctaatttagt    180
tgtataacta taaattgtt gtttgtttcc gaatcataag ttttttttttt ttttggtttt    240 gtattgatag gtgcaagaga ctcaaaattc tggtttcgat gttaacagaa ttcaagtagc    300
```

| | |
|---|---|
| tgcccacttg attcgatttg ttttgtattt ggaaacaacc atggctggtc aaggcccagc | 360 |
| ccgttgtgct tctgaacctg cctagtccca tggactagta ctttatccgc agactccaaa | 420 |
| agaaaaagga ttggcgcaga ggaattgtca tggaaacaga atgaacaaga aagggtgaag | 480 |
| aagatcaaag gcatatatga tctttacatt ctctttagct tatgtatgca gaaaattcac | 540 |
| ctaattaagg acagggaacg taacttggct tgcactcctc tcaccaaacc ttaccccta | 600 |
| actaattta attcaaaatt actagtattt tggccgatca ctttatataa taagatacca | 660 |
| gatttattat atttacgaat tatcagcatg catatactgt atatagtttt tttttttgtta | 720 |
| aagggtaaaa taataggatc cttttgaata aaatgaacat atataattag tataatgaaa | 780 |
| acagaaggaa atgagattag gacagtaagt aaaatgagag agacctgcaa aggataaaaa | 840 |
| agagaagctt aaggaaaccg cgacgatgaa agaaagacat gtcatcagct gatggatgtg | 900 |
| agtgatgagt ttgttgcagt tgtgtagaaa tttttactaa aacagttgtt tttacaaaaa | 960 |
| agaaataata taaaacgaaa gcttagcttg aaggcaatgg agactctaca acaaactatg | 1020 |
| taccatacag agagagaaac taaaagcttt tcacacataa aaaccaaact tattcgtctc | 1080 |
| tcattgatca ccgttttgtt ctctcaagat cgctgctaat ct | 1122 |

<210> SEQ ID NO 30
<211> LENGTH: 1569
<212> TYPE: DNA
<213> ORGANISM: Arabidopsis thaliana

<400> SEQUENCE: 30

| | |
|---|---|
| gtgttttttgg acataatgat ttgaatgata ttaaacaaaa aaaaggcatc ttattgtaat | 60 |
| taaattaata aagtaatgga cgttttttgtt agtgagacgc ctgaacttgt catgacatac | 120 |
| agacatacca attccattca tgcaggagaa tgttgaataa tgtgagggaa cgtgaataga | 180 |
| ggaactattt ttgggtaaat gcaatcacat cctctcattc tcaaacctcc aaaccaaaat | 240 |
| gtgtagttt cttcctctcc aagaaacaat actcttatga ctgcaatacc acactttagt | 300 |
| ctgtgtgtgt ttttttaatag aatggtataa agaagcatac tgaaatggtg ttttttaaatg | 360 |
| aaagatcaaa tcacaacaat atccaaaacc taaaataaaa agattgtggg cttatttatt | 420 |
| aggcccatag tctttattct ttaagggcaa actttcagag atgcgggtct acattatttg | 480 |
| gcccgaacca gtaaaacctg caggcttcta gagaaaccca tacgaatggc gagttaccgg | 540 |
| tcagaagcgt aatcaccggt ccttaaattt catttccagg cgaacgattt ggaaaagtcg | 600 |
| gtgtcgttaa gaaaagacaa ttcctacccct ttttgtcgtc atttgttttgc taattgctac | 660 |
| ctttataatg taagggagga gtggagttgc tattattatt ccgacattta agtgttatgt | 720 |
| gtttgtcgga tcggattcta tcttaagaat cttatcttat tccccccgaa tatcattgac | 780 |
| tttgtcttaa atcttaattt gttatgtttg cacttaaact ctctctttt cgttagtgca | 840 |
| cacaactcgt attccatcaa aatcaatgat aaaataattc ttaccaaatt aacaaaaagt | 900 |
| gaataaatat cacattattc atactaatct tcatgatatc atcacaagaa taatgtgtgc | 960 |
| acacaaaaaa ccactgtttg tttccgcgtg aagtgaactc tcaagagtct ccaatgttga | 1020 |
| ccaaatcaaa caacctctta acttctttga ccaacaattt ttaaaaccat gaaataagtt | 1080 |
| acatacgaag acttgacttg tttctttctc ttaaaaatca aagtttaact gcttcagagt | 1140 |
| ttaattttca atgtgtccat atacaattca tttttaaatct aaagcaaatt cctcttcttt | 1200 |
| tttttccttt aatttatttt attttttatg gagtgagttg agttctgtat acattctttg | 1260 |
| taaatggaaa aaaataaaaa aacagcttga ttaaaaaaaa taaagaaatt gagaaaaaga | 1320 |

```
caagaattta aataataata aaataatgta aaagaaagt gaacaacaaa aaagacaca      1380 aaaaagtaaa actgaaaagg agtatttctc tgtcatttcc cacaccaatc gcataatcga     1440
tttcttccaa cttcaataaa ggggaaccaa cgtaaccta atttttgcttt ctcctctttg     1500 ttcagaaaat tttccttta ctctcaaatt ccttttcgat ttccctctct taaacctccg     1560
aaagctcac                                                              1569
```

<210> SEQ ID NO 31
<211> LENGTH: 1000
<212> TYPE: DNA
<213> ORGANISM: Artificial Sequence
<220> FEATURE:
<223> OTHER INFORMATION: Synthetic Vector promoter DNA derived from synthetic construct.

<400> SEQUENCE: 31

```
gagggttgtc atgtcagcta aacagcagaa aaataaaaga atgtgggaga caggctttgc       60 cctttacac attttttaagc tctcttcttt attttctaaa aacactatag tacacagtta      120
aaaatttgcg ggcccttttgt ttaatcgatt tagatttaac caacagcttc atagtcgttt      180
cttcttgtta gaaatcaata aatgaaaagt tggttgtttt gaaagcatat aattaactaa      240
caatgtatca tgttgtgaaa caaaagctga tgataaatgt taaatatagt gtccaaaatt      300
ttgggaatgt cttcaaattt tgattttaaa acatatgaga tgtaccaaca tccacaaaat      360
gtttgtgaag ttgtgactta gtgagacgtt gtcactttat tatctcgttt tggtaacggt      420
aagtgcatgt gaacgtgttt gattataagt ttaacccgac tttgtttacg tggtcatagt      480
ttccaataag gctaagtaga atagtgtatg atagttttca attcaagagt cttttttttc      540
caagaaaatc cgaaaacaca atcgtttatt ttaatatctc aaaagaaatc atatttctta      600
ggtaaaacta tcatacgttg agttttctt tctccttttg cgattttccc tgaaatatat      660
ttatgttgtg tgtgtgcttt gtaaacaaaa taataatgaa cgtaataata gtaaaacaaa      720
aagtaaccta tattattatc atacttgata taacccaata gagaaataat aatataaatt      780
aaaattttat ttcccaattc aaaaatcata atcaaggagt gaatgctgcc agtagaccaa      840
agtaacaata tttggtgtgt acatcaaatg ataggaaaca acaaaaactc attaatatac      900
ctaaatccat atatatat atatatat atttcaatat ttcacattgt tataattagg      960
tttaatagat accatattag aaatctcagt atggtggttc                            1000
```

<210> SEQ ID NO 32
<211> LENGTH: 178
<212> TYPE: DNA
<213> ORGANISM: Artificial Sequence
<220> FEATURE:
<223> OTHER INFORMATION: Synthetic Vector transcriptional terminator DNA sequence derived from synthetic construct.

<400> SEQUENCE: 32

```
ggaattagaa attttattga tagaagtatt ttacaaatac aaatacatac taagggtttc       60
ttatatgctc aacacatgag cgaaacccta taagaaccct aattccctta tctgggaact      120
actcacacat tattatagag agagatagat ttgtagagag agactggtga tttcagcg         178
```

<210> SEQ ID NO 33
<211> LENGTH: 255
<212> TYPE: DNA
<213> ORGANISM: Artificial Sequence
<220> FEATURE:

<223> OTHER INFORMATION: Synthetic Vector transcriptional terminator DNA
      sequence derived from synthetic construct.

<400> SEQUENCE: 33

```
gatcgttcaa acatttggca ataaagtttc ttaagattga atcctgttgc cggtcttgcg      60
atgattatca tataatttct gttgaattac gttaagcatg taataattaa catgtaatgc     120
atgacgttat ttatgagatg ggtttttatg attagagtcc cgcaattata catttaatac     180
gcgatagaaa acaaaatata gcgcgcaaac taggataaat tatcgcgcgc ggtgtcatct     240
atgttactag atcgg                                                      255
```

<210> SEQ ID NO 34
<211> LENGTH: 931
<212> TYPE: PRT
<213> ORGANISM: Arabidopsis thaliana

<400> SEQUENCE: 34

```
Met Ala Met Arg Leu Leu Lys Thr His Leu Leu Phe Leu His Leu Tyr
1               5                   10                  15

Leu Phe Phe Ser Pro Cys Phe Ala Tyr Thr Asp Met Glu Val Leu Leu
            20                  25                  30

Asn Leu Lys Ser Ser Met Ile Gly Pro Lys Gly His Gly Leu His Asp
        35                  40                  45

Trp Ile His Ser Ser Pro Asp Ala His Cys Ser Phe Ser Gly Val
    50                  55                  60

Ser Cys Asp Asp Asp Ala Arg Val Ile Ser Leu Asn Val Ser Phe Thr
65                  70                  75                  80

Pro Leu Phe Gly Thr Ile Ser Pro Glu Ile Gly Met Leu Thr His Leu
                85                  90                  95

Val Asn Leu Thr Leu Ala Ala Asn Asn Phe Thr Gly Glu Leu Pro Leu
            100                 105                 110

Glu Met Lys Ser Leu Thr Ser Leu Lys Val Leu Asn Ile Ser Asn Asn
        115                 120                 125

Gly Asn Leu Thr Gly Thr Phe Pro Gly Glu Ile Leu Lys Ala Met Val
    130                 135                 140

Asp Leu Glu Val Leu Asp Thr Tyr Asn Asn Asn Phe Asn Gly Lys Leu
145                 150                 155                 160

Pro Pro Glu Met Ser Glu Leu Lys Lys Leu Lys Tyr Ser Phe Gly Gly
                165                 170                 175

Asn Phe Phe Ser Gly Glu Ile Pro Glu Ser Tyr Gly Asp Ile Gln Ser
            180                 185                 190

Leu Glu Tyr Leu Gly Leu Asn Gly Ala Gly Leu Ser Gly Lys Ser Pro
        195                 200                 205

Ala Phe Leu Ser Arg Leu Lys Asn Leu Glu Arg Glu Met Tyr Ile Gly
    210                 215                 220

Tyr Tyr Asn Ser Tyr Thr Gly Gly Val Pro Pro Glu Phe Gly Gly Leu
225                 230                 235                 240

Thr Lys Leu Glu Ile Leu Asp Met Ala Ser Cys Thr Leu Thr Gly Glu
                245                 250                 255

Ile Pro Thr Ser Leu Ser Asn Leu Lys His Leu His Thr Leu Phe Leu
            260                 265                 270

His Ile Asn Asn Leu Thr Gly His Ile Pro Pro Glu Leu Ser Gly Leu
        275                 280                 285

Val Ser Leu Lys Ser Leu Asp Leu Ser Ile Asn Leu Thr Gly Glu Ile
    290                 295                 300
```

```
Pro Gln Ser Phe Ile Asn Leu Gly Asn Ile Thr Leu Ile Asn Leu Phe
305                 310                 315                 320

Arg Asn Asn Leu Tyr Gly Gln Ile Pro Glu Ala Ile Gly Glu Leu Pro
                325                 330                 335

Lys Leu Glu Val Phe Glu Val Trp Glu Asn Asn Phe Thr Leu Gln Leu
            340                 345                 350

Pro Ala Asn Leu Gly Arg Asn Gly Asn Leu Ile Lys Leu Asp Val Ser
                355                 360                 365

Asp Asn His Leu Thr Gly Leu Ile Pro Lys Asp Leu Cys Arg Gly Glu
        370                 375                 380

Lys Leu Glu Met Leu Ile Leu Ser Asn Asn Phe Phe Gly Pro Ile
385                 390                 395                 400

Pro Glu Glu Leu Gly Lys Cys Lys Ser Leu Thr Lys Ile Lys Arg Ile
                405                 410                 415

Val Lys Asn Leu Leu Asn Gly Thr Val Pro Ala Gly Leu Phe Asn Leu
            420                 425                 430

Pro Leu Val Thr Ile Ile Glu Leu Thr Asp Asn Phe Phe Ser Gly Glu
                435                 440                 445

Leu Pro Val Thr Met Ser Gly Asp Val Leu Asp Gln Ile Tyr Leu Ser
        450                 455                 460

Asn Asn Trp Phe Ser Gly Glu Ile Pro Pro Ile Gly Asn Phe Pro
465                 470                 475                 480

Asn Leu Gln Thr Leu Phe Leu Asp Arg Asn Arg Phe Arg Gly Asn Ile
                485                 490                 495

Pro Arg Glu Ile Phe Glu Leu Lys His Leu Ser Arg Ile Asn Thr Ser
            500                 505                 510

Ala Asn Asn Ile Thr Gly Gly Ile Pro Asp Ser Ile Ser Arg Cys Ser
                515                 520                 525

Thr Leu Ile Ser Val Asp Leu Ser Arg Asn Ile Asn Gly Glu Ile Pro
        530                 535                 540

Lys Gly Ile Asn Asn Val Lys Asn Leu Gly Thr Leu Asn Ile Ser Gly
545                 550                 555                 560

Asn Gln Leu Thr Gly Ser Ile Pro Thr Gly Ile Gly Asn Met Thr Ser
                565                 570                 575

Leu Thr Thr Leu Asp Leu Ser Phe Asn Asp Leu Ser Gly Arg Val Pro
            580                 585                 590

Leu Gly Gly Gln Phe Leu Val Phe Asn Glu Thr Ser Phe Ala Gly Asn
                595                 600                 605

Thr Tyr Leu Cys Leu Pro His Arg Val Ser Cys Pro Thr Arg Pro Gly
        610                 615                 620

Gln Thr Ser Asp His Asn His Thr Ala Leu Phe Ser Pro Ser Arg Ile
625                 630                 635                 640

Val Ile Thr Val Ile Ala Ala Ile Thr Gly Leu Ile Leu Ile Ser Val
                645                 650                 655

Ala Ile Arg Gln Met Asn Lys Lys Asn Gln Lys Ser Leu Ala Trp
            660                 665                 670

Lys Leu Thr Ala Phe Gln Lys Leu Asp Phe Lys Ser Glu Asp Val Leu
                675                 680                 685

Glu Cys Leu Lys Glu Glu Asn Ile Ile Gly Lys Gly Ala Gly Ile
        690                 695                 700

Val Tyr Arg Gly Ser Met Pro Asn Asn Val Asp Val Ala Ile Lys Arg
705                 710                 715                 720
```

-continued

Leu Val Gly Arg Gly Thr Gly Arg Ser Asp His Gly Phe Thr Ala Glu
            725                 730                 735

Ile Gln Thr Leu Gly Arg Ile Arg His Arg His Ile Val Arg Leu Leu
            740                 745                 750

Gly Tyr Val Ala Asn Lys Asp Thr Asn Leu Leu Leu Tyr Glu Tyr Met
            755                 760                 765

Pro Asn Gly Ser Leu Gly Glu Leu Leu His Gly Ser Lys Gly Gly His
            770                 775                 780

Leu Gln Trp Glu Thr Arg His Arg Val Ala Val Glu Ala Ala Lys Gly
785                 790                 795                 800

Leu Cys Tyr Leu His His Asp Cys Ser Pro Leu Ile Leu His Arg Asp
            805                 810                 815

Val Lys Ser Asn Asn Ile Leu Leu Asp Ser Phe Glu Ala His Val Ala
            820                 825                 830

Asp Phe Gly Leu Ala Lys Phe Leu Val Asp Gly Ala Ala Ser Glu Cys
            835                 840                 845

Met Ser Ser Ile Ala Gly Ser Tyr Gly Tyr Ile Ala Pro Glu Tyr Ala
            850                 855                 860

Tyr Thr Leu Lys Val Asp Glu Lys Ser Asp Val Tyr Ser Phe Gly Val
865                 870                 875                 880

Val Leu Leu Glu Leu Ile Ala Gly Lys Lys Pro Val Gly Glu Phe Gly
            885                 890                 895

Glu Gly Val Asp Ile Val Arg Trp Val Arg Asn Thr Glu Glu Glu Ile
            900                 905                 910

Thr Gln Pro Ser Asp Ala Ala Ile Val Val Ala Ile Val Asp Pro Arg
            915                 920                 925

Leu Thr Gly
    930

<210> SEQ ID NO 35
<211> LENGTH: 961
<212> TYPE: PRT
<213> ORGANISM: Populus tremula x Populus tremuloides

<400> SEQUENCE: 35

Met Lys Lys Lys Asn Ile Ser Pro Ser Leu Val Leu His Pro Leu Leu
1               5                   10                  15

Leu Leu Leu Leu Pro Phe Phe Ala Phe Asn Ser Leu Ala Leu Lys Phe
            20                  25                  30

Ser Pro Gln Leu Leu Ser Leu Leu Ser Leu Lys Thr Ser Leu Ser Gly
            35                  40                  45

Pro Pro Ser Ala Phe Gln Asp Trp Lys Val Pro Val Asn Gly Gln Asn
    50                  55                  60

Asp Ala Val Trp Cys Ser Trp Ser Gly Val Val Cys Asp Asn Val Thr
65                  70                  75                  80

Ala Gln Val Ile Ser Leu Asp Leu Ser His Arg Asn Leu Ser Gly Arg
            85                  90                  95

Ile Pro Ile Gln Ile Arg Tyr Leu Ser Ser Leu Leu Tyr Leu Asn Leu
            100                 105                 110

Ser Gly Asn Ser Leu Glu Gly Ser Phe Pro Thr Ser Ile Phe Asp Leu
            115                 120                 125

Thr Lys Leu Thr Thr Leu Asp Ile Ser Arg Asn Ser Phe Asp Ser Ser
    130                 135                 140

Phe Pro Pro Gly Ile Ser Lys Leu Lys Phe Leu Lys Val Phe Asn Ala
145                 150                 155                 160

```
Phe Ser Asn Asn Phe Glu Gly Leu Leu Pro Ser Asp Val Ser Arg Leu
                165                 170                 175

Arg Phe Leu Glu Glu Leu Asn Phe Gly Ser Tyr Phe Glu Gly Ile
            180                 185                 190

Pro Ala Ala Tyr Gly Gly Leu Gln Arg Leu Lys Phe Ile His Leu Ala
            195                 200                 205

Gly Asn Val Leu Gly Gly Lys Leu Pro Pro Arg Leu Gly Leu Leu Thr
            210                 215                 220

Glu Leu Gln His Met Glu Ile Gly Tyr Asn His Phe Asn Gly Asn Ile
225                 230                 235                 240

Pro Ser Glu Phe Ala Leu Leu Ser Asn Leu Lys Tyr Phe Asp Val Ser
                245                 250                 255

Asn Cys Ser Leu Ser Gly Ser Leu Pro Gln Glu Leu Gly Asn Leu Ser
                260                 265                 270

Asn Leu Glu Thr Leu Phe Leu Phe Gln Asn Gly Phe Thr Gly Glu Ile
                275                 280                 285

Pro Glu Ser Tyr Ser Asn Leu Lys Ser Leu Lys Leu Leu Asp Phe Ser
                290                 295                 300

Ser Asn Gln Leu Ser Gly Ser Ile Pro Ser Gly Phe Ser Thr Leu Lys
305                 310                 315                 320

Asn Leu Thr Trp Leu Ser Leu Ile Ser Asn Asn Leu Ser Gly Glu Val
                325                 330                 335

Pro Glu Gly Ile Gly Glu Leu Pro Glu Leu Thr Thr Leu Phe Leu Trp
                340                 345                 350

Asn Asn Asn Phe Thr Gly Val Leu Pro His Lys Leu Gly Ser Asn Gly
                355                 360                 365

Lys Leu Glu Thr Met Asp Val Ser Asn Asn Ser Phe Thr Gly Thr Ile
370                 375                 380

Pro Ser Ser Leu Cys His Gly Asn Lys Leu Tyr Lys Leu Ile Leu Phe
385                 390                 395                 400

Ser Asn Met Phe Glu Gly Glu Leu Pro Lys Ser Leu Thr Arg Cys Glu
                405                 410                 415

Ser Leu Trp Arg Phe Arg Ser Gln Asn Asn Arg Leu Asn Gly Thr Ile
                420                 425                 430

Pro Ile Gly Phe Gly Ser Leu Arg Asn Leu Thr Phe Val Asp Leu Ser
                435                 440                 445

Asn Asn Arg Phe Thr Asp Gln Ile Pro Ala Asp Phe Ala Thr Ala Pro
450                 455                 460

Val Leu Gln Tyr Leu Asn Leu Ser Thr Asn Phe His Arg Lys Leu
465                 470                 475                 480

Pro Glu Asn Ile Trp Lys Ala Pro Asn Leu Gln Ile Phe Ser Ala Ser
                485                 490                 495

Phe Ser Asn Leu Ile Gly Glu Ile Pro Asn Tyr Val Gly Cys Lys Ser
                500                 505                 510

Phe Tyr Arg Ile Glu Leu Gln Gly Asn Ser Leu Asn Gly Thr Ile Pro
                515                 520                 525

Trp Asp Ile Gly His Cys Glu Lys Leu Leu Cys Leu Asn Leu Ser Gln
530                 535                 540

Asn His Leu Asn Gly Ile Ile Pro Trp Glu Ile Ser Thr Leu Pro Ser
545                 550                 555                 560

Ile Ala Asp Val Asp Leu Ser His Asn Leu Leu Thr Gly Ile Pro Ser
                565                 570                 575
```

Asp Phe Gly Ser Ser Lys Thr Ile Thr Thr Phe Asn Val Ser Tyr Asn
            580                 585                 590

Gln Leu Ile Gly Pro Ile Pro Ser Gly Ser Phe Ala His Leu Asn Pro
        595                 600                 605

Ser Phe Phe Ser Ser Asn Glu Gly Leu Cys Gly Asp Leu Val Gly Lys
    610                 615                 620

Pro Cys Asn Ser Asp Arg Phe Asn Ala Gly Asn Ala Asp Ile Asp Gly
625                 630                 635                 640

His His Lys Glu Glu Arg Pro Lys Lys Thr Ala Gly Ala Ile Val Trp
            645                 650                 655

Ile Leu Ala Ala Ala Ile Gly Val Gly Phe Phe Val Leu Val Ala Ala
        660                 665                 670

Thr Arg Cys Phe Gln Lys Ser Tyr Gly Asn Arg Val Asp Gly Gly Gly
    675                 680                 685

Arg Asn Gly Gly Asp Ile Gly Pro Trp Lys Leu Thr Ala Phe Gln Arg
    690                 695                 700

Leu Asn Phe Thr Ala Asp Asp Val Val Glu Cys Leu Ser Lys Thr Asp
705                 710                 715                 720

Asn Ile Leu Gly Met Gly Ser Thr Gly Thr Val Tyr Lys Ala Glu Met
            725                 730                 735

Pro Asn Gly Glu Ile Ile Ala Val Lys Lys Leu Trp Gly Lys Asn Lys
        740                 745                 750

Glu Asn Gly Lys Ile Arg Arg Lys Ser Gly Val Leu Ala Glu Val
    755                 760                 765

Asp Val Leu Gly Asn Val Arg His Arg Asn Ile Val Arg Leu Leu Gly
    770                 775                 780

Cys Cys Thr Asn Arg Asp Cys Thr Met Leu Leu Tyr Glu Tyr Met Pro
785                 790                 795                 800

Asn Gly Ser Leu Asp Asp Leu Leu His Gly Gly Asp Lys Thr Met Thr
            805                 810                 815

Ala Ala Ala Glu Trp Thr Ala Leu Tyr Gln Ile Ala Ile Gly Val Ala
        820                 825                 830

Gln Gly Ile Cys Tyr Leu His His Asp Cys Asp Pro Val Ile Val His
    835                 840                 845

Arg Asp Leu Lys Pro Ser Asn Ile Leu Leu Asp Ala Asp Phe Glu Ala
850                 855                 860

Arg Val Ala Asp Phe Gly Val Ala Lys Leu Ile Gln Thr Asp Glu Ser
865                 870                 875                 880

Met Ser Val Val Ala Gly Ser Tyr Gly Tyr Ile Ala Pro Glu Tyr Ala
            885                 890                 895

Tyr Thr Leu Gln Val Asp Lys Lys Ser Asp Ile Tyr Ser Tyr Gly Val
        900                 905                 910

Ile Leu Leu Glu Ile Ile Thr Gly Lys Arg Ser Val Glu Pro Glu Phe
    915                 920                 925

Gly Glu Gly Asn Ser Ile Val Asp Trp Val Arg Ser Lys Leu Lys Thr
    930                 935                 940

Lys Glu Asp Val Glu Glu Val Leu Asp Lys Ser Met Gly Arg Ser Cys
945                 950                 955                 960

Ser

<210> SEQ ID NO 36
<211> LENGTH: 878
<212> TYPE: PRT
<213> ORGANISM: Populus tremula x Populus tremuloides

<400> SEQUENCE: 36

Met Ala Ile Pro Arg Leu Phe Phe Leu Phe Tyr Tyr Ile Gly Phe Ala
1               5                   10                  15

Leu Phe Pro Phe Val Ser Ser Glu Thr Phe Gln Asn Ser Glu Gln Glu
            20                  25                  30

Ile Leu Leu Ala Phe Lys Ser Asp Leu Phe Asp Pro Ser Asn Asn Leu
        35                  40                  45

Gln Asp Trp Lys Arg Pro Glu Asn Ala Thr Thr Phe Ser Glu Leu Val
    50                  55                  60

His Cys His Trp Thr Gly Val His Cys Asp Ala Asn Gly Tyr Val Ala
65                  70                  75                  80

Lys Leu Leu Leu Ser Asn Met Asn Leu Ser Gly Asn Val Ser Asp Gln
                85                  90                  95

Ile Gln Ser Phe Pro Ser Leu Gln Ala Leu Asp Leu Ser Asn Asn Ala
            100                 105                 110

Phe Glu Ser Ser Leu Pro Lys Ser Leu Ser Asn Leu Thr Ser Leu Lys
        115                 120                 125

Val Ile Asp Val Ser Val Asn Ser Phe Phe Gly Thr Phe Pro Tyr Gly
    130                 135                 140

Leu Gly Met Ala Thr Gly Leu Thr His Val Asn Ala Ser Ser Asn Asn
145                 150                 155                 160

Phe Ser Gly Phe Leu Pro Glu Asp Leu Gly Asn Ala Thr Thr Leu Glu
                165                 170                 175

Val Leu Asp Phe Arg Gly Gly Tyr Phe Glu Gly Ser Val Pro Ser Ser
            180                 185                 190

Phe Lys Asn Leu Lys Asn Leu Lys Phe Leu Gly Leu Ser Gly Asn Asn
        195                 200                 205

Phe Gly Gly Lys Val Pro Lys Val Ile Gly Glu Leu Ser Ser Leu Glu
    210                 215                 220

Thr Ile Ile Leu Gly Tyr Asn Gly Phe Met Gly Glu Ile Pro Glu Glu
225                 230                 235                 240

Phe Gly Lys Leu Thr Arg Leu Gln Tyr Leu Asp Leu Ala Val Gly Asn
                245                 250                 255

Leu Thr Gly Gln Ile Pro Ser Ser Leu Gly Gln Leu Lys Gln Leu Thr
            260                 265                 270

Thr Val Tyr Leu Tyr Gln Asn Arg Leu Thr Gly Lys Leu Pro Arg Glu
        275                 280                 285

Leu Gly Gly Met Thr Ser Leu Val Phe Leu Asp Leu Ser Asp Asn Gln
    290                 295                 300

Ile Thr Gly Glu Ile Pro Met Glu Val Gly Glu Leu Lys Asn Leu Gln
305                 310                 315                 320

Leu Leu Asn Leu Met Arg Asn Gln Leu Thr Gly Ile Ile Pro Ser Lys
                325                 330                 335

Ile Ala Glu Leu Pro Asn Leu Glu Val Leu Glu Leu Trp Gln Asn Ser
            340                 345                 350

Leu Met Gly Ser Leu Pro Val His Leu Gly Lys Asn Ser Pro Leu Lys
        355                 360                 365

Trp Leu Asp Val Ser Ser Asn Lys Leu Ser Gly Asp Ile Pro Ser Gly
    370                 375                 380

Leu Cys Tyr Ser Arg Asn Leu Thr Lys Leu Ile Leu Phe Asn Asn Ser
385                 390                 395                 400

Phe Ser Gly Gln Ile Pro Glu Glu Ile Phe Ser Cys Pro Thr Leu Val

```
            405                 410                 415
Arg Val Arg Ile Gln Lys Asn His Ile Ser Gly Ser Ile Pro Ala Gly
            420                 425                 430

Ser Gly Asp Leu Pro Met Leu Gln His Leu Glu Leu Ala Lys Asn Asn
            435                 440                 445

Leu Thr Gly Lys Ile Pro Asp Ile Ala Leu Ser Thr Ser Leu Ser
    450                 455                 460

Phe Ile Asp Ile Ser Phe His Asn Leu Ser Ser Leu Ser Ser Ile
465                 470                 475                 480

Phe Ser Ser Pro Asn Leu Gln Thr Phe Ile Ala Ser His Asn Asn Phe
            485                 490                 495

Ala Gly Lys Ile Pro Asn Gln Ile Gln Asp Arg Pro Ser Leu Ser Val
            500                 505                 510

Leu Asp Leu Ser Phe Asn His Phe Ser Gly Gly Ile Pro Glu Arg Ile
            515                 520                 525

Ala Ser Phe Glu Lys Leu Val Ser Leu Asn Leu Lys Ser Asn Gln Leu
            530                 535                 540

Val Gly Glu Ile Pro Lys Ala Leu Ala Gly Met His Met Leu Ala Val
545                 550                 555                 560

Leu Asp Leu Ser Asn Asn Ser Leu Thr Gly Asn Ile Pro Ala Asp Leu
            565                 570                 575

Gly Ala Ser Pro Thr Leu Glu Met Leu Asn Val Ser Phe Asn Lys Leu
            580                 585                 590

Asp Gly Pro Ile Pro Ser Asn Met Leu Phe Ala Ala Ile Asp Pro Lys
            595                 600                 605

Asp Leu Val Gly Asn Asn Gly Leu Cys Phe Thr Ala Gly Asp Ile Leu
    610                 615                 620

Ser His Ile Lys Glu Ser Asn Ile Ile Gly Met Gly Ala Ile Gly Ile
625                 630                 635                 640

Val Tyr Lys Ala Glu Val Met Arg Arg Leu Leu Thr Val Ala Val
            645                 650                 655

Lys Lys Leu Trp Arg Ser Pro Ser Pro Gln Asn Asp Ile Glu Asp His
            660                 665                 670

His Gln Glu Glu Asp Glu Glu Asp Ile Leu Arg Glu Val Asn Leu
    675                 680                 685

Leu Gly Gly Leu Arg His Arg Asn Ile Val Lys Ile Leu Gly Tyr Val
            690                 695                 700

His Asn Glu Arg Glu Val Met Met Val Tyr Glu Tyr Met Pro Asn Gly
705                 710                 715                 720

Asn Leu Gly Thr Ala Leu His Ser Lys Asp Glu Lys Phe Leu Leu Arg
                725                 730                 735

Asp Trp Leu Ser Arg Tyr Asn Val Ala Val Gly Val Gln Gly Leu
            740                 745                 750

Asn Tyr Leu His Asn Asp Cys Tyr Pro Pro Ile Ile His Arg Asp Ile
            755                 760                 765

Lys Ser Asn Ile Leu Leu Asp Ser Asn Leu Glu Ala Arg Ile Ala Asp
    770                 775                 780

Phe Gly Leu Ala Lys Met Met Leu His Lys Asn Glu Thr Val Ser Met
785                 790                 795                 800

Val Ala Gly Ser Tyr Gly Tyr Ile Ala Pro Glu Tyr Gly Tyr Thr Leu
                805                 810                 815

Lys Ile Asp Glu Lys Ser Asp Ile Tyr Ser Leu Gly Val Val Leu Leu
            820                 825                 830
```

```
Glu Leu Val Thr Gly Lys Met Pro Ile Asp Pro Ser Phe Glu Asp Ser
            835                 840                 845

Ile Asp Val Val Glu Trp Ile Arg Arg Lys Val Lys Lys Asn Glu Ser
850                 855                 860

Leu Glu Glu Val Ile Asp Ala Ser Ile Ala Gly Asp Cys Lys
865                 870                 875

<210> SEQ ID NO 37
<211> LENGTH: 941
<212> TYPE: PRT
<213> ORGANISM: Populus tremula x Populus tremuloides

<400> SEQUENCE: 37

Met Lys Met Lys Ile Ile Val Leu Phe Leu Tyr Tyr Cys Tyr Ile Gly
1               5                   10                  15

Ser Thr Ser Ser Val Leu Ala Ser Ile Asp Asn Val Asn Glu Leu Ser
                20                  25                  30

Val Leu Leu Ser Val Lys Ser Thr Leu Val Asp Pro Leu Asn Phe Leu
            35                  40                  45

Lys Asp Trp Lys Leu Ser Asp Thr Ser Asp His Cys Asn Trp Thr Gly
50                  55                  60

Val Arg Cys Asn Ser Asn Gly Asn Val Glu Lys Leu Asp Leu Ala Gly
65                  70                  75                  80

Met Asn Leu Thr Gly Lys Ile Ser Asp Ser Ile Ser Gln Leu Ser Ser
                85                  90                  95

Leu Val Ser Phe Asn Ile Ser Cys Asn Gly Phe Glu Ser Leu Leu Pro
            100                 105                 110

Lys Ser Ile Pro Leu Pro Lys Ser Ile Asp Ile Ser Gln Asn Ser Phe
        115                 120                 125

Ser Gly Ser Leu Phe Leu Phe Ser Asn Glu Ser Leu Gly Leu Val His
    130                 135                 140

Leu Asn Ala Ser Gly Asn Asn Leu Ser Gly Asn Leu Thr Glu Asp Leu
145                 150                 155                 160

Gly Asn Leu Val Ser Leu Glu Val Leu Asp Leu Arg Gly Asn Phe Phe
                165                 170                 175

Gln Gly Ser Leu Pro Ser Ser Phe Lys Asn Leu Gln Lys Leu Arg Phe
            180                 185                 190

Leu Gly Leu Ser Gly Asn Asn Leu Thr Gly Glu Leu Pro Ser Val Leu
        195                 200                 205

His Gln Leu Pro Ser Leu Glu Thr Ala Ile Leu Gly Tyr Asn Glu Phe
    210                 215                 220

Lys Gly Pro Ile Pro Pro Glu Phe Gly Asn Ile Asn Ser Leu Lys Tyr
225                 230                 235                 240

Leu Asp Leu Ala Ile Gly Lys Leu Ser Gly Glu Ile Pro Ser Glu Leu
                245                 250                 255

Gly Lys Leu Lys Ser Leu Glu Thr Leu Leu Tyr Glu Asn Asn Phe
            260                 265                 270

Thr Gly Thr Ile Pro Arg Glu Ile Gly Ser Ile Thr Thr Leu Lys Val
        275                 280                 285

Leu Asp Phe Ser Asp Asn Ala Leu Thr Gly Glu Ile Pro Met Glu Ile
    290                 295                 300

Thr Lys Leu Lys Asn Leu Gln Leu Leu Asn Leu Met Glu Asn Lys Leu
305                 310                 315                 320

Ser Gly Ser Ile Pro Pro Ala Ile Ser Ser Leu Ala Gln Leu Val Leu
```

```
              325                 330                 335
Glu Leu Trp Asn Asn Thr Leu Ser Gly Glu Leu Pro Ser Asp Leu Gly
            340                 345                 350
Lys Asn Ser Pro Leu Gln Trp Leu Asp Val Ser Ser Asn Ser Phe Ser
            355                 360                 365
Gly Glu Ile Pro Ser Thr Leu Cys Asn Lys Gly Asn Leu Thr Lys Leu
            370                 375                 380
Ile Leu Phe Asn Asn Thr Phe Thr Gly Gln Ile Pro Ala Thr Leu Ser
385                 390                 395                 400
Thr Cys Gln Ser Leu Val Arg Val Arg Met Gln Asn Asn Leu Leu Asn
                405                 410                 415
Gly Ser Ile Pro Ile Gly Phe Gly Lys Leu Glu Lys Leu Gln Arg Leu
                420                 425                 430
Glu Leu Ala Gly Asn Arg Leu Ser Gly Gly Ile Pro Gly Asp Ile Ser
                435                 440                 445
Asp Ser Val Ser Leu Ser Phe Ile Asp Phe Ser Arg Asn Gln Ile Arg
            450                 455                 460
Ser Ser Leu Pro Ser Thr Ile Leu Ser Ile His Asn Leu Gln Ala Phe
465                 470                 475                 480
Leu Val Ala Asp Asn Phe Ile Ser Gly Glu Val Pro Asp Gln Phe Gln
                485                 490                 495
Asp Cys Pro Ser Leu Ser Asn Leu Asp Leu Ser Ser Asn Thr Leu Thr
            500                 505                 510
Gly Thr Ile Pro Ser Ser Ile Ala Ser Cys Glu Lys Leu Val Ser Leu
            515                 520                 525
Asn Leu Arg Asn Asn Asn Leu Thr Gly Glu Ile Pro Arg Gln Ile Thr
            530                 535                 540
Thr Met Ser Ala Leu Ala Val Leu Asp Leu Ser Asn Asn Ser Leu Thr
545                 550                 555                 560
Gly Val Leu Pro Glu Ser Ile Gly Thr Ser Pro Ala Leu Glu Leu Leu
                565                 570                 575
Asn Val Ser Tyr Asn Lys Leu Thr Gly Pro Val Pro Ile Asn Gly Phe
            580                 585                 590
Leu Lys Thr Ile Asn Pro Asp Asp Leu Arg Gly Asn Ser Gly Leu Cys
            595                 600                 605
Gly Gly Val Leu Pro Pro Cys Ser Lys Phe Gln Arg Ala Thr Ser Ser
            610                 615                 620
His Ser Ser Leu His Gly Lys Arg Ile Val Ala Gly Trp Leu Ile Gly
625                 630                 635                 640
Ile Ala Ser Val Leu Ala Leu Gly Ile Leu Thr Ile Val Thr Arg Thr
                645                 650                 655
Leu Tyr Lys Lys Trp Tyr Ser Asn Gly Phe Cys Gly Asp Glu Thr Ala
            660                 665                 670
Ser Lys Gly Glu Trp Pro Trp Arg Leu Met Ala Phe His Arg Leu Gly
            675                 680                 685
Phe Thr Ala Ser Asp Ile Leu Ala Cys Ile Lys Glu Ser Asn Met Ile
            690                 695                 700
Gly Met Gly Ala Thr Gly Ile Val Tyr Lys Ala Glu Met Ser Arg Ser
705                 710                 715                 720
Ser Thr Val Leu Ala Val Lys Lys Leu Trp Arg Ser Ala Ala Asp Ile
                725                 730                 735
Glu Asp Gly Thr Thr Gly Asp Phe Val Gly Glu Val Asn Leu Leu Gly
            740                 745                 750
```

```
Lys Leu Arg His Arg Asn Ile Val Arg Leu Leu Gly Phe Leu Tyr Asn
            755                 760                 765

Asp Lys Asn Met Met Ile Val Tyr Glu Phe Met Leu Asn Gly Asn Leu
        770                 775                 780

Gly Asp Ala Ile His Gly Lys Asn Ala Ala Gly Arg Leu Leu Val Asp
785                 790                 795                 800

Trp Val Ser Arg Tyr Asn Ile Ala Leu Gly Val Ala His Gly Leu Ala
                805                 810                 815

Tyr Leu His His Asp Cys His Pro Pro Val Ile His Arg Asp Ile Lys
                820                 825                 830

Ser Asn Asn Ile Leu Leu Asp Ala Asn Leu Asp Ala Arg Ile Ala Asp
                835                 840                 845

Phe Gly Leu Ala Arg Met Met Ala Arg Lys Lys Glu Thr Val Ser Met
        850                 855                 860

Val Ala Gly Ser Tyr Gly Tyr Ile Ala Pro Glu Tyr Gly Tyr Thr Leu
865                 870                 875                 880

Lys Val Asp Glu Lys Ile Asp Ile Tyr Ser Tyr Gly Val Val Leu Leu
                885                 890                 895

Glu Leu Leu Thr Gly Arg Arg Pro Leu Glu Pro Glu Phe Gly Glu Ser
            900                 905                 910

Val Asp Ile Val Glu Trp Val Arg Ile Lys Ile Arg Asp Asn Ile Ser
            915                 920                 925

Leu Glu Glu Ala Leu Asp Pro Asn Val Gly Asn Cys Arg
            930                 935                 940

<210> SEQ ID NO 38
<211> LENGTH: 958
<212> TYPE: PRT
<213> ORGANISM: Oryza sativa

<400> SEQUENCE: 38

Met Glu Ala Thr Val Pro Val Leu Leu Leu Val Thr Val Leu Ser Leu
1               5                   10                  15

Ile Leu Pro Ser Gly Ile Gly Ala Ala Ala Gly Asp Glu Arg Ser
            20                  25                  30

Ala Leu Leu Ala Lys Ala Gly Phe Val Asp Thr Val Ser Ala Leu Ala
        35                  40                  45

Asp Trp Thr Asp Gly Gly Lys Ala Ser Pro His Cys Lys Trp Thr Gly
    50                  55                  60

Val Gly Cys Asn Ala Ala Gly Leu Val Asp Arg Leu Arg Leu Ser Gly
65              70                  75                  80

Lys Asn Leu Ser Gly Lys Val Ala Asp Val Phe Arg Leu Pro Ala
                85                  90                  95

Leu Ala Val Leu Asn Ile Ser Asn Asn Ala Phe Ala Thr Thr Leu Pro
            100                 105                 110

Lys Ser Leu Pro Ser Leu Pro Ser Leu Lys Val Phe Asp Val Ser Gln
        115                 120                 125

Asn Ser Phe Glu Gly Gly Phe Pro Ala Gly Leu Gly Gly Cys Ala Asp
    130                 135                 140

Leu Val Ala Val Asn Ala Ser Gly Asn Asn Phe Ala Gly Pro Leu Pro
145                 150                 155                 160

Glu Asp Leu Ala Asn Ala Thr Ser Leu Glu Thr Ile Asp Met Arg Gly
                165                 170                 175

Ser Phe Phe Gly Gly Ala Ile Pro Ala Ala Tyr Arg Arg Leu Tyr Lys
```

```
                180             185             190
Leu Lys Phe Leu Gly Leu Ser Gly Asn Asn Ile Thr Gly Lys Ile Pro
            195             200             205
Pro Glu Ile Gly Glu Met Glu Ser Leu Glu Ser Leu Ile Gly Tyr
    210             215             220
Asn Glu Leu Glu Gly Gly Ile Pro Pro Glu Leu Gly Asn Leu Ala Asn
225             230             235             240
Leu Gln Tyr Leu Asp Leu Ala Val Gly Asn Leu Asp Gly Pro Ile Pro
            245             250             255
Pro Glu Leu Gly Lys Leu Pro Ala Leu Thr Ser Leu Tyr Leu Tyr Lys
        260             265             270
Asn Asn Leu Glu Gly Lys Ile Pro Pro Glu Leu Gly Asn Ile Ser Thr
        275             280             285
Leu Val Phe Leu Asp Leu Ser Asp Asn Ala Phe Thr Gly Ala Ile Pro
        290             295             300
Asp Glu Val Ala Gln Leu Ser His Leu Arg Leu Leu Asn Leu Met Cys
305             310             315             320
Asn His Leu Asp Gly Val Val Pro Ala Ala Ile Gly Asp Met Pro Lys
            325             330             335
Leu Glu Val Leu Glu Leu Trp Asn Asn Ser Leu Thr Gly Ser Leu Pro
        340             345             350
Ala Ser Leu Gly Arg Ser Ser Pro Leu Gln Trp Val Asp Val Ser Ser
        355             360             365
Asn Gly Phe Thr Gly Gly Ile Pro Ala Gly Ile Cys Asp Gly Lys Ala
        370             375             380
Leu Ile Lys Leu Ile Met Phe Asn Asn Gly Phe Thr Gly Gly Ile Pro
385             390             395             400
Ala Gly Leu Ala Ser Cys Ala Ser Leu Val Arg Met Arg Val His Gly
            405             410             415
Asn Arg Leu Asn Gly Thr Ile Pro Val Gly Phe Gly Lys Leu Pro Leu
            420             425             430
Leu Gln Arg Leu Glu Leu Ala Gly Asn Asp Leu Ser Gly Glu Ile Pro
        435             440             445
Gly Asp Leu Ala Ser Ser Ala Ser Leu Ser Phe Ile Asp Val Ser Arg
    450             455             460
Asn His Leu Gln Tyr Ser Ile Pro Ser Ser Leu Phe Thr Ile Pro Thr
465             470             475             480
Leu Gln Ser Phe Leu Ala Ser Asp Asn Met Ile Ser Gly Glu Leu Pro
            485             490             495
Asp Gln Phe Gln Asp Cys Pro Ala Leu Ala Ala Leu Asp Leu Ser Asn
        500             505             510
Asn Arg Leu Ala Gly Ala Ile Pro Ser Ser Leu Ala Ser Cys Gln Arg
        515             520             525
Leu Val Lys Leu Asn Leu Arg Arg Asn Lys Leu Ala Gly Glu Ile Pro
        530             535             540
Arg Ser Leu Ala Asn Met Pro Ala Leu Ala Ile Leu Asp Leu Ser Ser
545             550             555             560
Asn Val Leu Thr Gly Gly Ile Pro Glu Asn Phe Gly Ser Ser Pro Ala
            565             570             575
Leu Glu Thr Leu Asn Leu Ala Tyr Asn Asn Leu Thr Gly Pro Val Pro
        580             585             590
Gly Asn Gly Val Leu Arg Ser Ile Asn Pro Asp Glu Leu Ala Gly Asn
        595             600             605
```

```
Ala Gly Leu Cys Gly Gly Val Leu Pro Pro Cys Ser Gly Ser Arg Ser
            610                 615                 620

Thr Ala Ala Gly Pro Arg Ser Arg Gly Ser Ala Arg Leu Arg His Ile
625                 630                 635                 640

Ala Val Gly Trp Leu Val Gly Met Val Ala Val Ala Ala Phe Ala
            645                 650                 655

Ala Leu Phe Gly Gly His Tyr Ala Tyr Arg Arg Trp Tyr Val Asp Gly
            660                 665                 670

Ala Gly Cys Cys Asp Asp Glu Asn Leu Gly Gly Ser Gly Ala Trp
            675                 680                 685

Pro Trp Arg Leu Thr Ala Phe Gln Arg Leu Gly Phe Thr Cys Ala Glu
            690                 695                 700

Val Leu Ala Cys Val Lys Glu Ala Asn Val Val Gly Met Gly Ala Thr
705                 710                 715                 720

Gly Val Val Tyr Lys Ala Glu Leu Pro Arg Ala Arg Ala Val Ile Ala
            725                 730                 735

Val Lys Lys Leu Trp Arg Pro Ala Ala Ala Glu Ala Ala Ala Ala
            740                 745                 750

Ala Pro Glu Leu Thr Ala Glu Val Leu Lys Glu Val Gly Leu Leu Gly
            755                 760                 765

Arg Leu Arg His Arg Asn Ile Val Arg Leu Leu Gly Tyr Met His Asn
770                 775                 780

Glu Ala Asp Ala Met Met Leu Tyr Glu Phe Met Pro Asn Gly Ser Leu
785                 790                 795                 800

Trp Glu Ala Leu His Gly Pro Pro Glu Arg Arg Thr Tyr Leu Val Asp
            805                 810                 815

Trp Val Ser Arg Tyr Asp Val Ala Ala Gly Val Ala Gln Gly Leu Ala
            820                 825                 830

Tyr Leu His His Asp Cys His Pro Pro Val Ile His Arg Asp Ile Lys
            835                 840                 845

Ser Asn Asn Ile Leu Leu Asp Ala Asn Met Glu Ala Arg Ile Ala Asp
850                 855                 860

Phe Gly Leu Ala Arg Ala Leu Gly Arg Ala Gly Glu Ser Val Ser Val
865                 870                 875                 880

Val Ala Gly Ser Tyr Gly Tyr Ile Ala Pro Glu Tyr Gly Tyr Thr Met
            885                 890                 895

Lys Val Asp Gln Lys Ser Asp Thr Tyr Ser Tyr Gly Val Val Leu Met
            900                 905                 910

Glu Leu Ile Thr Gly Arg Arg Ala Val Glu Ala Ala Phe Gly Glu Gly
            915                 920                 925

Gln Asp Ile Val Gly Trp Val Arg Asn Lys Ile Arg Ser Asn Thr Val
            930                 935                 940

Glu Asp His Leu Asp Gly Gln Leu Val Gly Ala Gly Cys Pro
945                 950                 955
```

<210> SEQ ID NO 39
<211> LENGTH: 794
<212> TYPE: PRT
<213> ORGANISM: Populus tremula x Populus tremuloides

<400> SEQUENCE: 39

```
Met Met Ser Ser Leu Gln Lys Pro Phe Ser Met Phe Leu Arg Val Leu
1               5                   10                  15

Phe Phe Leu Leu Leu Met Cys Ile Ile Pro Ser Phe Phe Ala Phe Pro
```

```
              20                  25                  30
Ser Asn Ser Ser Ala Thr Ser Phe Gly Ala Ala Lys Tyr Glu Ala Ala
              35                  40                  45
Glu Gly Asn Glu Glu Ala Glu Ala Leu Leu Lys Trp Arg Ala Ser Leu
              50                  55                  60
Asp Asp Ser His Ser Gln Ser Val Leu Ser Trp Val Gly Ser Ser
 65                  70                  75                  80
Pro Cys Lys Trp Leu Gly Ile Thr Cys Asp Asn Ser Gly Ser Val Ala
                  85                  90                  95
Asn Phe Ser Leu Pro His Phe Gly Leu Arg Gly Thr Leu His Ser Phe
                 100                 105                 110
Asn Phe Ser Ser Phe Pro Asn Leu Leu Thr Pro Asn Leu Arg Asn Asn
             115                 120                 125
Ser Leu Tyr Gly Thr Ile Pro Ser His Ile Ser Asn Leu Thr Lys Ile
             130                 135                 140
Thr Asn Leu Asn Leu Cys His Asn His Phe Asn Gly Ser Leu Pro Pro
145                 150                 155                 160
Glu Met Asn Asn Leu Thr His Leu Met Val Leu His Leu Phe Ser Asn
                 165                 170                 175
Asn Phe Thr Gly His Leu Pro Arg Asp Leu Cys Leu Gly Gly Leu Leu
             180                 185                 190
Val Asn Phe Thr Ala Ser Tyr Asn His Phe Ser Gly Pro Ile Pro Lys
             195                 200                 205
Ser Leu Arg Asn Cys Thr Ser Leu Phe Arg Val Arg Leu Asp Trp Asn
             210                 215                 220
Gln Leu Thr Gly Asn Ile Ser Glu Asp Phe Gly Leu Tyr Pro Asn Leu
225                 230                 235                 240
Asn Tyr Val Asp Leu Ser His Asn Asn Leu Tyr Gly Glu Leu Thr Trp
                 245                 250                 255
Lys Trp Gly Gly Phe Asn Asn Leu Thr Ser Leu Lys Leu Ser Asn Asn
             260                 265                 270
Asn Ile Thr Gly Glu Ile Pro Ser Glu Ile Ala Lys Ala Thr Gly Leu
275                 280                 285
Gln Met Ile Asp Leu Ser Ser Asn Leu Leu Lys Gly Thr Ile Pro Lys
             290                 295                 300
Glu Leu Gly Lys Leu Lys Ala Leu Tyr Asn Leu Thr Leu His Asn Asn
305                 310                 315                 320
His Leu Phe Gly Val Val Pro Phe Glu Ile Gln Met Leu Ser Gln Leu
                 325                 330                 335
Arg Ala Leu Asn Leu Ala Ser Asn Asn Leu Gly Gly Ser Ile Pro Lys
             340                 345                 350
Gln Leu Gly Glu Cys Ser Asn Leu Gln Leu Asn Leu Ser His Asn
             355                 360                 365
Lys Phe Ile Gly Ser Ile Pro Ser Glu Ile Gly Phe Leu His Phe Leu
             370                 375                 380
Gly Asp Leu Asp Leu Ser Gly Asn Leu Leu Ala Gly Ile Glu Pro Ser
385                 390                 395                 400
Glu Ile Gly Gln Leu Lys Gln Leu Glu Thr Met Asn Leu Ser His Asn
                 405                 410                 415
Lys Leu Ser Gly Leu Ile Pro Thr Ala Phe Val Asp Leu Val Ser Leu
             420                 425                 430
Thr Thr Val Asp Ile Ser Tyr Asn Glu Leu Glu Gly Pro Ile Pro Lys
             435                 440                 445
```

Ile Lys Gly Phe Ile Glu Ala Pro Leu Glu Ala Phe Met Asn Asn Ser
450                 455                 460

Gly Leu Cys Gly Asn Ala Asn Gly Leu Lys Pro Cys Thr Leu Leu Thr
465                 470                 475                 480

Ser Arg Lys Lys Ser Asn Lys Ile Val Ile Leu Ile Leu Phe Pro Leu
                485                 490                 495

Leu Gly Ser Leu Leu Leu Leu Ile Met Val Gly Cys Leu Tyr Phe
            500                 505                 510

His His Gln Thr Ser Arg Glu Arg Ile Ser Cys Leu Gly Glu Arg Gln
                515                 520                 525

Ser Pro Leu Ser Phe Val Val Trp Gly His Glu Glu Ile His Glu
530                 535                 540

Thr Ile Ile Gln Ala Ala Asn Asn Phe Asn Phe Asn Asn Cys Ile Gly
545                 550                 555                 560

Lys Gly Gly Tyr Gly Ile Val Tyr Arg Ala Met Leu Pro Thr Gly Gln
                565                 570                 575

Val Val Ala Val Lys Lys Phe His Pro Ser Arg Asp Gly Glu Leu Met
                580                 585                 590

Asn Leu Arg Thr Phe Arg Asn Glu Ile Arg Met Leu Ile Asp Ile Arg
            595                 600                 605

His Arg Asn Ile Val Lys Leu His Gly Phe Cys Ser Leu Ile Glu His
610                 615                 620

Ser Phe Leu Val Tyr Glu Phe Ile Glu Arg Gly Ser Leu Lys Met Asn
625                 630                 635                 640

Leu Ser Ser Glu Glu Gln Val Met Asp Leu Asp Trp Asn Arg Arg Leu
                645                 650                 655

Asn Val Val Lys Gly Val Ala Ser Ala Leu Ser Tyr Leu His His Asp
                660                 665                 670

Cys Ser Pro Pro Ile Ile His Arg Asp Ile Ser Ser Asn Val Leu
            675                 680                 685

Leu Asp Ser Glu Tyr Glu Ala His Val Ser Asp Phe Gly Thr Ala Glu
690                 695                 700

Leu Leu Met Pro Asp Ser Thr Asn Trp Thr Ser Phe Ala Gly Thr Leu
705                 710                 715                 720

Gly Tyr Thr Ala Pro Glu Leu Ala Tyr Thr Met Arg Val Asn Glu Lys
                725                 730                 735

Cys Asp Val Tyr Ser Phe Gly Val Val Thr Met Glu Val Ile Met Gly
                740                 745                 750

Met His Pro Gly Asp Leu Ile Ser Phe Leu Tyr Ala Ser Ala Phe Ser
            755                 760                 765

Ser Ser Ser Cys Ser Gln Ile Asn Gln His Ala Leu Leu Lys Asp Val
770                 775                 780

Ile Asp Gln Arg Ile Pro Leu Pro Glu Asn
785                 790

<210> SEQ ID NO 40
<211> LENGTH: 992
<212> TYPE: PRT
<213> ORGANISM: Artificial Sequence
<220> FEATURE:
<223> OTHER INFORMATION: Synthetic consensus protein sequence for PXY
      derived from Arabidopsis thaliana.
<220> FEATURE:
<221> NAME/KEY: MISC_FEATURE
<222> LOCATION: (1)..(5)
<223> OTHER INFORMATION: Xaa can be any naturally occurring amino acid.

```
<220> FEATURE:
<221> NAME/KEY: MISC_FEATURE
<222> LOCATION: (7)..(38)
<223> OTHER INFORMATION: Xaa can be any naturally occurring amino acid.
<220> FEATURE:
<221> NAME/KEY: MISC_FEATURE
<222> LOCATION: (41)..(116)
<223> OTHER INFORMATION: Xaa can be any naturally occurring amino acid.
<220> FEATURE:
<221> NAME/KEY: MISC_FEATURE
<222> LOCATION: (118)..(138)
<223> OTHER INFORMATION: Xaa can be any naturally occurring amino acid.
<220> FEATURE:
<221> NAME/KEY: MISC_FEATURE
<222> LOCATION: (140)..(171)
<223> OTHER INFORMATION: Xaa can be any naturally occurring amino acid.
<220> FEATURE:
<221> NAME/KEY: MISC_FEATURE
<222> LOCATION: (173)..(197)
<223> OTHER INFORMATION: Xaa can be any naturally occurring amino acid.
<220> FEATURE:
<221> NAME/KEY: MISC_FEATURE
<222> LOCATION: (199)..(209)
<223> OTHER INFORMATION: Xaa can be any naturally occurring amino acid.
<220> FEATURE:
<221> NAME/KEY: MISC_FEATURE
<222> LOCATION: (211)..(212)
<223> OTHER INFORMATION: Xaa can be any naturally occurring amino acid.
<220> FEATURE:
<221> NAME/KEY: MISC_FEATURE
<222> LOCATION: (214)..(240)
<223> OTHER INFORMATION: Xaa can be any naturally occurring amino acid.
<220> FEATURE:
<221> NAME/KEY: MISC_FEATURE
<222> LOCATION: (242)..(244)
<223> OTHER INFORMATION: Xaa can be any naturally occurring amino acid.
<220> FEATURE:
<221> NAME/KEY: MISC_FEATURE
<222> LOCATION: (246)..(246)
<223> OTHER INFORMATION: Xaa can be any naturally occurring amino acid.
<220> FEATURE:
<221> NAME/KEY: MISC_FEATURE
<222> LOCATION: (249)..(253)
<223> OTHER INFORMATION: Xaa can be any naturally occurring amino acid.
<220> FEATURE:
<221> NAME/KEY: MISC_FEATURE
<222> LOCATION: (255)..(256)
<223> OTHER INFORMATION: Xaa can be any naturally occurring amino acid.
<220> FEATURE:
<221> NAME/KEY: MISC_FEATURE
<222> LOCATION: (258)..(261)
<223> OTHER INFORMATION: Xaa can be any naturally occurring amino acid.
<220> FEATURE:
<221> NAME/KEY: MISC_FEATURE
<222> LOCATION: (263)..(268)
<223> OTHER INFORMATION: Xaa can be any naturally occurring amino acid.
<220> FEATURE:
<221> NAME/KEY: MISC_FEATURE
<222> LOCATION: (270)..(270)
<223> OTHER INFORMATION: Xaa can be any naturally occurring amino acid.
<220> FEATURE:
<221> NAME/KEY: MISC_FEATURE
<222> LOCATION: (273)..(274)
<223> OTHER INFORMATION: Xaa can be any naturally occurring amino acid.
<220> FEATURE:
<221> NAME/KEY: MISC_FEATURE
<222> LOCATION: (276)..(277)
<223> OTHER INFORMATION: Xaa can be any naturally occurring amino acid.
<220> FEATURE:
<221> NAME/KEY: MISC_FEATURE
<222> LOCATION: (279)..(280)
<223> OTHER INFORMATION: Xaa can be any naturally occurring amino acid.
<220> FEATURE:
<221> NAME/KEY: MISC_FEATURE
<222> LOCATION: (282)..(283)
<223> OTHER INFORMATION: Xaa can be any naturally occurring amino acid.
<220> FEATURE:
<221> NAME/KEY: MISC_FEATURE
<222> LOCATION: (285)..(285)
```

```
<223> OTHER INFORMATION: Xaa can be any naturally occurring amino acid.
<220> FEATURE:
<221> NAME/KEY: MISC_FEATURE
<222> LOCATION: (287)..(288)
<223> OTHER INFORMATION: Xaa can be any naturally occurring amino acid.
<220> FEATURE:
<221> NAME/KEY: MISC_FEATURE
<222> LOCATION: (290)..(292)
<223> OTHER INFORMATION: Xaa can be any naturally occurring amino acid.
<220> FEATURE:
<221> NAME/KEY: MISC_FEATURE
<222> LOCATION: (294)..(294)
<223> OTHER INFORMATION: Xaa can be any naturally occurring amino acid.
<220> FEATURE:
<221> NAME/KEY: MISC_FEATURE
<222> LOCATION: (297)..(304)
<223> OTHER INFORMATION: Xaa can be any naturally occurring amino acid.
<220> FEATURE:
<221> NAME/KEY: MISC_FEATURE
<222> LOCATION: (306)..(310)
<223> OTHER INFORMATION: Xaa can be any naturally occurring amino acid.
<220> FEATURE:
<221> NAME/KEY: MISC_FEATURE
<222> LOCATION: (312)..(312)
<223> OTHER INFORMATION: Xaa can be any naturally occurring amino acid.
<220> FEATURE:
<221> NAME/KEY: MISC_FEATURE
<222> LOCATION: (314)..(315)
<223> OTHER INFORMATION: Xaa can be any naturally occurring amino acid.
<220> FEATURE:
<221> NAME/KEY: MISC_FEATURE
<222> LOCATION: (318)..(318)
<223> OTHER INFORMATION: Xaa can be any naturally occurring amino acid.
<220> FEATURE:
<221> NAME/KEY: MISC_FEATURE
<222> LOCATION: (321)..(328)
<223> OTHER INFORMATION: Xaa can be any naturally occurring amino acid.
<220> FEATURE:
<221> NAME/KEY: MISC_FEATURE
<222> LOCATION: (330)..(331)
<223> OTHER INFORMATION: Xaa can be any naturally occurring amino acid.
<220> FEATURE:
<221> NAME/KEY: MISC_FEATURE
<222> LOCATION: (333)..(333)
<223> OTHER INFORMATION: Xaa can be any naturally occurring amino acid.
<220> FEATURE:
<221> NAME/KEY: MISC_FEATURE
<222> LOCATION: (335)..(336)
<223> OTHER INFORMATION: Xaa can be any naturally occurring amino acid.
<220> FEATURE:
<221> NAME/KEY: MISC_FEATURE
<222> LOCATION: (338)..(338)
<223> OTHER INFORMATION: Xaa can be any naturally occurring amino acid.
<220> FEATURE:
<221> NAME/KEY: MISC_FEATURE
<222> LOCATION: (340)..(340)
<223> OTHER INFORMATION: Xaa can be any naturally occurring amino acid.
<220> FEATURE:
<221> NAME/KEY: MISC_FEATURE
<222> LOCATION: (342)..(342)
<223> OTHER INFORMATION: Xaa can be any naturally occurring amino acid.
<220> FEATURE:
<221> NAME/KEY: MISC_FEATURE
<222> LOCATION: (344)..(352)
<223> OTHER INFORMATION: Xaa can be any naturally occurring amino acid.
<220> FEATURE:
<221> NAME/KEY: MISC_FEATURE
<222> LOCATION: (354)..(356)
<223> OTHER INFORMATION: Xaa can be any naturally occurring amino acid.
<220> FEATURE:
<221> NAME/KEY: misc_feature
<222> LOCATION: (357)..(357)
<223> OTHER INFORMATION: Xaa can be any naturally occurring amino acid
<220> FEATURE:
<221> NAME/KEY: misc_feature
<222> LOCATION: (359)..(360)
<223> OTHER INFORMATION: Xaa can be any naturally occurring amino acid
<220> FEATURE:
<221> NAME/KEY: MISC_FEATURE
```

```
<222> LOCATION: (362)..(366)
<223> OTHER INFORMATION: Xaa can be any naturally occurring amino acid.
<220> FEATURE:
<221> NAME/KEY: MISC_FEATURE
<222> LOCATION: (368)..(371)
<223> OTHER INFORMATION: Xaa can be any naturally occurring amino acid.
<220> FEATURE:
<221> NAME/KEY: MISC_FEATURE
<222> LOCATION: (373)..(376)
<223> OTHER INFORMATION: Xaa can be any naturally occurring amino acid.
<220> FEATURE:
<221> NAME/KEY: MISC_FEATURE
<222> LOCATION: (378)..(379)
<223> OTHER INFORMATION: Xaa can be any naturally occurring amino acid.
<220> FEATURE:
<221> NAME/KEY: MISC_FEATURE
<222> LOCATION: (381)..(381)
<223> OTHER INFORMATION: Xaa can be any naturally occurring amino acid.
<220> FEATURE:
<221> NAME/KEY: MISC_FEATURE
<222> LOCATION: (384)..(384)
<223> OTHER INFORMATION: Xaa can be any naturally occurring amino acid.
<220> FEATURE:
<221> NAME/KEY: MISC_FEATURE
<222> LOCATION: (386)..(387)
<223> OTHER INFORMATION: Xaa can be any naturally occurring amino acid.
<220> FEATURE:
<221> NAME/KEY: MISC_FEATURE
<222> LOCATION: (390)..(390)
<223> OTHER INFORMATION: Xaa can be any naturally occurring amino acid.
<220> FEATURE:
<221> NAME/KEY: MISC_FEATURE
<222> LOCATION: (393)..(394)
<223> OTHER INFORMATION: Xaa can be any naturally occurring amino acid.
<220> FEATURE:
<221> NAME/KEY: MISC_FEATURE
<222> LOCATION: (396)..(400)
<223> OTHER INFORMATION: Xaa can be any naturally occurring amino acid.
<220> FEATURE:
<221> NAME/KEY: MISC_FEATURE
<222> LOCATION: (402)..(403)
<223> OTHER INFORMATION: Xaa can be any naturally occurring amino acid.
<220> FEATURE:
<221> NAME/KEY: MISC_FEATURE
<222> LOCATION: (405)..(405)
<223> OTHER INFORMATION: Xaa can be any naturally occurring amino acid.
<220> FEATURE:
<221> NAME/KEY: MISC_FEATURE
<222> LOCATION: (407)..(408)
<223> OTHER INFORMATION: Xaa can be any naturally occurring amino acid.
<220> FEATURE:
<221> NAME/KEY: MISC_FEATURE
<222> LOCATION: (410)..(412)
<223> OTHER INFORMATION: Xaa can be any naturally occurring amino acid.
<220> FEATURE:
<221> NAME/KEY: MISC_FEATURE
<222> LOCATION: (414)..(414)
<223> OTHER INFORMATION: Xaa can be any naturally occurring amino acid.
<220> FEATURE:
<221> NAME/KEY: MISC_FEATURE
<222> LOCATION: (417)..(418)
<223> OTHER INFORMATION: Xaa can be any naturally occurring amino acid.
<220> FEATURE:
<221> NAME/KEY: MISC_FEATURE
<222> LOCATION: (420)..(424)
<223> OTHER INFORMATION: Xaa can be any naturally occurring amino acid.
<220> FEATURE:
<221> NAME/KEY: MISC_FEATURE
<222> LOCATION: (426)..(432)
<223> OTHER INFORMATION: Xaa can be any naturally occurring amino acid.
<220> FEATURE:
<221> NAME/KEY: MISC_FEATURE
<222> LOCATION: (434)..(434)
<223> OTHER INFORMATION: Xaa can be any naturally occurring amino acid.
<220> FEATURE:
<221> NAME/KEY: MISC_FEATURE
<222> LOCATION: (436)..(436)
<223> OTHER INFORMATION: Xaa can be any naturally occurring amino acid.
<220> FEATURE:
```

```
<221> NAME/KEY: MISC_FEATURE
<222> LOCATION: (438)..(438)
<223> OTHER INFORMATION: Xaa can be any naturally occurring amino acid.
<220> FEATURE:
<221> NAME/KEY: MISC_FEATURE
<222> LOCATION: (441)..(445)
<223> OTHER INFORMATION: Xaa can be any naturally occurring amino acid.
<220> FEATURE:
<221> NAME/KEY: MISC_FEATURE
<222> LOCATION: (447)..(448)
<223> OTHER INFORMATION: Xaa can be any naturally occurring amino acid.
<220> FEATURE:
<221> NAME/KEY: misc_feature
<222> LOCATION: (450)..(450)
<223> OTHER INFORMATION: Xaa can be any naturally occurring amino acid
<220> FEATURE:
<221> NAME/KEY: MISC_FEATURE
<222> LOCATION: (451)..(451)
<223> OTHER INFORMATION: Xaa can be any naturally occurring amino acid.
<220> FEATURE:
<221> NAME/KEY: MISC_FEATURE
<222> LOCATION: (453)..(453)
<223> OTHER INFORMATION: Xaa can be any naturally occurring amino acid.
<220> FEATURE:
<221> NAME/KEY: MISC_FEATURE
<222> LOCATION: (455)..(456)
<223> OTHER INFORMATION: Xaa can be any naturally occurring amino acid.
<220> FEATURE:
<221> NAME/KEY: MISC_FEATURE
<222> LOCATION: (458)..(508)
<223> OTHER INFORMATION: Xaa can be any naturally occurring amino acid.
<220> FEATURE:
<221> NAME/KEY: MISC_FEATURE
<222> LOCATION: (510)..(510)
<223> OTHER INFORMATION: Xaa can be any naturally occurring amino acid.
<220> FEATURE:
<221> NAME/KEY: MISC_FEATURE
<222> LOCATION: (513)..(523)
<223> OTHER INFORMATION: Xaa can be any naturally occurring amino acid.
<220> FEATURE:
<221> NAME/KEY: MISC_FEATURE
<222> LOCATION: (525)..(528)
<223> OTHER INFORMATION: Xaa can be any naturally occurring amino acid.
<220> FEATURE:
<221> NAME/KEY: MISC_FEATURE
<222> LOCATION: (530)..(532)
<223> OTHER INFORMATION: Xaa can be any naturally occurring amino acid.
<220> FEATURE:
<221> NAME/KEY: MISC_FEATURE
<222> LOCATION: (534)..(534)
<223> OTHER INFORMATION: Xaa can be any naturally occurring amino acid.
<220> FEATURE:
<221> NAME/KEY: MISC_FEATURE
<222> LOCATION: (537)..(538)
<223> OTHER INFORMATION: Xaa can be any naturally occurring amino acid.
<220> FEATURE:
<221> NAME/KEY: MISC_FEATURE
<222> LOCATION: (540)..(544)
<223> OTHER INFORMATION: Xaa can be any naturally occurring amino acid.
<220> FEATURE:
<221> NAME/KEY: MISC_FEATURE
<222> LOCATION: (546)..(547)
<223> OTHER INFORMATION: Xaa can be any naturally occurring amino acid.
<220> FEATURE:
<221> NAME/KEY: misc_feature
<222> LOCATION: (549)..(549)
<223> OTHER INFORMATION: Xaa can be any naturally occurring amino acid
<220> FEATURE:
<221> NAME/KEY: MISC_FEATURE
<222> LOCATION: (551)..(552)
<223> OTHER INFORMATION: Xaa can be any naturally occurring amino acid.
<220> FEATURE:
<221> NAME/KEY: MISC_FEATURE
<222> LOCATION: (554)..(554)
<223> OTHER INFORMATION: Xaa can be any naturally occurring amino acid.
<220> FEATURE:
<221> NAME/KEY: MISC_FEATURE
<222> LOCATION: (556)..(556)
<223> OTHER INFORMATION: Xaa can be any naturally occurring amino acid.
```

```
<220> FEATURE:
<221> NAME/KEY: MISC_FEATURE
<222> LOCATION: (558)..(558)
<223> OTHER INFORMATION: Xaa can be any naturally occurring amino acid.
<220> FEATURE:
<221> NAME/KEY: MISC_FEATURE
<222> LOCATION: (561)..(562)
<223> OTHER INFORMATION: Xaa can be any naturally occurring amino acid.
<220> FEATURE:
<221> NAME/KEY: MISC_FEATURE
<222> LOCATION: (564)..(565)
<223> OTHER INFORMATION: Xaa can be any naturally occurring amino acid.
<220> FEATURE:
<221> NAME/KEY: MISC_FEATURE
<222> LOCATION: (567)..(568)
<223> OTHER INFORMATION: Xaa can be any naturally occurring amino acid.
<220> FEATURE:
<221> NAME/KEY: MISC_FEATURE
<222> LOCATION: (570)..(571)
<223> OTHER INFORMATION: Xaa can be any naturally occurring amino acid.
<220> FEATURE:
<221> NAME/KEY: MISC_FEATURE
<222> LOCATION: (573)..(573)
<223> OTHER INFORMATION: Xaa can be any naturally occurring amino acid.
<220> FEATURE:
<221> NAME/KEY: MISC_FEATURE
<222> LOCATION: (576)..(576)
<223> OTHER INFORMATION: Xaa can be any naturally occurring amino acid.
<220> FEATURE:
<221> NAME/KEY: misc_feature
<222> LOCATION: (578)..(578)
<223> OTHER INFORMATION: Xaa can be any naturally occurring amino acid
<220> FEATURE:
<221> NAME/KEY: MISC_FEATURE
<222> LOCATION: (582)..(582)
<223> OTHER INFORMATION: Xaa can be any naturally occurring amino acid.
<220> FEATURE:
<221> NAME/KEY: MISC_FEATURE
<222> LOCATION: (585)..(592)
<223> OTHER INFORMATION: Xaa can be any naturally occurring amino acid.
<220> FEATURE:
<221> NAME/KEY: MISC_FEATURE
<222> LOCATION: (594)..(597)
<223> OTHER INFORMATION: Xaa can be any naturally occurring amino acid.
<220> FEATURE:
<221> NAME/KEY: MISC_FEATURE
<222> LOCATION: (599)..(599)
<223> OTHER INFORMATION: Xaa can be any naturally occurring amino acid.
<220> FEATURE:
<221> NAME/KEY: MISC_FEATURE
<222> LOCATION: (602)..(602)
<223> OTHER INFORMATION: Xaa can be any naturally occurring amino acid.
<220> FEATURE:
<221> NAME/KEY: MISC_FEATURE
<222> LOCATION: (604)..(604)
<223> OTHER INFORMATION: Xaa can be any naturally occurring amino acid.
<220> FEATURE:
<221> NAME/KEY: MISC_FEATURE
<222> LOCATION: (606)..(606)
<223> OTHER INFORMATION: Xaa can be any naturally occurring amino acid.
<220> FEATURE:
<221> NAME/KEY: MISC_FEATURE
<222> LOCATION: (609)..(623)
<223> OTHER INFORMATION: Xaa can be any naturally occurring amino acid.
<220> FEATURE:
<221> NAME/KEY: MISC_FEATURE
<222> LOCATION: (625)..(626)
<223> OTHER INFORMATION: Xaa can be any naturally occurring amino acid.
<220> FEATURE:
<221> NAME/KEY: MISC_FEATURE
<222> LOCATION: (629)..(660)
<223> OTHER INFORMATION: Xaa can be any naturally occurring amino acid.
<220> FEATURE:
<221> NAME/KEY: MISC_FEATURE
<222> LOCATION: (663)..(714)
<223> OTHER INFORMATION: Xaa can be any naturally occurring amino acid.
<220> FEATURE:
<221> NAME/KEY: MISC_FEATURE
<222> LOCATION: (716)..(716)
```

```
<223> OTHER INFORMATION: Xaa can be any naturally occurring amino acid.
<220> FEATURE:
<221> NAME/KEY: MISC_FEATURE
<222> LOCATION: (718)..(723)
<223> OTHER INFORMATION: Xaa can be any naturally occurring amino acid.
<220> FEATURE:
<221> NAME/KEY: MISC_FEATURE
<222> LOCATION: (725)..(725)
<223> OTHER INFORMATION: Xaa can be any naturally occurring amino acid.
<220> FEATURE:
<221> NAME/KEY: MISC_FEATURE
<222> LOCATION: (727)..(735)
<223> OTHER INFORMATION: Xaa can be any naturally occurring amino acid.
<220> FEATURE:
<221> NAME/KEY: misc_feature
<222> LOCATION: (737)..(737)
<223> OTHER INFORMATION: Xaa can be any naturally occurring amino acid
<220> FEATURE:
<221> NAME/KEY: MISC_FEATURE
<222> LOCATION: (740)..(740)
<223> OTHER INFORMATION: Xaa can be any naturally occurring amino acid.
<220> FEATURE:
<221> NAME/KEY: MISC_FEATURE
<222> LOCATION: (742)..(743)
<223> OTHER INFORMATION: Xaa can be any naturally occurring amino acid.
<220> FEATURE:
<221> NAME/KEY: MISC_FEATURE
<222> LOCATION: (745)..(745)
<223> OTHER INFORMATION: Xaa can be any naturally occurring amino acid.
<220> FEATURE:
<221> NAME/KEY: MISC_FEATURE
<222> LOCATION: (750)..(750)
<223> OTHER INFORMATION: Xaa can be any naturally occurring amino acid.
<220> FEATURE:
<221> NAME/KEY: MISC_FEATURE
<222> LOCATION: (752)..(757)
<223> OTHER INFORMATION: Xaa can be any naturally occurring amino acid.
<220> FEATURE:
<221> NAME/KEY: MISC_FEATURE
<222> LOCATION: (763)..(789)
<223> OTHER INFORMATION: Xaa can be any naturally occurring amino acid.
<220> FEATURE:
<221> NAME/KEY: MISC_FEATURE
<222> LOCATION: (792)..(793)
<223> OTHER INFORMATION: Xaa can be any naturally occurring amino acid.
<220> FEATURE:
<221> NAME/KEY: misc_feature
<222> LOCATION: (795)..(796)
<223> OTHER INFORMATION: Xaa can be any naturally occurring amino acid
<220> FEATURE:
<221> NAME/KEY: MISC_FEATURE
<222> LOCATION: (801)..(801)
<223> OTHER INFORMATION: Xaa can be any naturally occurring amino acid.
<220> FEATURE:
<221> NAME/KEY: MISC_FEATURE
<222> LOCATION: (806)..(806)
<223> OTHER INFORMATION: Xaa can be any naturally occurring amino acid.
<220> FEATURE:
<221> NAME/KEY: MISC_FEATURE
<222> LOCATION: (808)..(816)
<223> OTHER INFORMATION: Xaa can be any naturally occurring amino acid.
<220> FEATURE:
<221> NAME/KEY: MISC_FEATURE
<222> LOCATION: (823)..(824)
<223> OTHER INFORMATION: Xaa can be any naturally occurring amino acid.
<220> FEATURE:
<221> NAME/KEY: MISC_FEATURE
<222> LOCATION: (827)..(829)
<223> OTHER INFORMATION: Xaa can be any naturally occurring amino acid.
<220> FEATURE:
<221> NAME/KEY: MISC_FEATURE
<222> LOCATION: (831)..(842)
<223> OTHER INFORMATION: Xaa can be any naturally occurring amino acid.
<220> FEATURE:
<221> NAME/KEY: MISC_FEATURE
<222> LOCATION: (844)..(848)
<223> OTHER INFORMATION: Xaa can be any naturally occurring amino acid.
<220> FEATURE:
<221> NAME/KEY: MISC_FEATURE
```

```
<222> LOCATION: (850)..(855)
<223> OTHER INFORMATION: Xaa can be any naturally occurring amino acid.
<220> FEATURE:
<221> NAME/KEY: MISC_FEATURE
<222> LOCATION: (858)..(858)
<223> OTHER INFORMATION: Xaa can be any naturally occurring amino acid.
<220> FEATURE:
<221> NAME/KEY: misc_feature
<222> LOCATION: (862)..(862)
<223> OTHER INFORMATION: Xaa can be any naturally occurring amino acid
<220> FEATURE:
<221> NAME/KEY: MISC_FEATURE
<222> LOCATION: (865)..(865)
<223> OTHER INFORMATION: Xaa can be any naturally occurring amino acid.
<220> FEATURE:
<221> NAME/KEY: misc_feature
<222> LOCATION: (867)..(867)
<223> OTHER INFORMATION: Xaa can be any naturally occurring amino acid
<220> FEATURE:
<221> NAME/KEY: MISC_FEATURE
<222> LOCATION: (874)..(876)
<223> OTHER INFORMATION: Xaa can be any naturally occurring amino acid.
<220> FEATURE:
<221> NAME/KEY: MISC_FEATURE
<222> LOCATION: (882)..(884)
<223> OTHER INFORMATION: Xaa can be any naturally occurring amino acid.
<220> FEATURE:
<221> NAME/KEY: MISC_FEATURE
<222> LOCATION: (889)..(889)
<223> OTHER INFORMATION: Xaa can be any naturally occurring amino acid.
<220> FEATURE:
<221> NAME/KEY: MISC_FEATURE
<222> LOCATION: (893)..(893)
<223> OTHER INFORMATION: Xaa can be any naturally occurring amino acid.
<220> FEATURE:
<221> NAME/KEY: MISC_FEATURE
<222> LOCATION: (896)..(896)
<223> OTHER INFORMATION: Xaa can be any naturally occurring amino acid.
<220> FEATURE:
<221> NAME/KEY: MISC_FEATURE
<222> LOCATION: (898)..(898)
<223> OTHER INFORMATION: Xaa can be any naturally occurring amino acid.
<220> FEATURE:
<221> NAME/KEY: MISC_FEATURE
<222> LOCATION: (900)..(908)
<223> OTHER INFORMATION: Xaa can be any naturally occurring amino acid.
<220> FEATURE:
<221> NAME/KEY: MISC_FEATURE
<222> LOCATION: (910)..(911)
<223> OTHER INFORMATION: Xaa can be any naturally occurring amino acid.
<220> FEATURE:
<221> NAME/KEY: MISC_FEATURE
<222> LOCATION: (915)..(915)
<223> OTHER INFORMATION: Xaa can be any naturally occurring amino acid.
<220> FEATURE:
<221> NAME/KEY: MISC_FEATURE
<222> LOCATION: (918)..(918)
<223> OTHER INFORMATION: Xaa can be any naturally occurring amino acid.
<220> FEATURE:
<221> NAME/KEY: misc_feature
<222> LOCATION: (922)..(922)
<223> OTHER INFORMATION: Xaa can be any naturally occurring amino acid
<220> FEATURE:
<221> NAME/KEY: MISC_FEATURE
<222> LOCATION: (927)..(927)
<223> OTHER INFORMATION: Xaa can be any naturally occurring amino acid.
<220> FEATURE:
<221> NAME/KEY: MISC_FEATURE
<222> LOCATION: (929)..(930)
<223> OTHER INFORMATION: Xaa can be any naturally occurring amino acid.
<220> FEATURE:
<221> NAME/KEY: MISC_FEATURE
<222> LOCATION: (932)..(932)
<223> OTHER INFORMATION: Xaa can be any naturally occurring amino acid.
<220> FEATURE:
<221> NAME/KEY: MISC_FEATURE
<222> LOCATION: (934)..(934)
<223> OTHER INFORMATION: Xaa can be any naturally occurring amino acid.
<220> FEATURE:
```

```
<221> NAME/KEY: MISC_FEATURE
<222> LOCATION: (937)..(937)
<223> OTHER INFORMATION: Xaa can be any naturally occurring amino acid.
<220> FEATURE:
<221> NAME/KEY: MISC_FEATURE
<222> LOCATION: (941)..(941)
<223> OTHER INFORMATION: Xaa can be any naturally occurring amino acid.
<220> FEATURE:
<221> NAME/KEY: MISC_FEATURE
<222> LOCATION: (946)..(946)
<223> OTHER INFORMATION: Xaa can be any naturally occurring amino acid.
<220> FEATURE:
<221> NAME/KEY: MISC_FEATURE
<222> LOCATION: (948)..(971)
<223> OTHER INFORMATION: Xaa can be any naturally occurring amino acid.
<220> FEATURE:
<221> NAME/KEY: MISC_FEATURE
<222> LOCATION: (973)..(992)
<223> OTHER INFORMATION: Xaa can be any naturally occurring amino acid.

<400> SEQUENCE: 40

Xaa Xaa Xaa Xaa Met Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Leu Leu Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Asn Xaa Xaa Xaa Xaa Xaa Xaa Xaa Xaa Xaa Xaa
        115                 120                 125

Xaa Xaa Xaa Xaa Xaa Xaa Xaa Xaa Xaa Ile Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Gly Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Ile Xaa Xaa Xaa Xaa Xaa Xaa Xaa Xaa Xaa
        195                 200                 205

Xaa Tyr Xaa Xaa Leu Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa
225                 230                 235                 240

Asn Xaa Xaa Xaa Gly Xaa Val Pro Xaa Xaa Xaa Xaa Leu Xaa Xaa
                245                 250                 255

Leu Xaa Xaa Xaa Xaa Met Xaa Xaa Xaa Xaa Xaa Gly Xaa Ile Pro
            260                 265                 270

Xaa Xaa Leu Xaa Xaa Leu Xaa Xaa Leu Xaa Xaa Leu Xaa Leu Xaa
        275                 280                 285

Asn Xaa Xaa Xaa Gly Xaa Ile Pro Xaa Xaa Xaa Xaa Xaa Xaa Xaa
    290                 295                 300
```

```
Leu Xaa Xaa Xaa Xaa Xaa Ser Xaa Asn Xaa Xaa Thr Gly Xaa Ile Pro
305                 310                 315                 320

Xaa Xaa Xaa Xaa

```
                        725                 730                 735
Xaa Ile Gly Xaa Gly Xaa Xaa Gly Xaa Val Tyr Arg Gly Xaa Met Xaa
            740                 745                 750

Xaa Xaa Xaa Xaa Xaa Val Ala Ile Lys Arg Xaa Xaa Xaa Xaa Xaa Xaa
        755                 760                 765

Xaa Xaa Xaa Xaa Xaa Xaa Xaa Xaa Xaa Xaa Xaa Xaa Xaa Xaa Xaa Xaa
    770                 775                 780

Xaa Xaa Xaa Xaa Xaa Glu Ile Xaa Xaa Leu Xaa Xaa Ile Arg His Arg
785                 790                 795                 800

Xaa Ile Val Arg Leu Xaa Gly Xaa Xaa Xaa Xaa Xaa Xaa Xaa Xaa Xaa
            805                 810                 815

Leu Leu Tyr Glu Tyr Met Xaa Xaa Gly Leu Xaa Xaa Xaa Leu Xaa Xaa
                820                 825                 830

Xaa Xaa Xaa Xaa Xaa Xaa Xaa Xaa Xaa Trp Xaa Xaa Xaa Xaa Xaa
        835                 840                 845

Val Xaa Xaa Xaa Xaa Xaa Xaa Gly Leu Xaa Tyr Leu His Xaa Asp Cys
850                 855                 860

Xaa Pro Xaa Ile Leu His Arg Asp Val Xaa Xaa Xaa Asn Ile Leu Leu
865                 870                 875                 880

Asp Xaa Xaa Xaa Glu Ala His Val Xaa Asp Phe Gly Xaa Ala Lys Xaa
            885                 890                 895

Leu Xaa Leu Xaa Xaa Xaa Xaa Xaa Xaa Xaa Xaa Ser Xaa Xaa Ala
        900                 905                 910

Gly Ser Xaa Gly Tyr Xaa Ala Pro Glu Xaa Ala Tyr Thr Leu Xaa Val
            915                 920                 925

Xaa Xaa Lys Xaa Asp Xaa Tyr Ser Xaa Gly Val Val Xaa Leu Glu Leu
        930                 935                 940

Ile Xaa Gly Xaa Xaa Xaa Xaa Xaa Xaa Xaa Xaa Xaa Xaa Xaa Xaa Xaa
945                 950                 955                 960

Xaa Xaa Xaa Xaa Xaa Xaa Xaa Xaa Xaa Xaa Xaa Ile Xaa Xaa Xaa Xaa
                965                 970                 975

Xaa Xaa Xaa Xaa Xaa Xaa Xaa Xaa Xaa Xaa Xaa Xaa Xaa Xaa Xaa
        980                 985                 990

<210> SEQ ID NO 41
<211> LENGTH: 22
<212> TYPE: DNA
<213> ORGANISM: Artificial Sequence
<220> FEATURE:
<223> OTHER INFORMATION: Synthetic forward primer for CLE41 derived from
      Arabidopsis thaliana.

<400> SEQUENCE: 41
caccatggca acatcaaatg ac                                             22

<210> SEQ ID NO 42
<211> LENGTH: 20
<212> TYPE: DNA
<213> ORGANISM: Artificial Sequence
<220> FEATURE:
<223> OTHER INFORMATION: Synthetic reverse primer for CLE41 derived from
      Arabidopsis thaliana.

<400> SEQUENCE: 42
aaaccagatg tgccaactca                                                20

<210> SEQ ID NO 43
<211> LENGTH: 22
```

```
<212> TYPE: DNA
<213> ORGANISM: Artificial Sequence
<220> FEATURE:
<223> OTHER INFORMATION: Synthetic forward primer for CLE42 derived from
      Arabidopsis thaliana.

<400> SEQUENCE: 43
caccatgaga tctcctcaca tc                                              22

<210> SEQ ID NO 44
<211> LENGTH: 24
<212> TYPE: DNA
<213> ORGANISM: Artificial Sequence
<220> FEATURE:
<223> OTHER INFORMATION: Synthetic reverse primer for CLE42 derived from
      Arabidopsis thaliana.

<400> SEQUENCE: 44
tgaatcaaac aagcaacata acaa                                            24

<210> SEQ ID NO 45
<211> LENGTH: 22
<212> TYPE: DNA
<213> ORGANISM: Artificial Sequence
<220> FEATURE:
<223> OTHER INFORMATION: Synthetic forward primer for PXY construct
      derived from Arabidopsis thaliana.

<400> SEQUENCE: 45
caccttaaat ccaccattgt ca                                              22

<210> SEQ ID NO 46
<211> LENGTH: 20
<212> TYPE: DNA
<213> ORGANISM: Artificial Sequence
<220> FEATURE:
<223> OTHER INFORMATION: Synthetic reverse primer for PXY construct
      derived from Arabidopsis thaliana.

<400> SEQUENCE: 46
ccaagataat ggacgccaac                                                 20

<210> SEQ ID NO 47
<211> LENGTH: 23
<212> TYPE: DNA
<213> ORGANISM: Artificial Sequence
<220> FEATURE:
<223> OTHER INFORMATION: Synthetic forward primer for SUC2::CLE41
      overlap PCR entry clone derived from Arabidopsis thaliana.

<400> SEQUENCE: 47
caccaacaca tgttgccgag tca                                             23

<210> SEQ ID NO 48
<211> LENGTH: 42
<212> TYPE: DNA
<213> ORGANISM: Artificial Sequence
<220> FEATURE:
<223> OTHER INFORMATION: Synthetic forward primer for SUC2::CLE41
      overlap PCR entry clone derived from Arabidopsis thaliana.

<400> SEQUENCE: 48
gtcatttgat gttgccatga aatttctttg agagggtttt tg                        42

<210> SEQ ID NO 49
<211> LENGTH: 42
<212> TYPE: DNA
```

```
<213> ORGANISM: Artificial Sequence
<220> FEATURE:
<223> OTHER INFORMATION: Synthetic reverse primer for CLE41 overlap PCR
      entry clone derived from Arabidopsis thaliana.

<400> SEQUENCE: 49
caaaaaccct ctcaaagaaa tttcatggca acatcaaatg ac                          42

<210> SEQ ID NO 50
<211> LENGTH: 20
<212> TYPE: DNA
<213> ORGANISM: Artificial Sequence
<220> FEATURE:
<223> OTHER INFORMATION: Synthetic forward primer for CLE41 RT-PCR
      derived from Arabidopsis thaliana.

<400> SEQUENCE: 50
ccatgactcg tcatcagtcc                                                   20

<210> SEQ ID NO 51
<211> LENGTH: 21
<212> TYPE: DNA
<213> ORGANISM: Artificial Sequence
<220> FEATURE:
<223> OTHER INFORMATION: Synthetic reverse primer for CLE41 RT-PCR
      derived from Arabidopsis thaliana.

<400> SEQUENCE: 51
tttggaccac taggaacctc a                                                 21

<210> SEQ ID NO 52
<211> LENGTH: 20
<212> TYPE: DNA
<213> ORGANISM: Artificial Sequence
<220> FEATURE:
<223> OTHER INFORMATION: Synthetic forward primer for CLE42 RT-PCR
      derived from Arabidopsis thaliana.

<400> SEQUENCE: 52
tccaaaccca tcaaagaacc                                                   20

<210> SEQ ID NO 53
<211> LENGTH: 20
<212> TYPE: DNA
<213> ORGANISM: Artificial Sequence
<220> FEATURE:
<223> OTHER INFORMATION: Synthetic reverse primer for CLE42 RT-PCR
      derived from Arabidopsis thaliana.

<400> SEQUENCE: 53
attggcaccg atcatctttc                                                   20

<210> SEQ ID NO 54
<211> LENGTH: 23
<212> TYPE: DNA
<213> ORGANISM: Artificial Sequence
<220> FEATURE:
<223> OTHER INFORMATION: Synthetic primer for CLE42 RT-PCR derived from
      Arabidopsis thaliana.

<400> SEQUENCE: 54
aacctagcaa tatcctcctc gac                                               23

<210> SEQ ID NO 55
<211> LENGTH: 20
<212> TYPE: DNA
<213> ORGANISM: Artificial Sequence
```

```
<220> FEATURE:
<223> OTHER INFORMATION: Synthetic reverse primer for PXY RT-PCR derived
      from Arabidopsis thaliana.

<400> SEQUENCE: 55
ggttccaccg atcttttcc                                                      20

<210> SEQ ID NO 56
<211> LENGTH: 21
<212> TYPE: DNA
<213> ORGANISM: Artificial Sequence
<220> FEATURE:
<223> OTHER INFORMATION: Synthetic forward primer for RT-PCR control
      derived from Arabidopsis thaliana.

<400> SEQUENCE: 56
atgaagatta aggtcgtggc a                                                   21

<210> SEQ ID NO 57
<211> LENGTH: 19
<212> TYPE: DNA
<213> ORGANISM: Artificial Sequence
<220> FEATURE:
<223> OTHER INFORMATION: Synthetic reverse primer for RT-PCR control
      derived from Arabidopsis thaliana.

<400> SEQUENCE: 57
ccgagtttga agaggctac                                                      19

<210> SEQ ID NO 58
<211> LENGTH: 20
<212> TYPE: DNA
<213> ORGANISM: Artificial Sequence
<220> FEATURE:
<223> OTHER INFORMATION: Synthetic forward primer for CLE41 qRT-PCR
      derived from Arabidopsis thaliana.

<400> SEQUENCE: 58
tcaagagggt tctcctcgaa                                                     20

<210> SEQ ID NO 59
<211> LENGTH: 20
<212> TYPE: DNA
<213> ORGANISM: Artificial Sequence
<220> FEATURE:
<223> OTHER INFORMATION: Synthetic reverse primer for CLE41 qRT-PCR
      derived from Arabidopsis thaliana.

<400> SEQUENCE: 59
tgtgctagcc tttggacgta                                                     20

<210> SEQ ID NO 60
<211> LENGTH: 20
<212> TYPE: DNA
<213> ORGANISM: Artificial Sequence
<220> FEATURE:
<223> OTHER INFORMATION: Synthetic forward primer to 18s rRNA qRT-PCR
      control derived from Arabidopsis thaliana.

<400> SEQUENCE: 60
catcagctcg cgttgactac                                                     20

<210> SEQ ID NO 61
<211> LENGTH: 19
<212> TYPE: DNA
<213> ORGANISM: Artificial Sequence
<220> FEATURE:
```

```
<223> OTHER INFORMATION: Synthetic reverse primer to 18s rRNA qRT-PCR
      control derived from Arabidopsis thaliana.

<400> SEQUENCE: 61
gatccttccg caggttcac                                                    19

<210> SEQ ID NO 62
<211> LENGTH: 20
<212> TYPE: DNA
<213> ORGANISM: Artificial Sequence
<220> FEATURE:
<223> OTHER INFORMATION: Synthetic forward primer to 35S for Genotyping
      derived from Arabidopsis thaliana.

<400> SEQUENCE: 62
cgcacaatcc cactatcctt                                                   20

<210> SEQ ID NO 63
<211> LENGTH: 21
<212> TYPE: DNA
<213> ORGANISM: Artificial Sequence
<220> FEATURE:
<223> OTHER INFORMATION: Synthetic reverse primer to pxy-3 for
      Genotyping derived from Arabidopsis thaliana.

<400> SEQUENCE: 63
ttaccgtttg atccaagctt g                                                 21
```

METHOD FOR THE ALTERATION OF PLANTS USING CLE POLYPEPTIDES/PEPTIDES

CROSS-REFERENCE TO RELATED APPLICATIONS

This application is a continuation of U.S. Ser. No. 13/062,916, filed Mar. 8, 2011, currently pending, which is the National Phase of International Application PCT/GB2009/051153, filed Sep. 9, 2009, which designated the United States and that International Application was published under PCT Article 12(2) in English. This application includes a claim of priority under 35 U.SC. § 119(a) and § 365(b) to British patent application No. GB 0816461.8 filed Sep. 9, 2008.

FIELD OF THE INVENTION

The present invention relates to manipulating the growth and/or structure of a plant through modulation of the amount of CLE41 and/or CLE42 expressed in the plant, and additionally or alternatively, modulating the amount of PXY in the plant. Manipulating the growth and/or structure of a plant can be used to alter the mechanical properties of a plant or plant derived product, or to maximise its potential for the production of plant derived products such as biofuels and paper.

BACKGROUND

In multi-cellular organisms, cells must communicate with each other in order for growth and development to occur in an ordered manner. In animals, it has long been known that polypeptides act as signalling molecules in mediating communication between cells, a common example being insulin in humans. These signalling molecules are responsible for initiating many cellular processes, typically by binding to a receptor at the cell surface, which in turn transmits a message to inside the cell via downstream signalling proteins such as membrane associated protein kinases (MAPK), tyrosine phosphatases and Ras proteins. In the cell, the cell signalling pathway end-point is usually a transcription factor target, which mediates a change in gene expression in the cell, thus causing a change in the growth and/or development of the cell in response to the initial extracellular signal.

In plants, it is also known that cell signalling occurs, and this was thought to be mediated by plant hormones such as auxin and cytokinin. More recently, the discovery of systemin has shown that polypeptides also play a role in cell-signalling in plants. One of the largest families of signalling polypeptides identified in plants is the Clavata3 (clv3)/Endosperm Surrounding Region (ESR)-related (CLE) family. These proteins are the most highly characterised family of small polypeptides in plants. The *Arabidopsis thaliana* genome contains 32 CLE genes. Clv3 is the best characterised CLE family member which acts together with a receptor kinase (CLAVATA 1) to play a role in regulating the proliferation of cells in the shoot (apical) meristem. At present, however, most of the CLE family remain functionally undefined.

The CLE gene family has been shown to be present in a variety of other plant species (Jun et al Cell. Mol. Life. Sci. 65 743-755 (2008) and Frickey et al *BMC Plant Biology* 2008, 8:1 10.1186/1471-2229-8-1) including rice, maize, tomato and alfalfa.

The polypeptides encoded by the CLE genes share common characteristics. They are less than 15 kDa in mass and comprise a short stretch of hydrophobic amino acids at the amino terminus which serves to target the polypeptide to the secretory pathway. This conserved stretch of 14 amino acids is known as the CLE domain (Jun et al supra).

Higher plants show post-embryonic development at shoot and root tips, which are known as the apical meristems. Stem cells at these meristems produce cells which differentiate to become flower, leaf, stem or root cells. A loss-of-function mutant resulting in an excess of stem cells at the apical meristem suggests that Clv3 plays a role in regulation of growth and/or differentiation at the growing tip. Over expression of CLV3 results in loss of apical stem cells, thus post-embryonic above ground parts of the plant are lost. The signalling pathway which CLV3 regulates has been elucidated and is described in Jun et al (supra). This pathway is thought to be conserved amongst other plants species.

Shiu and Bleecker suggest that the CLE family is likely to coordinate with a group of plant receptors known as the leucine-rich-repeat receptor-like (LLR-RLK) kinases (PNAS 98 10763-10768 (2001)).

U.S. Pat. No. 7,179,963 describes a maize clv3-like nucleotide sequence, and its use in modulating plant development and differentiation. U.S. Pat. No. 7,335,760 discloses nucleic acid sequences for use in genetically modifying a plant to increase plant yield and the mass of the plant, for example for biofuel production.

Other CLE family members have been shown to inhibit cell differentiation. For example, Frickey et al (supra) have looked at the CLE family and suggested that CLE family members CLE41 and/or 42 may play a role in vascular development. Ito et al (Science Vol 313 842-845 (2006)) show that dodecapeptides are important in preventing vascular cell differentiation.

In contrast, however, Strabala et al (Plant Physiology vol. 140 1331-1344 (2006)) show that CLE41 and/or 42 are genuine expressed members of the CLE family. Although general over-expression of CLE42 throughout the plant results in a dwarf phenotype, Strabala et al report that CLE42 is likely to be a functionally redundant molecule.

The source of biomass in plants is their woody tissue, derived from the vascular meristems of the plant such as the cambium and procambium, which divide to form the phloem and xylem cells of the vascular tissue within the plant stems and roots. The cambium and procambium (collectively known as the vascular meristems) are growth zones which enable the plant to grow laterally, thus generating the majority of biomass. Enhancing lateral growth by genetically altering the rates of procambial or cambial cell division may lead to an increase in the plant biomass. This would provide an additional source of biomass for various industries dependent upon plant derived products, such as the biofuel or paper industries.

Increasing the yield of biomass of plants, for example for paper and fuel production has previously been done by breeding programs, but in recent years there is interest in the use of genetic manipulation or plant modification for such purposes.

The division of cells to form the vascular tissue is a highly ordered process. Prominent polarity of cells destined to become either phloem cells or xylem cells is observed, the latter eventually forming the woody tissue of the plant. Xylem is principally water transporting tissue of the plant, and together with phloem, forms a vascular network for the plant. The cells of the xylem which are principally responsible for carrying water are the tracheary elements, of which there are two types—tracheids and vessels.

However, whilst there has been much investigation into the regulation of growth at the apical meristems, there is less understanding of the growth of the vascular tissue. Fisher et al (Current Biology 17 1061-1066 (2007)) report a loss of function mutant in which the spatial organisation of the vascular tissue is lost and the xylem and phloem cells are interspersed. The mutant is in a gene named PXY, which encodes a receptor-like kinase.

Tracheary elements (TEs) are cells in the xylem that are highly specialized for transporting water and solutes up the plant. They are produced from xylem cells by a process which involves specification, enlargement, patterned cell wall deposition, programmed cell death and cell wall removal. This results in adjacent TEs being joined together to form a continuous network for water transport.

Jun et al (supra) disclose that the CLE domain of CLE41 is identical to Tracheal Element Differentiation Inhibitory Factor (TDIF), which has been shown to inhibit cell differentiation, and CLE42 differs by only one amino acid from the TDIF sequence. When exogenously applied to cell cultures, synthetic CLE41 and CLE42 suppressed the formation of tracheary element cells from the xylem (Ito et al, supra).

There remains a need for identification of genetic elements, the manipulation of which can be used to alter the growth and/or structure of the plant.

BRIEF SUMMARY OF THE INVENTION

In a first aspect the invention provides the use of a polypeptide selected from the group consisting of:
i) a CLE41 polypeptide;
ii) a CLE42 polypeptide;
iii) a polypeptide comprising an amino acid sequence that is at least 70% identical to the amino acid sequence of amino acids 124 to 137 of the consensus sequence of FIG. 10 (SEQ ID NO. 12);
iv) a polypeptide comprising an amino acid sequence that is at least 70% identical to the amino acid sequence of CLE41 of FIG. 13A (SEQ ID NO. 21) or CLE42 of FIG. 14A (SEQ ID NO. 23);
v) a polypeptide encoded by a nucleic acid molecule that is at least 70% identical to the nucleotide sequence of CLE41 of FIG. 13B (SEQ ID NO. 22) or CLE42 of FIG. 14B (SEQ ID NO. 24);
in the manipulation of plant growth and/or structure.

In a second aspect the invention provides the use of a nucleic acid molecule selected from the group consisting of:
i) a nucleic acid molecule that encodes a CLE41 polypeptide;
ii) a nucleic acid molecule that encodes a CLE42 polypeptide;
iii) a nucleic acid molecule that encodes a polypeptide comprising an amino acid sequence that is at least 70% identical to the amino acid sequence of amino acids 124 to 137 of the consensus sequence of FIG. 10 (SEQ ID NO. 12);
iv) a nucleic acid molecule which is at least 70% identical to the nucleotide sequence of CLE41 of FIG. 13B (SEQ ID NO. 22) or CLE42 of FIG. 14B (SEQ ID NO. 24);
v) a nucleic acid molecule that hybridizes under stringent conditions to the nucleotide sequence i) or ii)
in the manipulation of plant growth and/or structure.

Preferably, the use of the first or second aspect is use of the polypeptide or nucleic acid in combination with a nucleic acid molecule selected from the group consisting of:
i) a nucleic acid molecule that encodes a CLE41 receptor;
ii) a nucleic acid molecule that encodes a CLE42 receptor;
iii) a nucleic acid molecule that encodes a polypeptide comprising an amino acid sequence that is at least 70% identical to the consensus sequence of FIG. 12 (SEQ ID NO. 20), or a functional equivalent thereof;
iv) a nucleic acid molecule that is at least 70% identical to the nucleotide sequence of FIG. 15B (SEQ ID NO. 26) or 15C (SEQ ID NO. 27);
v) a nucleic acid molecule that is at least 70% identical to a nucleic acid molecule of i) or ii);
vi) a nucleic acid molecule that hybridizes under stringent conditions to the nucleotide sequence i) or ii).

Preferably, the use of the first or second aspect is use of the polypeptide or nucleic acid in combination with a polypeptide selected from the group consisting of:
i) a CLE41 receptor;
ii) a CLE42 receptor;
iii) a polypeptide comprising an amino acid sequence that is at least 70% identical to the consensus sequence of FIG. 12 (SEQ ID NO. 20), or a functional equivalent thereof
iv) a polypeptide comprising an amino acid sequence that is at least 70% identical to the PXY sequence of FIG. 15A (SEQ ID NO. 25);
v) a polypeptide sequence comprising an amino acid sequence which is at least 70% identical to a sequence encoding i) or ii);
vi) a polypeptide comprising an amino acid sequence encoded by a nucleic acid molecule that is at least 70% identical to the PXY nucleotide sequence of FIG. 15B (SEQ ID NO. 26) or 15C (SEQ ID NO. 27).

Preferably said CLE41 or CLE42 receptor is PXY or a functional equivalent thereof.

Preferably said manipulation of the plant growth and/or structure is an increase or decrease in the amount of growth and/or division of the procambial and/or cambial cells in a plant, specifically the number of cells generated. More specifically, it is an increase or decrease in the rate of division of such cells. Thus, the manipulation of growth and/or structure can be said to be an increase or decrease in the secondary growth of the plant, and/or an increase or decrease in the degree of organisation of the secondary structure, at the cellular level. By secondary growth is preferably meant the woody tissue of a plant, or the vascular or interfasicular tissue. Preferably, where there is an increase in the number of procambial and/or cambial cells, these cells differentiate into xylem and/or phloem cells, preferably the former.

In a further aspect, the present invention provides a method of manipulating the growth and/or structure of a plant, comprising modulating the level of CLE41 and/or CLE42 or a functional equivalent thereof, in the plant.

Preferably the levels of CLE41 and/or CLE42 are modulated by introducing into a cell of the plant:
i) a CLE41 polypeptide;
ii) a CLE42 polypeptide;
iii) a polypeptide comprising an amino acid sequence that is at least 70% identical to the amino acid sequence of amino acids 124 to 137 of the consensus sequence of FIG. 10 (SEQ ID NO. 12);
iv) a polypeptide comprising an amino acid sequence that is at least 70% identical to the amino acid sequence of CLE41 of FIG. 13A (SEQ ID NO. 21) or CLE42 of FIG. 14A (SEQ ID NO. 23);
v) a polypeptide encoded by a nucleic acid molecule that is at least 70% identical to the nucleotide sequence of CLE41 of FIG. 13B (SEQ ID NO. 22) or CLE42 of FIG. 14B (SEQ ID NO. 24).

Alternatively the levels of CLE41 and/or CLE42 are modulated by introducing into a cell of the plant:
  i) a nucleic acid molecule that encodes a CLE41 polypeptide;
  ii) a nucleic acid molecule that encodes a CLE42 polypeptide;
  iii) a nucleic acid molecule that encodes a polypeptide comprising an amino acid sequence that is at least 70% identical to the amino acid sequence of amino acids 124 to 137 of the consensus sequence of FIG. 10 (SEQ ID NO. 12);
  iv) a nucleic acid molecule which is at least 70% identical to the nucleotide sequence of CLE41 of FIG. 13B (SEQ ID NO. 22) or CLE42 of FIG. 14B (SEQ ID NO. 24);
  v) a nucleic acid molecule that hybridizes under stringent conditions to the nucleotide sequence i) or ii).

Preferably, the levels of levels of CLE41 and/or CLE42 or a functional equivalent thereof are upregulated.

Optionally, the method further comprises introducing into a cell of the plant:
  i) a nucleic acid molecule that encodes a CLE41 receptor;
  ii) a nucleic acid molecule that encodes a CLE42 receptor;
  iii) a nucleic acid molecule that encodes a polypeptide comprising an amino acid sequence that is at least 70% identical to the consensus sequence of FIG. 12 (SEQ ID NO. 20), or a functional equivalent thereof;
  iv) a nucleic acid molecule that is at least 70% identical to the nucleotide sequence of FIG. 15B (SEQ ID NO. 26) or 15C (SEQ ID NO. 27);
  v) a nucleic acid molecule that is at least 70% identical to a nucleic acid molecule of i) or ii);
  vi) a nucleic acid molecule that hybridizes under stringent conditions to the nucleotide sequence i) or ii).

Alternatively, the method further comprises introducing into cell of a plant:
  i) a CLE41 receptor;
  ii) a CLE42 receptor;
  iii) a polypeptide comprising an amino acid sequence that is at least 70% identical to the consensus sequence of FIG. 12 (SEQ ID NO. 20), or a functional equivalent thereof
  iv) a polypeptide comprising an amino acid sequence that is at least 70% identical to the PXY sequence of FIG. 15A (SEQ ID NO. 25);
  v) a polypeptide sequence comprising an amino acid sequence which is at least 70% identical to a sequence encoding i) or ii);
  vi) a polypeptide comprising an amino acid sequence encoded by a nucleic acid molecule that is at least 70% identical to the PXY nucleotide sequence of FIG. 15B (SEQ ID NO. 26) or 15C (SEQ ID NO. 27).

Preferably said CLE41 and/or CLE42 receptor is PXY or a functional equivalent thereof.

In aspects where the levels of two or more of CLE41, CLE42 and PXY are to be manipulated in a plant, this may be achieved by:
  (i) manipulating the levels of CLE41 and/or CLE42 as hereinbefore described, in a first plant;
  (ii) manipulating the levels of a CLE41 and/or CLE42 receptor as hereinbefore described, in a second plant;
  (iii) crossing said first and second plants to obtain a plant in which the levels of CLE41 and/or CLE42 and said receptor are manipulated. Also provided in the present invention is the plant produced by the crossing of the first and second plants, and progeny thereof which express the non-native nucleotide and/or polypeptide sequences.

In a further aspect, the present invention provides a plant cell manipulated to express:
  i) a CLE41 polypeptide;
  ii) a CLE42 polypeptide;
  iii) a polypeptide comprising an amino acid sequence that is at least 70% identical to the amino acid sequence of amino acids 124 to 137 of the consensus sequence of FIG. 10 (SEQ ID NO. 12);
  iv) a polypeptide comprising an amino acid sequence that is at least 70% identical to the amino acid sequence of CLE41 of FIG. 13A (SEQ ID NO. 21) or CLE42 of FIG. 14A (SEQ ID NO. 23);
  v) a polypeptide encoded by a nucleic acid molecule that is at least 70% identical to the nucleotide sequence of CLE41 of FIG. 13B (SEQ ID NO. 22) or CLE42 of FIG. 14B (SEQ ID NO. 24);
optionally in combination with expression of a receptor for CLE41 and/or CLE42.

In a further aspect, the present invention provides a plant cell manipulated to express
  i) a nucleic acid molecule that encodes a CLE41 polypeptide;
  ii) a nucleic acid molecule that encodes a CLE42 polypeptide;
  iii) a nucleic acid molecule that encodes a polypeptide comprising an amino acid sequence that is at least 70% identical to the amino acid sequence of amino acids 124 to 137 of the consensus sequence of FIG. 10 (SEQ ID NO. 12);
  iv) a nucleic acid molecule which is at least 70% identical to the nucleotide sequence of CLE41 of FIG. 13B (SEQ ID NO. 22) or CLE42 of FIG. 14B (SEQ ID NO. 24);
  v) a nucleic acid molecule that hybridizes under stringent conditions to the nucleotide sequence i) or ii).

Preferably, said plant cell is further manipulated to express a nucleic acid molecule selected from the group consisting of:
  i) a nucleic acid molecule that encodes a CLE41 receptor;
  ii) a nucleic acid molecule that encodes a CLE42 receptor;
  iii) a nucleic acid molecule that encodes a polypeptide comprising an amino acid sequence that is at least 70% identical to the consensus sequence of FIG. 12 (SEQ ID NO. 20), or a functional equivalent thereof;
  iv) a nucleic acid molecule that is at least 70% identical to the nucleotide sequence of FIG. 15B (SEQ ID NO. 26) or 15C (SEQ ID NO. 27);
  v) a nucleic acid molecule that is at least 70% identical to a nucleic acid molecule of i) or ii);
  vi) a nucleic acid molecule that hybridizes under stringent conditions to the nucleotide sequence i) or ii).

Alternatively, said plant cell is further manipulated to express a polypeptide selected from the group consisting of:
  i) a CLE41 receptor;
  ii) a CLE42 receptor;
  iii) a polypeptide comprising an amino acid sequence that is at least 70% identical to the consensus sequence of FIG. 12 (SEQ ID NO. 20), or a functional equivalent thereof iv) a polypeptide comprising an amino acid sequence that is at least 70% identical to the PXY sequence of FIG. 15A (SEQ ID NO. 25);
v) a polypeptide sequence comprising an amino acid sequence which is at least 70% identical to a sequence encoding i) or ii);
vi) a polypeptide comprising an amino acid sequence encoded by a nucleic acid molecule that is at least 70% identical to the PXY nucleotide sequence of FIG. 15B (SEQ ID NO. 26) or 15C (SEQ ID NO. 27).

Preferably said CLE41 and/or CLE42 receptor is PXY or a functional equivalent thereof.

In a further aspect, there is provided a nucleic acid molecule encoding a functional equivalent of PXY, preferably derived from *Arabidopsis thaliana*, poplar or rice, and more preferably encoding the amino acid sequence of the consensus sequence of FIG. 12 (SEQ ID NO. 20). Also provided is a polypeptide sequence encoding a functional equivalent of PXY, preferably derived from *Arabidopsis thaliana*, poplar or rice, and preferably comprising an amino acid sequence of the consensus sequence of FIG. 12 (SEQ ID NO. 20). Preferably, the amino acid sequence comprises the sequence of pttPXY, PXYL-1, PXYL-2 or Os02g02140.1, or Os03g05140.1 of FIG. 12 ((SEQ ID NOs. 16, 18, 19, 13 and 14 respectively). Also included are sequences having 70% sequence identity or sequence homology thereto.

It is apparent that the levels of CLE41, CLE42 and or a receptor thereof, such as PXY, in each of the aspects of the present invention may be manipulated by altering the expression of native CLE41, CLE42 and or a receptor thereof within the plant cell. This may be achieved by placing the native nucleotide sequence under the control of a nucleotide sequence which modifies expression of a native gene to allow modify expression thereof. The nucleotide sequence may be a regulatory sequence, as defined herein, or may encode a regulatory protein, such as a transcription factor, or may encode a DNA or RNA antisense sequence. As such, the nucleotide sequence or its expression product can modify expression, amount and/or activity of a native gene/polypeptide. Methods of function of such regulatory proteins, expression products and antisense will be known to persons skilled in the art.

In a yet further aspect, the present invention provides a plant comprising a cell according to the invention. Also provided are progeny of the plants of the invention.

In a further aspect, there is provided the use of a cell or plant of the invention in the production of a plant-derived product. A plant-derived product may include biomass, fibres, forage, biocomposites, biopolymers, wood, biofuel or paper. In addition, the invention provides the use of a cell or a plant of the invention in altering the mechanical properties of a plant or a plant derived product.

In a further aspect, the present invention provides a method of manipulating the growth and/or structure of a plant, comprising the steps of:
i) providing a cell/seed according to the invention;
ii) regenerating said cell/seed into a plant; and optionally
iii) monitoring the levels of CLE41 and/or CLE42 or a receptor thereof, and or PXY or functional equivalents thereof in said regenerated plant.

In a further aspect, there is provided an expression construct comprising a first nucleic acid sequence selected from the group consisting of:
i) a nucleic acid molecule that encodes a CLE41 polypeptide;
ii) a nucleic acid molecule that encodes a CLE42 polypeptide;
iii) a nucleic acid molecule that encodes a polypeptide comprising an amino acid sequence that is at least 70% identical to the amino acid sequence of amino acids 124 to 137 of the consensus sequence of FIG. 10 (SEQ ID NO. 12);
iv) a nucleic acid molecule which is at least 70% identical to the nucleotide sequence of CLE41 of FIG. 13B (SEQ ID NO. 22) or CLE42 of FIG. 14B (SEQ ID NO. 24);
v) a nucleic acid molecule that hybridizes under stringent conditions to the nucleotide sequence i) or ii);
and optionally a second nucleic sequence encoding a regulatory sequence capable of expressing the first nucleic sequence specifically in or adjacent to the vascular tissue of a plant.

Preferably, the regulatory sequence will be capable of directing expression of a nucleotide sequence specifically to the vascular tissue, preferably to the cambial/procambial cells and more preferably to tissue adjacent to the cambial/procambial cells i.e. the phloem and/or xylem tissue. Most preferably, a regulatory sequence used in the present invention will be capable of directing expression specifically to the phloem cells. Examples of suitable phloem specific regulatory sequences are SUC2 and APL, KAN1, KAN2, At4g33660, At3g61380, At1g79380. Xylem specific regulatory sequences may also be used in the present invention. Examples include REV, IRX1 COBL4, KOR, At2g38080, and At1g27440, the promoter sequence for the irregular xylem3 (irx3) (AtCESA7) gene, the promoter sequence for the irregular xylem7 (FRAGILE FIBER 8) gene, and the promoter sequence for the irregular xylem12 (*ARABIDOPSIS* LACCASE-LIKE MULTICOPPER OXIDASE 4) gene (Brown et al. The Plant Cell, Vol. 17, 2281-2295).

Optionally, the expression cassette may further comprise a third nucleic acid sequence selected from the group consisting of:
i) a nucleic acid molecule that encodes a CLE41 receptor;
ii) a nucleic acid molecule that encodes a CLE42 receptor;
iii) a nucleic acid molecule that encodes a polypeptide comprising an amino acid sequence that is at least 70% identical to the consensus sequence of FIG. 12 (SEQ ID NO. 20), or a functional equivalent thereof;
iv) a nucleic acid molecule that is at least 70% identical to the nucleotide sequence of FIG. 15B (SEQ ID NO. 26) or 15C (SEQ ID NO. 27);
v) a nucleic acid molecule that is at least 70% identical to a nucleic acid molecule of i) or ii);
vi) a nucleic acid molecule that hybridizes under stringent conditions to the nucleotide sequence i) or ii)

Preferably, the expression cassette comprises a nucleic acid encoding PXY or a functional equivalent thereof. The third nucleic acid sequence may be provided on the same expression cassette as the first and/or second nucleic acid sequence, or on a separate expression cassette to the first nucleic acid sequence. The third nucleic acid sequence may be under the control of fourth nucleic acid sequence encoding a regulatory sequence capable of expressing the third nucleic sequence specifically in or adjacent to the vascular tissue of a plant.

The second nucleic acid sequence may be the same or different to the fourth nucleic acid sequence.

In a further aspect, there is provided a host cell or organism comprising an expression construct of the invention.

According to a further aspect of the invention there is provided a transgenic plant seed comprising a cell according to the invention.

The present invention also provides a plant derived product produced by a method of the invention.

The present invention also provides a host cell or organism comprising an expression construct of the invention. A host cell or organism may be a plant cell, plant seed, plant, or other plant material.

The present a method of producing a plant-derived product comprising:
a) manipulating the growth and/or structure of a plant using the methods of the invention;
b) growing the plant until it reaches a pre-determined lateral size; optionally
c) harvesting the plant derived product of the plant.

A plant-derived product may include biomass, fibres, forage, biocomposites, biopolymers, wood, biofuel or paper.

The present invention also provides a method of altering the mechanical properties of a plant or plant derived product comprising:
a) manipulating the growth and/or structure of a plant using the methods of the invention;
b) growing the plant until it reaches a pre-determined size; and optionally
c) harvesting a plant derived product of the plant.

BRIEF DESCRIPTION OF THE DRAWINGS

FIGS. 3 and 4) have differentiated into xylem cells. 35S::CLE41 therefore has more xylem cells than wild type.

FIG. 3).

FIG. 12 is a comparison of the kinase domain of PXY (*Arabidopsis thaliana*) from proteins in rice (Os02g02140.1), poplar (PttPXY) and *Arabidopsis thaliana* (PXL1 and PXL2): Os02g02140 (SEQ ID NO. 13); Os03g05140 (SEQ ID NO. 14); OsPXY (SEQ ID NO. 15); PttPXY (SEQ ID NO. 16); PXY (SEQ ID NO. 17); PXL1 (SEQ ID NO. 18); PXL2 (SEQ ID NO. 19); and Consensus (SEQ ID NO. 20).

FIG. 13 shows the amino acid sequence of the CLE41 proteins (A) (SEQ ID NO. 21), and nucleotide sequence of the CLE41 gene (B) (SEQ ID NO. 22).

FIG. 14 shows the amino acid sequence of the CLE42 proteins (A) (SEQ ID NO 23) and nucleotide sequence of the CLE42 gene (B) (SEQ ID NO. 24).

FIG. 15 shows the amino acid sequence of the PXY proteins (A) (SEQ ID NO. 25). and nucleotide sequence of the PXY gene without (B) (SEQ ID NO. 26) or with (C) the intron (SEQ ID NO. 27).

FIG. 16A-F shows preferred promoter and terminator sequences for use in the invention: 16A: 1.35S promoter (SEQ ID NO. 28); 16B: IRX3 promoter (SEQ ID NO. 29); 16C: LRR promoter (SEQ ID NO. 30); 16D: Nodulin promoter (SEQ ID NO. 31); 16E: 1.35S terminator (SEQ ID NO. 32) and 16F NOS terminator (SEQ ID NO. 33).

Figure 18:
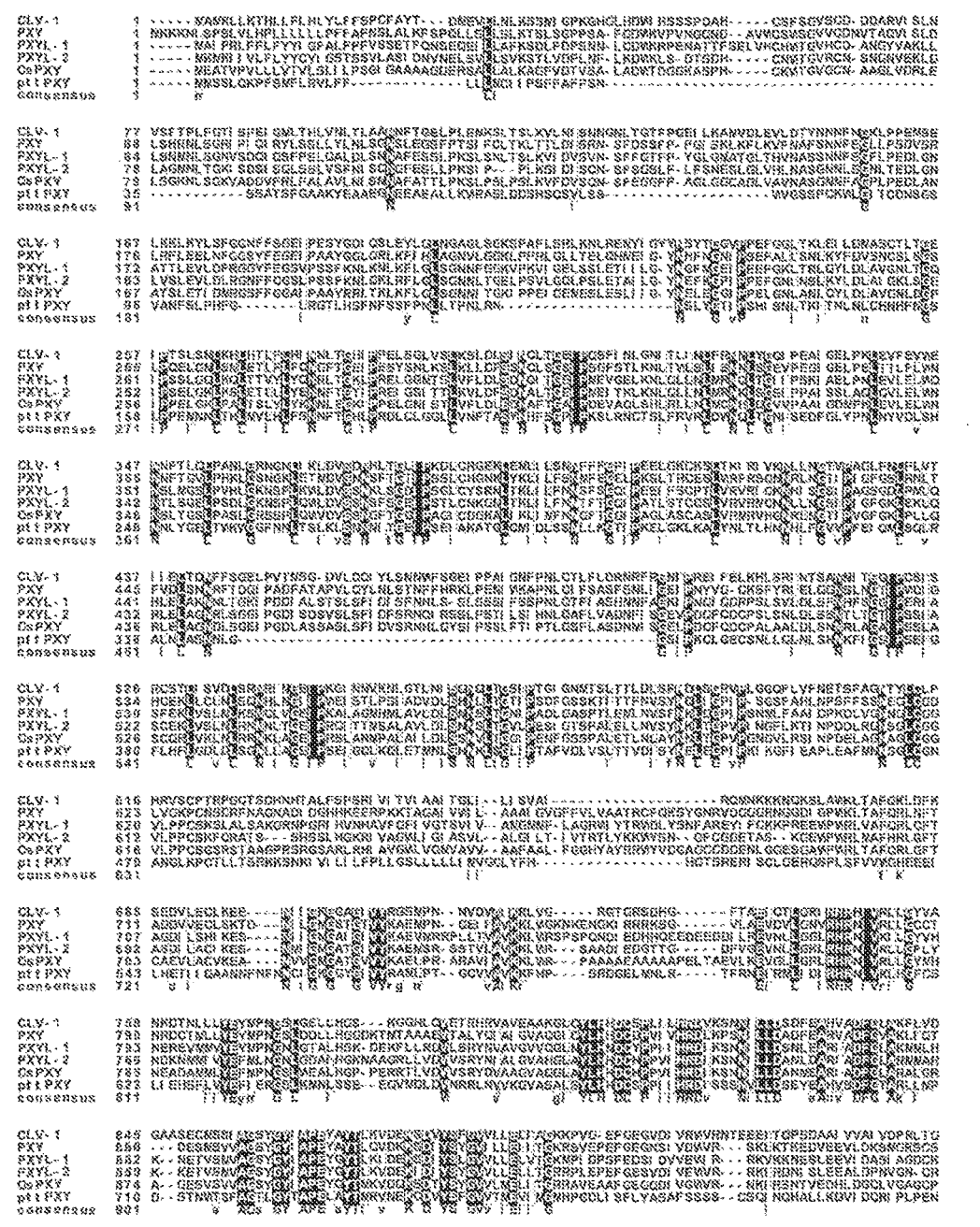
Figure 18:
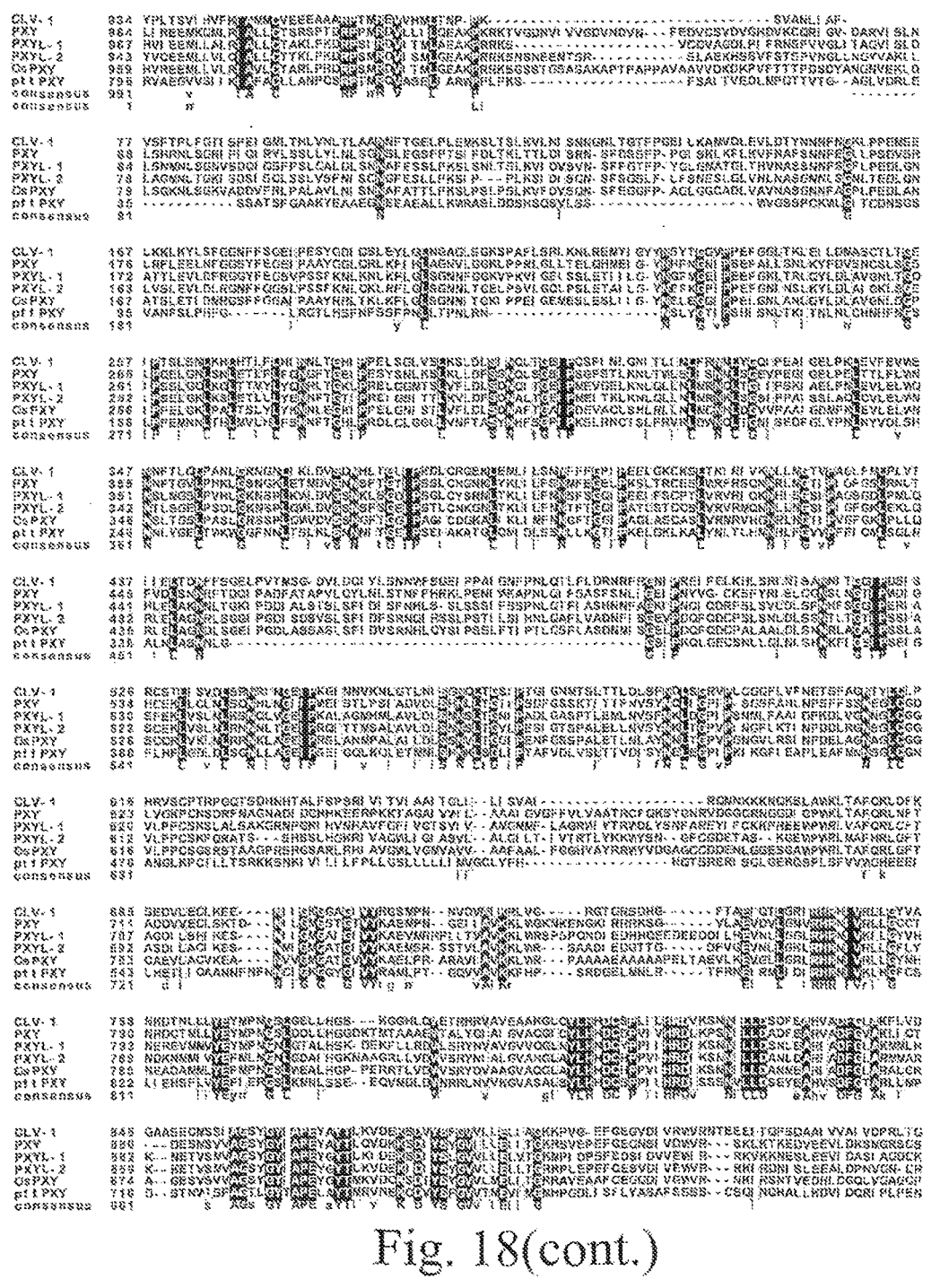

FIG. 18 is an alignment of full length PXY and related PXY proteins from poplar (PttPXY) and *Arabidopsis thaliana* (PXYL1 and 2): CLV-1 (SEQ ID NO. 34); PXY (SEQ ID NO. 35); PXYL-1 (SEQ ID NO. 36); PXYL-2 (SEQ ID NO. 37); OsPXY (SEQ ID NO. 38); PttPXY (SEQ ID NO. 39) and consensus (SEQ ID NO. 40).

FIG. 8 wild type). SUC2::CLE41 and SUC2::CLE41 35S::PXY plants have vascular tissue that is highly ordered with many more vascular cells than wild type.

DETAILED DESCRIPTION OF THE INVENTION

Figure 1:
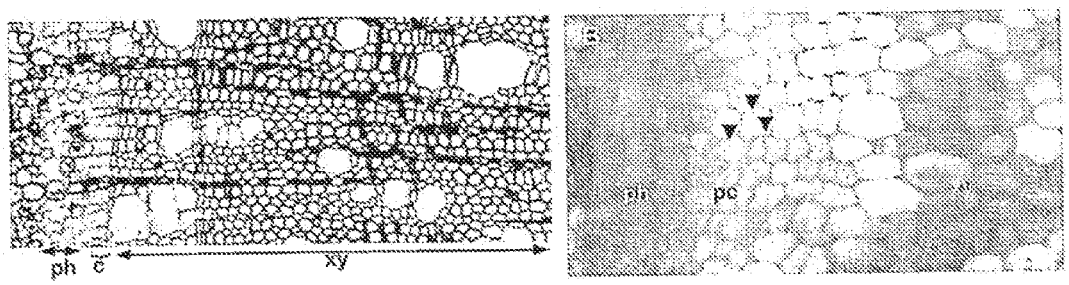
FIG. 1 shows the cambial meristem of birch (A) and *Arabidopsis* (B). (A) Transverse section of the growing cambium in Birch. (B) Cross section of a vascular bundle from an *Arabidopsis* stem. Phloem (ph), xylem (xy), procambium (pc) and cambium (c) are indicated.
Figure 2:
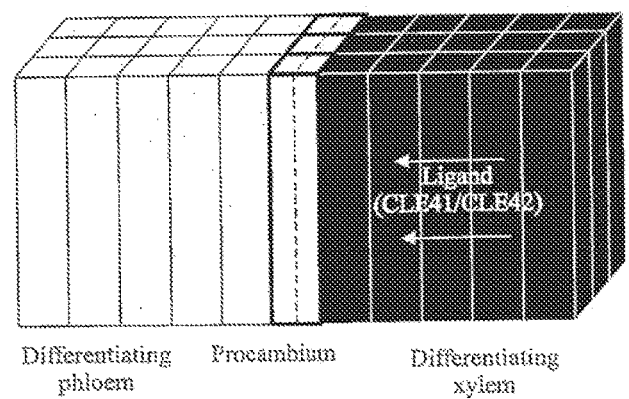
FIG. 2 is a diagrammatic representation of vascular development by the procambium (in, for example, *Aribidopsis*) or by the cambium (for example in trees such as birch). New cells arise from division of procambial cells that subsequently differentiate into the phloem of xylem. In this model a ligand expressed in the xylem signals cell division in the procambium.
Figure 3:
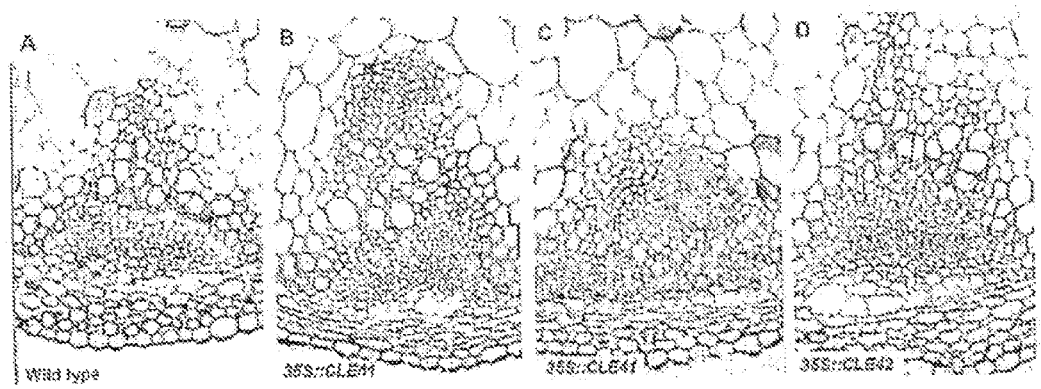
FIG. 3 shows the effects of over-expressing CLE41 (B,C) and CLE42 (D) on *Arabidopsis* vascular development compared to the wild type (A) in 35 day old plants. See also Table 1.
Figure 4:
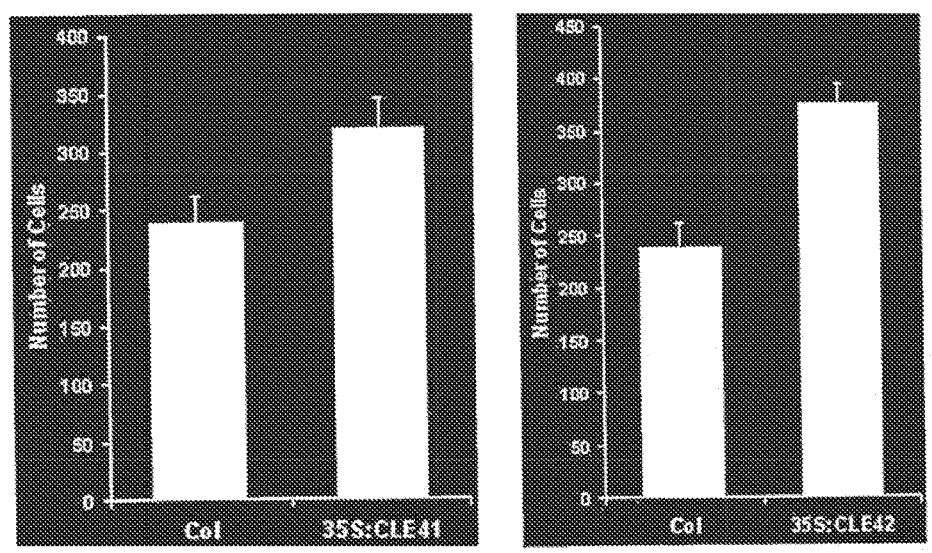
FIG. 4 is a graph showing the average number of cells in the vascular bundles of wild type compared to 35S::CLE41 and 35S::CLE42 *Arabidopsis* plants at 35 days.

The present invention is based upon the finding that CLE41 and CLE42 function as ligands for the transmembrane receptor kinase PXY in plants, and modify and/or initiate the regulatory pathway which controls cell division and differentiation in the vascular tissue of a plant. Thus, by modulating the levels of CLE41 and/or CLE42 in a plant, optionally in combination with PXY, the growth and/or structure of the plant can be manipulated, as hereinbefore described.

In particular, the present invention is based upon the finding that individual over-expression of CLE41 and/or CLE42 leads to an excess of undifferentiated cells in the vascular meristem and a subsequent increase in the radial thickness of the xylem. Further, over-expression of PXY or a functional equivalent thereof, together with a PXY ligand such as CLE41 and/or CLE42, results in an excess of undifferentiated cells in the vascular meristem of the plant, which show a highly ordered structure. This excess of cells in the vascular meristem have been shown to then differentiate into xylem cells, thus increasing the radial thickness of the xylem and the biomass of the plant.

A "non-essential" amino acid residue is a residue that can be altered from the wild-type sequence of without abolishing or, more preferably, without substantially altering a biological activity, whereas an "essential" amino acid residue results in such a change. For example, amino acid residues that are conserved among the polypeptides of the present invention, e.g., those present in the conserved potassium channel domain are predicted to be particularly non-amenable to alteration, except that amino acid residues in transmembrane domains can generally be replaced by other residues having approximately equivalent hydrophobicity without significantly altering activity.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in protein is preferably replaced with another amino acid residue from the same side chain family. Alternatively, in another embodiment, mutations can be introduced randomly along all or part of coding sequences, such as by saturation mutagenesis, and the resultant mutants can be screened for biological activity to identify mutants that retain activity. Following mutagenesis of a polypeptide, the encoded proteins can be expressed recombinantly and the activity of the protein can be determined.

As used herein, a "biologically active fragment" of protein includes fragment of protein that participate in an interaction between molecules and non-molecules. Biologically active portions of protein include peptides comprising amino acid sequences sufficiently homologous to or derived from the amino acid sequences of the protein, which include fewer amino acids than the full length protein, and exhibit at least one activity of protein. Typically, biologically active portions comprise a domain or motif with at least one activity of the protein, e.g., the ability to modulate membrane excitability, intracellular ion concentration, membrane polarization, and action potential.

As used herein, the term "nucleic acid molecule" includes DNA molecules (e.g., a cDNA or genomic DNA) and RNA molecules (e.g., a mRNA) and analogs of the DNA or RNA generated, e.g., by the use of nucleotide analogs. The nucleic acid molecule can be single-stranded or double-stranded, but preferably is double-stranded DNA. The nucleotide sequence may be RNA or DNA, including cDNA.

With regards to genomic DNA, the term "isolated" includes nucleic acid molecules that are separated from the chromosome with which the genomic DNA is naturally associated. Preferably, an "isolated" nucleic acid is free of sequences that naturally flank the nucleic acid (i.e., sequences located at the 5'- and/or 3'-ends of the nucleic acid) in the genomic DNA of the organism from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding protein, and can further include non-coding regulatory sequences and introns.

In the present invention, CLE41 and CLE42 are polypeptides comprising the amino acid sequence of FIG. 13A (SEQ ID NO. 21) or 14A (SEQ ID NO. 23), respectively. CLE41 and CLE42 are ligands which are able to activate a kinase receptor, and result in phosphorylation of itself or its target. References to CLE41 and/or CLE42 include functional equivalents thereof. By a functional equivalent of CLE41 or CLE42 is meant a polypeptide which is derived from the consensus sequence of FIG. 10 by addition, deletion or substitution of one or more amino acids, preferably non-essential amino acids. Preferably, a substitution is a conservative substitution. A functional equivalent of CLE41 and/or CLE42 for use in the present invention will be biologically active, and preferably have some or all of the desired biological activity of the native polypeptide, preferably the ability to bind to PXY or a functional equivalent thereof and regulate growth and/or differentiation of the vascular tissue. Preferably, the equivalent is a signalling protein, preferably of less than 15 kDa in mass, and preferably comprising a hydrophobic region at the amino terminus. Functional equivalents may exhibit altered binding characteristics to PXY compared to a native CLE41 and/or CLE42 protein, but will mediate the same downstream signalling pathway. Preferred functional equivalents may show reduced non-desirable biological activity compared to the native protein Preferably, the equivalent comprises a conserved region of 14 amino acids having a sequence which is at least 70% more preferably 80%, 85%, 90%, 95%, 96%, 97%, 98%, 99% or 100% identical to the conserved region of amino acids 124 to 137 of the consensus of FIG. 10 (SEQ ID NO. 12), and more preferably across the full length of the consensus sequence. A functional equivalent of CLE41 and/or CLE42 preferably also shares at least 50%, even more preferably at least 60%, and even more preferably at least 70%, 75%, 80%, 82%, 84%, 85%, 86%, 87%, 88%, 89%, 90%, 91%, 92%, 93%, 94%, 95%, 96%, 97%, 98%, 99%, or 100% sequence homology with CLE41 or CLE42. Preferably, a functional equivalent may also share sequence identity with the CLE41 and/or CLE42 sequence of FIGS. 13A (SEQ ID NO. 21) and 14A (SEQ ID NO. 23), respectively. Preferably, functional equivalents have at least preferably at least 50%, even more preferably at least 60%, and even more preferably at least 70%, 75%, 80%, 82%, 84%, 85%, 86%, 87%, 88%, 89%, 90%, 91%, 92%, 93%, 94%, 95%, 96%, 97%, 98%, 99%, or 100% % sequence identity with the amino acid sequence of FIGS. 13A (SEQ ID NO. 21) and 14A (SEQ ID NO. 23) respectively.

References to CLE41 and/or CLE42 also include fragments of the CLE41 and/or CLE42 polypeptides or their functional equivalents. A fragment is a portion of a polypeptide sequence, preferably which retains some or all of the biological activity of the full length sequence. Preferably, fragments of CLE41 and/or CLE42 retain the ability to bind PXY and regulate the growth and/or differentiation of the vascular tissue of a plant. Preferably, a fragment may be at least 7 amino acids in length, preferably at least 8, 9, or 10, 15, 20, 25, 30, 40, 50, 60, 70, 80, 90 or 100 amino acids in length, up to the full length CLE polypeptide. Most preferably, a fragment will comprise the conserved region consisting of amino acids 124 to 137 of the consensus sequence of FIG. 10 (SEQ ID NO. 12).

Figure 10:
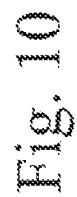
FIG. 10 is an alignment of rice, poplar and *Arabidopsis thaliana* putative PXY ligands: 1395 (SEQ ID NO. 1); 5110 (SEQ ID NO. 2); Cle41 (SEQ ID No. 3); Cle 44 (SEQ ID NO. 4); 148 (SEQ ID NO. 5); 1849 (SEQ ID NO. 6); 428 (SEQ ID NO. 7); Cle46 (SEQ ID NO. 8); OsCLE205 (SEQ ID NO. 9); Cle42 (SEQ ID NO. 10); OsCLE102 (SEQ ID NO. 11); and consensus (SEQ ID NO. 12).
Figure 11:
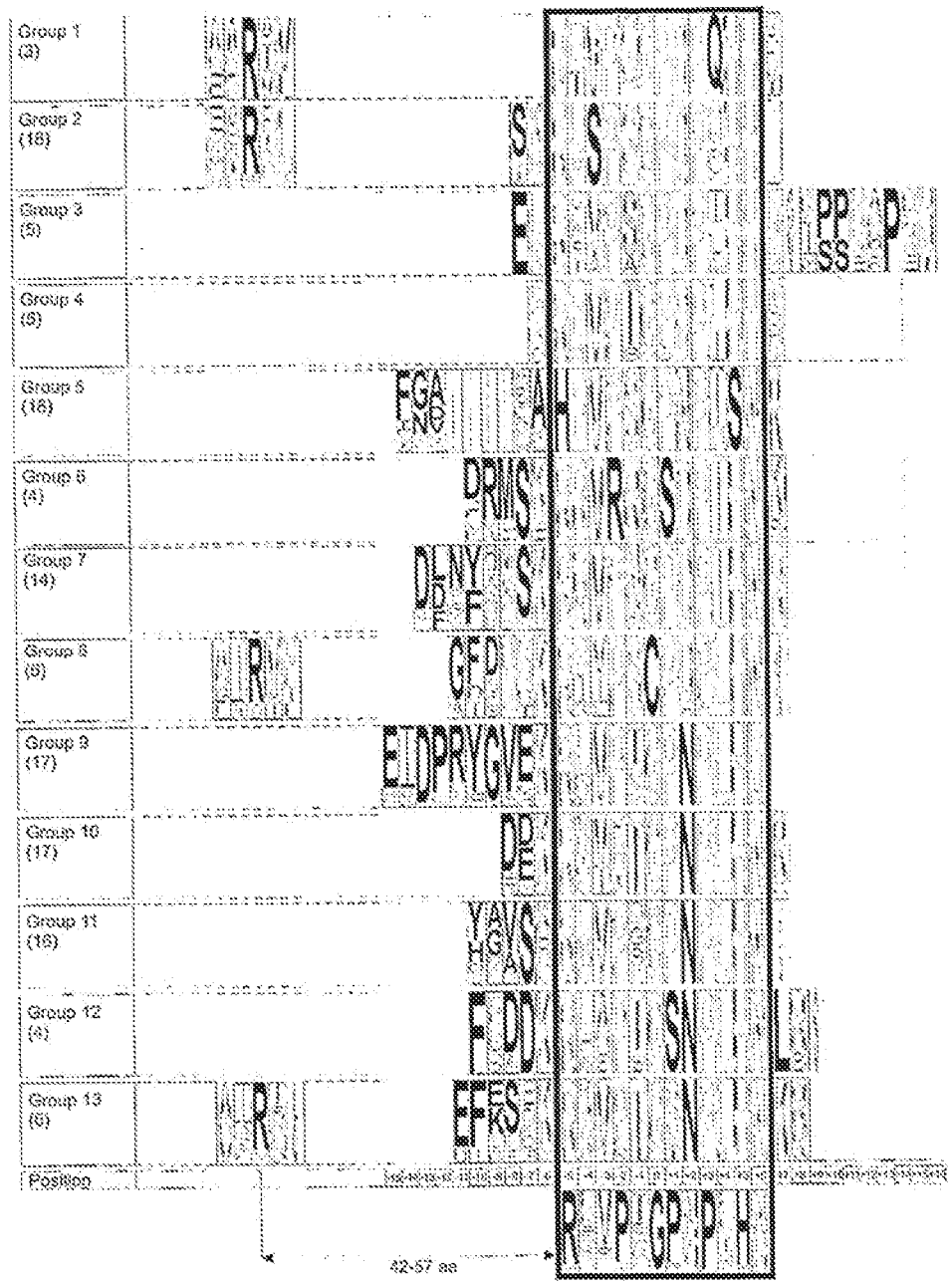
FIG. 11 shows the conservation of residues in the CLE signalling domain—the dashed line indicates the group 5 that contains all the putative PXY ligands.
Figure 17:
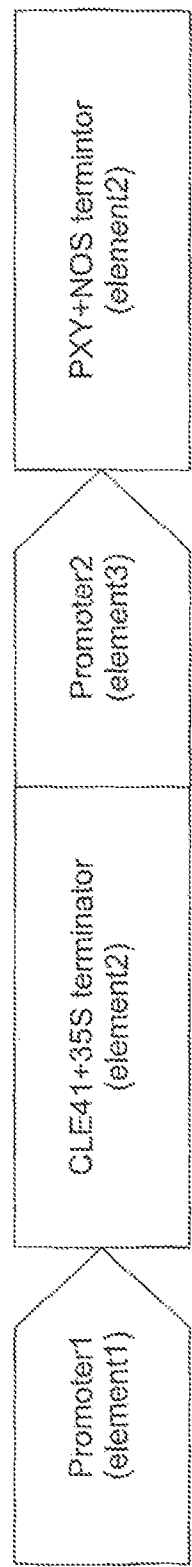
FIG. 17 shows the diagram of the multisite gateway kit for cloning.

Nucleic acid molecules encoding CLE41 and CLE42 are preferably those which encode an amino acid sequence as defined by the consensus sequence of FIG. 10 (SEQ ID NO. 12), and preferably having the sequences as shown in FIG. 13B (SEQ ID NO. 22) or 14B (SEQ ID NO. 24). References to nucleic acid molecules encoding CLE41 and CLE42 also include variants of the sequences of FIG. 13B (SEQ ID NO. 22) or 14B (SEQ ID NO. 24). A variant sequence is derived from the sequence of FIG. 13B (SEQ ID NO. 22) or 14B (SEQ ID NO. 24) by the addition, deletion or substitution of one or more nucleotide residues. The variant preferably encodes a polypeptide having CLE41 or CLE42 or a functional equivalent thereof, as defined herein. Preferably, a variant of a nucleotide sequence of FIG. 13B (SEQ ID NO. 22) or 14B (SEQ ID NO. 24) will have at least 50%, even more preferably at least 60%, and even more preferably at least 70%, 75%, 80%, 82%, 84%, 85%, 86%, 87%, 88%, 89%, 90%, 91%, 92%, 93%, 94%, 95%, 96%, 97%, 98%, 99%, or 100% sequence identity with a sequence of FIG. 13B (SEQ ID NO. 22) or 14B (SEQ ID NO. 24). Alternatively, a variant sequence which is substantially identical to a sequence of FIG. 13B (SEQ ID NO. 22) or 14B (SEQ ID NO. 24) may also be defined as one which hybridises under stringent conditions to the complement of a nucleotide sequence of FIG. 13B (SEQ ID NO. 22) or 14B (SEQ ID NO. 24).

Nucleic acid molecules encoding CLE41 and/or CLE42 may be derived from *Arabidopsis*, or may be derived from any other plant and will preferably share preferably at least 50%, even more preferably at least 60%, and even more preferably at least 70%, 75%, 80%, 82%, 84%, 85%, 86%, 87%, 88%, 89%, 90%, 91%, 92%, 93%, 94%, 95%, 96%, 97%, 98%, 99%, or 100% sequence identity with a CLE41 and/or CLE42 gene from *Arabidopsis thaliana*, as shown in FIG. 13B (SEQ ID NO. 22) or 14B (SEQ ID NO. 24).

Also encompassed by the present invention are fragments of the nucleic acid molecules encoding CLE41 and/or or CLE42. Preferably, such fragments encode a fragment of a CLE41 or CLE42 polypeptide as defined herein. A fragment of a nucleic acid molecules encoding CLE41 or CLE42 will preferably comprise at least 21 nucleotides in length, more preferably at least 24, 27, 30 or 33 nucleotides, up to the total number of nucleotide residues in a full length sequence of FIG. 13B (SEQ ID NO. 22) or 14B (SEQ ID NO. 24).

In the present invention, PXY is a polypeptide having the amino acid sequences shown in FIG. 15A (SEQ ID NO. 25). References to PXY include functional equivalents thereof. By a functional equivalent of PXY is meant a polypeptide which is derived from the native PXY polypeptide sequence of FIG. 15 by addition, deletion or substitution of one or more amino acids. A functional equivalent of PXY for use in the present invention will be biologically active, and preferably have some or all of the desired biological activity of the native polypeptide, preferably the ability to bind to CLE41 and/or CLE42 and regulate growth and/or differentiation of the vascular tissue. Functional equivalents may exhibit altered binding characteristics to CLE41 and/or CLE42 compared to a native PXY protein. Preferred functional equivalents may show reduced non-desirable biological activity compared to the native protein.

Figure 12:
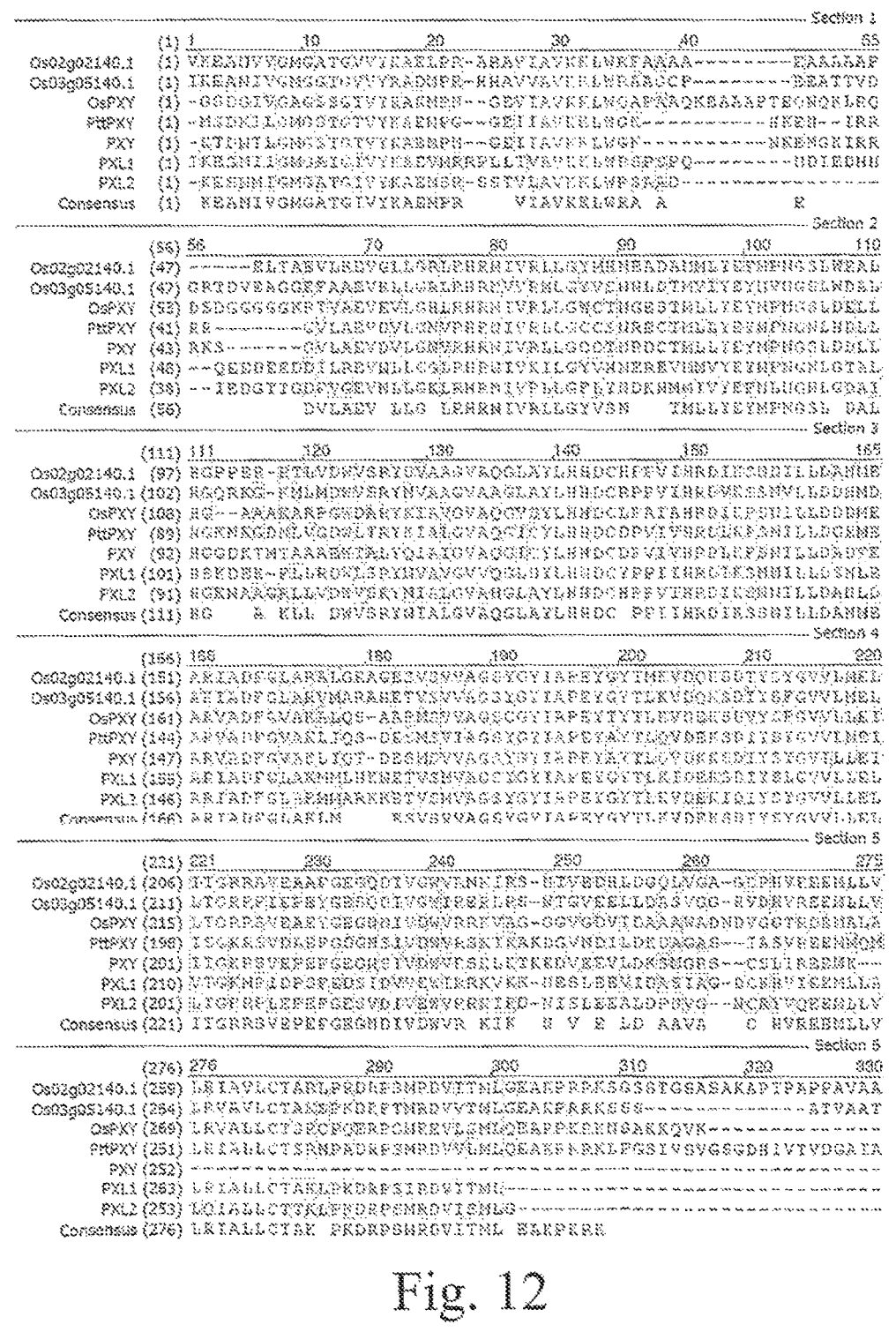

In the present invention, PXY and functional equivalents thereof are proteins found in undifferentiated procambial cells, which mediate activation of a signalling pathway when bound by CLE41 and/or CLE42, resulting in division of the cambial cells. Preferably, PXY or its functional equivalents is a protein kinase, preferably comprising a leucine rich domain. More preferably, it comprises a LLR-RLK (Leucine Rich Repeat-Receptor-Like-Kinase) protein. Preferably, PXY or its functional equivalents are members of the XI family of *Arabidopsis thaliana* RLK proteins, and preferably comprise a conserved region in the kinase domain having the sequence comprising the consensus sequence of FIG. 12 (SEQ ID NO. 20) or a biologically active portion thereof, or a sequence having at least 30%, 40%, 50%, 55%, 60, 65%, 70%, 75%, 80%, 85%, 90%, 95%, 96%, 97%, 98%, 99% or 100% sequence identity to the consensus sequence of FIG. 12 (SEQ ID NO. 20). Most preferably, a functional equivalent thereof will preferably comprise an amino acid having at least 70% sequence identity to the consensus sequence of FIG. 12 (SEQ ID NO. 20) and preferably will bind a CLE 41 and/or CLE 42 polypeptide or fragment thereof. A functional equivalent of PXY preferably also shares preferably at least 50%, even more preferably at least 60%, and even more preferably at least 70%, 75%, 80%, 82%, 84%, 85%, 86%, 87%, 88%, 89%, 90%, 91%, 92%, 93%, 94%, 95%, 96%, 97%, 98%, 99%, or 100% sequence homology with native PXY. Preferably, a functional equivalent may also share sequence identity with the PXY sequence of FIG. 15A (SEQ ID NO. 25), respectively References to PXY also include fragments of the PXY polypeptides or its functional equivalents. A fragment is a portion of a polypeptide sequence, preferably which retains some or all of the biological activity of the full length sequence. Preferably, fragments of PXY retain the ability to bind a ligand and regulate the growth and/or differentiation of the vascular tissue of a plant. Preferably, a fragment will comprise at least a portion of the kinase domain, preferably a biologically active portion thereof, up to the full length kinase domain. Most preferably, a fragment will further comprise at least a portion of the extracellular domain, and will preferably comprise at least a portion of the LLR region.

Nucleic acid molecules encoding PXY are preferably those which encode an amino acid sequence as defined in FIG. 15A (SEQ ID NO. 25), and preferably having the sequences as shown in FIG. 15B (SEQ ID NO. 26) or C (SEQ ID NO. 27). References to nucleic acid molecules encoding PXY also include variants of the sequences of FIG. 15B (SEQ ID NO. 26) or C (SEQ ID NO. 27). A variant sequence is a nucleic acid molecules which is derived from the sequence of FIG. 15B (SEQ ID NO. 26) or C (SEQ ID NO. 27) by the addition, deletion or substitution of one or more nucleotide residues. The variant preferably encodes a polypeptide having PXY activity, as defined herein. Preferably, a variant of a nucleotide sequence of FIG. 15B (SEQ ID NO. 26) or C (SEQ ID NO. 27) will have at least 50%, even more preferably at least 60%, and even more preferably at least 70%, 75%, 80%, 82%, 84%, 85%, 86%, 87%, 88%, 89%, 90%, 91%, 92%, 93%, 94%, 95%, 96%, 97%, 98%, 99%, or 100% sequence identity with a sequence of FIG. 15B (SEQ ID NO. 26) or C (SEQ ID NO. 27). Alternatively, a variant sequence which is substantially identical to a sequence of FIG. 15B (SEQ ID NO. 26) or C (SEQ ID NO. 27) may also be defined as one which hybridises under stringent conditions to the complement of a nucleotide sequence of FIG. 15B (SEQ ID NO. 26) or C (SEQ ID NO. 27).

Nucleotide sequences encoding PXY may be derived from *Arabidopsis*, or may be derived from any other plant and will preferably share preferably at least 50%, even more preferably at least 60%, and even more preferably at least 70%, 75%, 80%, 82%, 84%, 85%, 86%, 87%, 88%, 89%, 90%, 91%, 92%, 93%, 94%, 95%, 96%, 97%, 98%, 99%, or 100% % sequence identity with a PXY gene from *Arabidopsis thaliana*, as shown in FIG. 15B (SEQ ID NO. 26) or C (SEQ ID NO. 27). Genbank references are PXY=At5g61480 (TAIR), PXL1=At1g08590 (TAIR), PXL2=At4g28650 (TAIR).

Also encompassed by the present invention are fragments of the nucleic acid molecule encoding PXY. Preferably, such fragments encode a fragment of a PXY polypeptide as defined herein. A fragment of a nucleic acid molecule encoding PXY will preferably comprise at least 10, 20, 30, 40, 50, 60, 70, 80 or 90 or 100, 200 or 300 or more nucleotides in length, up to the total number of nucleotide residues in a full length sequence of FIG. 15A (SEQ ID NO. 25).

Also provided in the present invention are antisense sequences of the above mentioned nucleic acid molecules, which hybridise under stringent conditions to the nucleotide sequences encoding CLE41 and/or CLE42 or PXY, or a functional equivalents thereof, as defined above. Such sequences are useful in down regulating expression of the CLE41 and/or CLE42 and/or PXY or functional equivalents thereof. Whilst in a preferred embodiment, both receptor and ligand will be either up-regulated (over-expressed) or down-regulated in a cell of a plant, it is envisaged that it may in certain circumstances be desirable to up-regulate either the receptor whilst down-regulating the ligand, or vice versa.

As used herein, the term "hybridizes under stringent conditions" describes conditions for hybridization and washing. Stringent conditions are known to those skilled in the art and can be found in available references (e.g., Current Protocols in Molecular Biology, John Wiley & Sons, N.Y., 1989, 6.3.1-6.3.6). Aqueous and non-aqueous methods are described in that reference and either can be used. A preferred example of stringent hybridization conditions are hybridization in 6× sodium chloride/sodium citrate (SSC) at about 45° C., followed by one or more washes in 0.2×SSC, 0.1% (w/v) SDS at 50° C. Another example of stringent hybridization conditions are hybridization in 6×SSC at about 45° C., followed by one or more washes in 0.2×SSC, 0.1% (w/v) SDS at 55° C. A further example of stringent hybridization conditions are hybridization in 6×SSC at about 45° C., followed by one or more washes in 0.2×SSC, 0.1% (w/v) SDS at 60° C. Preferably, stringent hybridization conditions are hybridization in 6×SSC at about 45° C., followed by one or more washes in 0.2×SSC, 0.1% (w/v) SDS at 65° C. Particularly preferred stringency conditions (and the conditions that should be used if the practitioner is uncertain about what conditions should be applied to determine if a molecule is within a hybridization limitation of the invention) are 0.5 molar sodium phosphate, 7% (w/v) SDS at 65° C., followed by one or more washes at 0.2×SSC, 1% (w/v) SDS at 65° C. Preferably, an isolated nucleic acid molecule of the invention that hybridizes under stringent conditions to the sequence of FIG. 15 B (SEQ ID NO. 26) or C (SEQ ID NO. 27) corresponds to a naturally-occurring nucleic acid molecule.

Sequence identity is determined by comparing the two aligned sequences over a pre-determined comparison window, and determining the number of positions at which—identical residues occur. Typically, this is expressed as a percentage. The measurement of sequence identity of a nucleotide sequences is a method well known to those skilled in the art, using computer implemented mathematical algorithms such as ALIGN (Version 2.0), GAP, BESTFIT, BLAST® algorithm (Altschul et al J. Mol. Biol. 215: 403 (1990)), FASTA and TFASTA (Wisconsin Genetic Software Package Version 8, available from Genetics Computer Group, Accelrys Inc. San Diego, Calif.), and CLUSTAL (Higgins et al, Gene 73: 237-244 (1998)), using default parameters.

Calculations of sequence homology or identity between sequences are performed as follows:

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 75%, 80%, 82%, 84%, 85%, 86%, 87%, 88%, 89%, 90%, 91%, 92%, 93%, 94%, 95%, 96%, 97%, 98%, 99%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman et al. (1970) J. Mol. Biol. 48:444-453) algorithm which has been incorporated into the GAP program in the GCG software package, using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a BLOSUM 62 scoring matrix with a gap penalty of 12, a gap extend penalty of 4, and a frameshift gap penalty of 5.

The percent identity between two amino acid or nucleotide sequences can be determined using the algorithm of Meyers et al., (1989) CABIOS 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST® algorithm and XBLAST® algorithm programs (version 2.0) of Altschul, et al. (1990) J. Mol. Biol. 215:403-410). BLAST® algorithm nucleotide searches can be performed with the NBLAST® algorithm program, score=100, wordlength=12 to obtain nucleotide sequences homologous to nucleic acid molecules of the invention. BLAST® algorithm protein searches can be performed with the XBLAST® algorithm program, score=50, wordlength=3 to obtain amino acid sequences homologous to protein molecules of the invention. To obtain gapped alignments for comparison purposes, gapped BLAST® algorithm can be utilized as described in Altschul et al. (1997, Nucl. Acids Res. 25:3389-3402). When using BLAST® algorithm and gapped BLAST® algorithm programs, the default parameters of the respective programs (e.g., XBLAST® algorithm and NBLAST® algorithm) can be used.

Sequence comparisons are preferably made over the full-length of the relevant sequence described herein.

The polypeptide sequences and nucleic acid molecules used in the present invention may be isolated or purified. By "purified" is meant that they are substantially free from other cellular components or material, or culture medium. "Isolated" means that they may also be free of naturally occurring sequences which flank the native sequence, for example in the case of nucleic acid molecule, isolated may mean that it is free of 5' and 3' regulatory sequences.

The polypeptide and nucleic acid molecule used in the invention may be naturally occurring or may be synthetic. The nucleic acid molecule may be recombinant.

The present invention is based upon using either CLE41 and/or CLE42 and/or a PXY, or functional equivalents thereof, to manipulate the growth and/or structure of a plant. By "manipulate" is meant altering the native growth pattern of a plant, compared to that of a non-manipulated plant of the same species, grown under identical conditions. The manipulation is preferably effected by altering the levels of said receptor and ligand in a cell of the plant.

A plant having increased levels of said CLE41 and/or CLE42 and/or a PXY, or functional equivalents thereof in a particular tissue and at a pre-selected developmental stage, compared to the native levels in the same tissue of a native plant of the same species, at the same developmental stage and grown in identical conditions.

Herein, the growth of a plant refers to the size of a plant, preferably the secondary growth, and preferably the amount of vascular and/or interfasicular tissue, more preferably the amount of xylem cells, also referred to as the woody tissue or biomass of a plant.

By identical conditions is meant conditions which are the substantially the same in terms of temperature, light, and availability of nutrients and water. By substantially is meant that the conditions may vary slightly, but not to an extent to which is known to affect the growth of a plant.

The structure of a plant refers to the organisation of tissue in a plant, preferably the vascular tissue, most preferably the polarity of the phloem and xylem cells.

The use of said CLE41 and/or CLE42 and/or a PXY, or functional equivalents thereof as defined herein to manipulate the growth and/or structure of a plant may be achieved in any manner which alters the regulation of the signalling pathway mediated by CLE41 and/or CLE42 binding to PXY. Preferably, the invention may be achieved in any manner which up-regulates the signalling pathway. Preferably, the manipulation is mediated via a PXY ligand as defined herein, preferably CLE41 and/or CLE42, or via a CLE41 and/or CLE42 receptor, preferably PXY. For example, manipulation may comprise altering their expression pattern within the plant, altering the amount of said receptor and/or ligand within the plant, or altering the binding pattern thereof.

By modulation of the levels of the CLE41 and/or CLE42 and/or a PXY, or functional equivalents thereof, is meant an increase or decrease in the levels of in the plant, preferably the levels localised in the vascular tissue, and preferably in the cambium or procambium of a plant, as compared to the levels in the same tissue in a native plant of the same species at the same stage if developed and grown under identical conditions, and in which no modulation has been made. Preferably, the levels of CLE41 and/or CLE42 and/or a PXY, or functional equivalents thereof, are increased. Preferred levels of PXY ligand are at least 5, 10, 20, 30, 40, 50, 60, 70, 80, 90% more or less relative to said native plant. Preferred levels of CLE41 and/or CLE42 receptor are 5, 10, 20, 30, 40, 50, 60, 70, 80, 90% more or less relative to said native plant.

The alteration in levels of CLE41 and/or CLE42 and/or a PXY, or functional equivalents thereof, as defined above preferably increases or decreases the activity by at least about 2-fold compared to a basal level of activity. More preferably said activity is increased or decreased by at least about 5 fold; 10 fold; 20 fold, 30 fold, 40 fold, 50 fold. Preferably said activity is increased or decreased by between at least 50 fold and 100 fold. Preferably said increase or decrease is greater than 100-fold.

It will be apparent that means to modulate the activity of a polypeptide encoded by a nucleic acid molecule are known to the skilled artisan. For example, and not by limitation, altering the gene dosage by providing a cell with multiple copies of said gene or its complement. Alternatively, or in addition, a gene(s) may be placed under the control of a powerful promoter sequence or an inducible promoter sequence to elevate expression of mRNA encoded by said gene. The modulation of mRNA stability is also a mechanism used to alter the steady state levels of an mRNA molecule, typically via alteration to the 5' or 3' untranslated regions of the mRNA.

It is envisaged that where a plant naturally expresses said CLE41 and/or CLE42 receptor and/or PXY ligand, their modulation may be achieved by altering the expression pattern of the native gene(s) and/or production of the polypeptide. This may be achieved by any suitable method, including altering transcription of the gene, and/or translation of the mRNA into polypeptide, and post-translational modification of the polypeptide.

Altering the expression pattern of a native gene may be achieved by placing it under control of a heterologous regulatory sequence, which is capable of directing the desired expression pattern of the gene. Suitable regulatory sequences are described herein. Alternatively, regulation of expression of the native gene may be altered through changing the pattern of transcription factors which mediate expression of the gene. This may require the use of modified transcription factors, whose binding pattern is altered to obtain a desired expression pattern of the gene. Alternatively, the copy number of the native gene may be increased or decreased, in order to change the amount of expression of the gene. Suitable methods for carrying out these embodiments of the invention are known to persons skilled in the art, and may employ the use of an expression construct according to the invention.

Plants transformed with a nucleic acid molecule or expression construct of the invention may be produced by standard techniques known in the art for the genetic manipulation of plants. DNA can be introduced into plant cells using any suitable technology, such as a disarmed Ti-plasmid vector carried by *Agrobacterium* exploiting its natural gene transferability (EP-A-270355, EP-A-0116718, NAR 12(22):8711-87215 (1984), Townsend et al., U.S. Pat. No. 5,563,055); particle or microprojectile bombardment (U.S. Pat. No. 5,100,792, EP-A-444882, EP-A-434616; Sanford et al, U.S. Pat. No. 4,945,050; Tomes et al. (1995) "Direct DNA Transfer into Intact Plant Cells via Microprojectile Bombardment", in Plant Cell, Tissue and Organ Culture: Fundamental Methods, ed. Gamborg and Phillips (Springer-Verlag, Berlin); and McCabe et al. (1988) Biotechnology 6: 923-926); microinjection (WO 92/09696, WO 94/00583, EP 331083, EP 175966, Green et al. 91987) Plant Tissue and Cell Culture, Academic Press, Crossway et al. (1986) Biotechniques 4:320-334); electroporation (EP 290395, WO 8706614, Riggs et al. (1986) Proc. Natl. Acad. Sci. USA 83:5602-5606; D'Halluin et al. 91992). Plant Cell 4:1495-1505) other forms of direct DNA uptake (DE 4005152, WO 9012096, U.S. Pat. No. 4,684,611, Paszkowski et al. (1984) EMBO J. 3:2717-2722); liposome-mediated DNA uptake (e.g. Freeman et al (1984) Plant Cell Physiol, 29:1353); or the vortexing method (e.g. Kindle (1990) Proc. Nat. Acad. Sci. USA 87:1228). Physical methods for the transformation of plant cells are reviewed in Oard (1991) Biotech. Adv. 9:1-11. See generally, Weissinger et al. (1988) Ann. Rev. Genet. 22:421-477; Sanford et al. (1987) Particulate Sciences and Technology 5:27-37; Christou et al. (1988) Plant Physiol. 87:671-674; McCabe et al. (1988) Bio/Technology 6:923-926; Finer and McMullen (1991) In Vitro Cell Dev. Biol. 27P:175-182; Singh et al. (1988) Theor. Appl. Genet. 96:319-324; Datta et al. (1990) Biotechnology 8:736-740; Klein et al. (1988) Proc. Natl. Acad. Sci. USA 85: 4305-4309; Klein et al. (1988) Biotechnology 6:559-563; Tomes, U.S. Pat. No. 5,240,855; Buising et al. U.S. Pat. No. 5,322,783 and U.S. Pat. No. 5,324,646; Klein et al. (1988) Plant Physiol 91: 440-444; Fromm et al (1990) Biotechnology 8:833-839; Hooykaas-Von Slogteren et al. 91984). Nature (London) 311:763-764; Bytebier et al. (1987) Proc. Natl. Acad. Sci. USA 84:5345-5349; De Wet et al. (1985) in The Experimental Manipulation of Ovule Tissues ed. Chapman et al. (Longman, N.Y.), pp. 197-209; Kaeppler et al. (1990) Plant Cell Reports 9:415-418 and Kaeppler et al. (1992) Theor. Appl. Genet. 84:560-566; Li et al. (1993) Plant Cell Reports 12: 250-255 and Christou and Ford (1995) Annals of Botany 75: 407-413; Osjoda et al. (1996) Nature Biotechnology 14:745-750, all of which are herein incorporated by reference.

*Agrobacterium* transformation is widely used by those skilled in the art to transform dicotyledonous species. Recently, there has been substantial progress towards the routine production of stable, fertile transgenic plants in almost all economically relevant monocot plants (Toriyama et al. (1988) Bio/Technology 6: 1072-1074; Zhang et al. (1988) Plant Cell rep. 7379-384; Zhang et al. (1988) Theor. Appl. Genet. 76:835-840; Shimamoto et al. (1989) Nature 338:274-276; Datta et al. (1990) Bio/Technology 8: 736-740; Christou et al. (1991) Bio/Technology 9:957-962; Peng et al (1991) International Rice Research Institute, Manila, Philippines, pp. 563-574; Cao et al. (1992) Plant Cell Rep. 11: 585-591; Li et al. (1993) Plant Cell Rep. 12: 250-255; Rathore et al. (1993) Plant Mol. Biol. 21:871-884; Fromm et al (1990) Bio/Technology 8:833-839; Gordon Kamm et al. (1990) Plant Cell 2:603-618; D'Halluin et al. (1992) Plant Cell 4:1495-1505; Walters et al. (1992) Plant Mol. Biol. 18:189-200; Koziel et al. (1993). Biotechnology 11194-200; Vasil, I. K. (1994) Plant Mol. Biol. 25:925-937; Weeks et al (1993) Plant Physiol. 102:1077-1084; Somers et al. (1992) Bio/Technology 10:1589-1594; WO 92/14828. In particular, *Agrobacterium* mediated transformation is now emerging also as an highly efficient transformation method in monocots. (Hiei, et al. (1994) The Plant Journal 6:271-282). See also, Shimamoto, K. (1994) Current Opinion in Biotechnology 5:158-162; Vasil, et al. (1992) Bio/Technology 10:667-674; Vain, et al. (1995) Biotechnology Advances 13(4):653-671; Vasil, et al. (1996) Nature Biotechnology 14: 702).

Microprojectile bombardment, electroporation and direct DNA uptake are preferred where *Agrobacterium* is inefficient or ineffective. Alternatively, a combination of different techniques may be employed to enhance the efficiency of the transformation process, e.g. bombardment with *Agrobacterium*-coated microparticles (EP-A-486234) or microprojectile bombardment to induce wounding followed by co-cultivation with *Agrobacterium* (EP-A-486233).

Altering the production of a polypeptide may be achieved by increasing the amount of mRNA produced, increasing the stability of protein, altering the rate of post translational modification for example altering rates of proteolytic cleavage.

Altering the post-translational modification of a polypeptide may also affect its structure and function, and may be used to alter the expression of the native polypeptide. For example, the ligand is likely to be only a portion of the full length proteins and the active ligand is probably released by proteolysis.

Alternatively, a polypeptide or nucleic acid molecule as defined herein may be introduced into the plant, by any suitable means such as spraying, uptake by the roots, or injection into phloem. To down-regulate said receptor or ligand in a plant, an enzyme may be introduced which inhibits or digests one or both of the receptor or ligand.

In addition, modulating the activity mediated by CLE41 and/or CLE42 and/or a PXY, or functional equivalents thereof, by altering their binding pattern, in order to up-or-down-regulate the downstream signalling pathway. The binding pattern may be altered in any suitable way, for example by altering the structure, binding affinity, temporal binding pattern, selectivity and amount available for binding on the cell surface of CLE41 and/or CLE42 and/or a PXY, or functional equivalents thereof.

The binding pattern may be altered by making appropriate variations to the ligand polypeptide, for example to change its binding site to the receptor, using known methods for mutagenesis.

Alternatively, non-protein analogues may be used. Methods for manipulating a polypeptide used in the present invention are known in the art, and include for example altering the nucleic acid sequence encoding the polypeptide. Methods for mutagenesis are well known. Preferably, where variants are produced using mutagenesis of the nucleic acid coding sequence, this is done in a manner which does not affect the reading frame of the sequence and which does not affect the polypeptide in a manner which affects the desired biological activity.

In selecting suitable variants for use in the present invention, routine assays may be used to screen for those which have the desired properties. This may be done by visual observation of plants and plant material, or measuring the biomass of the plant or plant material.

Thus, for use in altering the expression of the CLE41 and/or CLE42 and/or a PXY, or functional equivalents thereof, in a cell of a plant, there is provided an expression cassette comprising a regulatory sequence to modulate the expression of the native CLE41 and/or CLE42 or PXY genes in a plant. Preferably, the regulatory sequences are designed to be operably linked to the native gene, in order to direct expression in a manner according to the present invention.

The nucleic acid molecules as described herein, and/or a regulatory sequence are preferably provided as part of an expression cassette, for expression of the sequence in a cell of interest. Suitable expression cassettes may also comprise 5' and 3' regulatory sequences operably linked to the sequences of interest. In addition, genes encoding, for example, selectable markers and reporter genes may be included. The expression cassette will preferably also contain one or more restriction sites, to enable insertion of the nucleotide sequence and/or a regulatory sequence into the plant genome, at a pre-selected position. Also provided on the expression cassette may be transcription and translation initiation regions, to enable expression of the incoming genes, transcription and translational termination regions, and regulatory sequences. These sequences may be native to the plant being transformed, or may be heterologous and/or foreign.

Heterologous sequences are sequences which in nature are not operably linked to each other and/or are not found next to each other in a native sequence. In contrast, homologous sequences refer to sequences which share sequence similarity, which may be described as sequence homology. Homology is usually in a fragment of the sequence, typically in a functional domain of the sequence.

A foreign sequence is one which is not found in the native genome of the plant being transformed.

A regulatory sequence is a nucleotide sequence which is capable of influencing transcription or translation of a gene or gene product, for example in terms of initiation, rate, stability, downstream processing, and mobility. Examples of regulatory sequences include promoters, 5' and 3' UTR's, enhancers, transcription factor or protein binding sequences, start sites and termination sequences, ribozyme binding sites, recombination sites, polyadenylation sequences, sense or antisense sequences. They may be DNA, RNA or protein. The regulatory sequences may be plant- or virus derived, and preferably may be derived from the same species of plant as the plant being modulated.

By "promoter" is meant a nucleotide sequence upstream from the transcriptional initiation site and which contains all the regulatory regions required for transcription. Suitable promoters include constitutive, tissue-specific, inducible, developmental or other promoters for expression in plant cells comprised in plants depending on design. Such promoters include viral, fungal, bacterial, animal and plant-derived promoters capable of functioning in plant cells.

Constitutive promoters include, for example CaMV 35S promoter (Odell et al. (1985) Nature 313, 9810-812); rice actin (McElroy et al. (1990) Plant Cell 2: 163-171); ubiquitin (Christian et al. (1989) Plant Mol. Biol. 18 (675-689); pEMU (Last et al. (1991) Theor Appl. Genet. 81: 581-588); MAS (Velten et al. (1984) EMBO J. 3. 2723-2730); ALS promoter (U.S. application Ser. No. 08/409,297), and the like. Other constitutive promoters include those in U.S. Pat. Nos. 5,608,149; 5,608,144; 5,604,121; 5,569,597; 5,466,785; 5,399,680, 5,268,463; and U.S. Pat. No. 5,608,142.

Chemical-regulated promoters can be used to modulate the expression of a gene in a plant through the application of an exogenous chemical regulator. Depending upon the objective, the promoter may be a chemical-inducible promoter, where application of the chemical induced gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) Proc. Natl. Acad. Sci. USA 88: 10421-10425 and McNellis et al. (1998) Plant J. 14(2): 247-257) and tetracycline-inducible and tetracycline-repressible promoters (see, for example, Gatz et al. (1991) Mol. Gen. Genet. 227: 229-237, and U.S. Pat. Nos. 5,814,618 and 5,789,156, herein incorporated by reference.

Where enhanced expression in particular tissues is desired, tissue-specific promoters can be utilised. Tissue-specific promoters include those described by Yamamoto et al. (1997) Plant J. 12(2): 255-265; Kawamata et al. (1997) Plant Cell Physiol. 38(7): 792-803; Hansen et al. (1997) Mol. Gen. Genet. 254(3): 337-343; Russell et al. (1997) Transgenic Res. 6(2): 157-168; Rinehart et al. (1996) Plant Physiol. 112(3): 1331-1341; Van Camp et al. (1996) Plant Physiol. 112(2): 525-535; Canevascni et al. (1996) Plant Physiol. 112(2): 513-524; Yamamoto et al. (1994) Plant Cell Physiol. 35(5): 773-778; Lam (1994) Results Probl. Cell Differ. 20: 181-196; Orozco et al. (1993) Plant Mol. Biol. 23(6): 1129-1138; Mutsuoka et al. (1993) Proc. Natl. Acad. Sci. USA 90 (20): 9586-9590; and Guevara-Garcia et al (1993) Plant J. 4(3): 495-50.

"Operably linked" means joined as part of the same nucleic acid molecule, suitably positioned and oriented for transcription to be initiated from the promoter. DNA operably linked to a promoter is "under transcriptional initiation regulation" of the promoter. In a preferred aspect, the promoter is an inducible promoter or a developmentally regulated promoter.

The promoters which control the expression of CLE41 and/or CLE42 are preferably tissue or organ specific, such that expression of CLE41 and/or CLE42 can be directed to a particular organ or tissue, such as the vascular tissue, preferably the cambium or procambium, and most preferably phloem or xylem tissue. The promoters may be constitutive, whereby they direct expression under most environmental or developmental conditions. More preferably, the promoter is inducible, and will direct expression in response to environmental or developmental cues, such as temperature, chemicals, drought, and others. The promoter may also be developmental stage specific.

Examples of suitable promoter sequences include those of the T-DNA of *A. tumefaciens*, including mannopine synthase, nopaline synthase, and octopine synthase; alcohol dehydrogenase promoter from corn; light inducible promoters such as ribulose-biphosphate-carboxylase small subunit gene from various species and the major chlorophyll a/b binding protein gene promoter; histone promoters (EP 507 698), actin promoters; maize ubiquitin 1 promoter (Christensen et al. (1996) Transgenic Res. 5:213); 35S and 19S promoters of cauliflower mosaic virus; developmentally regulated promoters such as the waxy, zein, or bronze promoters from maize; as well as synthetic or other natural promoters including those promoters exhibiting organ specific expression or expression at specific development stage(s) of the plant, like the alpha-tubulin promoter disclosed in U.S. Pat. No. 5,635,618. Preferred phloem specific promoters include SUC2, APL, KAN1, KAN2, At4g33660, At3g61380, and At1g79380. Preferred xylem specific promoters include REV, IRX1 COBL4, KOR, At2g38080, and At1g2744.

Suitable expression cassettes for use in the present invention can be constructed, containing appropriate regulatory sequences, including promoter sequences, terminator fragments, polyadenylation sequences, enhancer sequences, marker genes and other sequences as appropriate. For further details see, for example, Molecular Cloning: Laboratory Manual: $2^{nd}$ edition, Sambrook et al. 1989, Cold Spring Harbor Laboratory Press or Current Protocols in Molecular Biology, Second Edition, Ausubel et al. Eds., John Wiley & Sons, 1992. The expression cassettes may be a bi-functional expression cassette which functions in multiple hosts. In the case of GTase genomic DNA this may contain its own promoter or other regulatory elements and in the case of cDNA this may be under the control of an appropriate promoter or other regulatory elements for expression in the host cell.

An expression cassette including a nucleic acid molecule according to the invention need not include a promoter or other regulatory sequence, particularly if the vector is to be used to introduce the nucleic acid into cells for recombination into the gene.

Suitable selectable marker or reporter genes may be used to facilitate identification and selection of transformed cells. These will confer a selective phenotype on the plant or plant cell to enable selection of those cells which comprise the expression cassette. Preferred genes include the chloramphenicol acetyl transferase (cat) gene from Tn9 of *E. coli*, the beta-gluronidase (gus) gene of the uidA locus of *E. coli*, the green fluorescence protein (GFP) gene from *Aequoria victoria*, and the luciferase (luc) gene from the firefly *Photinus pyralis*. If desired, selectable genetic markers may be included in the construct, such as those that confer selectable phenotypes such as resistance to antibodies or herbicides (e.g. kanamycin, hygromycin, phosphinotricin, chlorsulfuron, methotrexate, gentamycin, spectinomycin, imidazolinones and glyphosate).

Reporter genes which encode easily assayable marker proteins are well known in the art. In general, a reporter gene is a gene which is not present or expressed by the recipient organism or tissue and which encodes a protein whose expression is manifested by some easily detectable property, e.g. phenotypic change or enzymatic activity.

The selectable marker or reporter gene may be carried on a separate expression cassette and co-transformed with the expression cassette of the invention. The selectable markers and/or reporter genes may be flanked with appropriate regulatory sequences to enable their expression in plants.

The expression cassette may also comprise elements such as introns, enhancers, and polyadenylation sequences. These elements must be compatible with the remainder of the expression cassette. These elements may not be necessary for the expression or function of the gene but may serve to improve expression or functioning of the gene by affecting transcription, stability of the mRNA, or the like. Therefore, such elements may be included in the expression construct to obtain the optimal expression and function of CLE41 and/or CLE42 and/or PXY in the plant.

The expression cassette comprising the heterologous nucleic acid may also comprise sequences coding for a transit peptide, to drive the protein coded by the heterologous gene into a desired part of the cell, for example the chloroplasts. Such transit peptides are well known to those of ordinary skill in the art, and may include single transit peptides, as well as multiple transit peptides obtained by the combination of sequences coding for at least two transit peptides. One preferred transit peptide is the Optimized Transit Peptide disclosed in U.S. Pat. No. 5,635,618, comprising in the direction of transcription a first DNA sequence encoding a first chloroplast transit peptide, a second DNA sequence encoding an N-terminal domain of a mature protein naturally driven into the chloroplasts, and a third DNA sequence encoding a second chloroplast transit peptide.

In the present invention, any plant species may be used, including both monocots and dicots. Preferred plants for use in the present invention are those which are targets for biomass, and/or are readily grown, exhibit high growth rates, are easily harvested, and can be readily converted to a biofuel. Preferred plants include grasses, trees, crops, and shrubs.

Suitable plants for use in the present invention are those which in their native form produce a high yield of feedstock, for paper or fuel production. Examples of suitable plant types include perennial fast growing herbaceous and woody plants, for example trees, shrubs and grasses. Preferred trees for use in the invention include poplar, hybrid poplar, willow, silver maple, black locust, sycamore, sweetgum and eucalyptus. Preferred shrubs include tobacco. Perennial grasses include switchgrass, reed canary grass, prairie cordgrass, tropical grasses, Brachypodiumdistachyon, and Miscanthes. Crops include wheat, soybean, alphalpha, corn, rice, maize, and sugar beet.

In yet still a further preferred embodiment of the invention said plant is a woody plant selected from: poplar; eucalyptus; Douglas fir; pine; walnut; ash; birch; oak; teak; spruce. Preferably said woody plant is a plant used typically in the paper industry, for example poplar.

Methods to transform woody species of plant are well known in the art. For example the transformation of poplar is disclosed in U.S. Pat. No. 4,795,855 and WO9118094. The transformation of eucalyptus is disclosed in EP1050209 and WO9725434. Each of these patents is incorporated in their entirety by reference.

In a still further preferred embodiment of the invention said plant is selected from: corn (*Zea mays*), canola (*Brassica napus, Brassica rapa* ssp.), alfalfa (*Medicago sativa*), rice (*Oryza sativa*), rye (*Secale cerale*), sorghum (*Sorghum bicolor, Sorghum vulgare*), sunflower (*helianthus annuas*), wheat (*Tritium aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*lopmoea batatus*), cassava (*Manihot esculenta*), coffee (*Cofea* spp.), coconut (*Cocos nucifera*), pineapple (*Anana comosus*), citrus tree (*Citrus* spp.) cocoa (*Theobroma cacao*), tea (*Camellia senensis*), banana (*Musa* spp.), avocado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Prunus amygdalus*), sugar beets (*Beta vulgaris*), oats, barley, vegetables and ornamentals.

Preferably, plants of the present invention are crop plants (for example, cereals and pulses, maize, wheat, potatoes, tapioca, rice, *sorghum*, millet, cassava, barley, pea, and other root, tuber or seed crops. Important seed crops are oil-seed rape, sugar beet, maize, sunflower, soybean, and *sorghum*. Horticultural plants to which the present invention may be applied may include lettuce, endive, and vegetable brassicas including cabbage, broccoli, and cauliflower, and carnations and geraniums. The present invention may be applied in tobacco, cucurbits, carrot, strawberry, sunflower, tomato, pepper, chrysanthemum.

Grain plants that provide seeds of interest include oil-seed plants and leguminous plants. Seeds of interest include grain seeds, such as corn, wheat, barley, rice, *sorghum*, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava been, lentils, chickpea, etc.

In a preferred embodiment of the invention said seed is produced from a plant selected from the group consisting of: corn (*Zea mays*), canola (*Brassica napus, Brassica rapa* ssp.), flax (*Linum usitatissimum*), alfalfa (*Medicago sativa*), rice (*Oryza sativa*), rye (*Secale cerale*), sorghum (*Sorghum bicolor, Sorghum vulgare*), sunflower (*Helianthus annus*), wheat (*Tritium aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*lopmoea batatus*), cassava (*Manihot esculenta*), coffee (*Cofea* spp.), coconut (*Cocos nucifera*), pineapple (*Anana comosus*), citris tree (*Citrus* spp.) cocoa (*Theobroma cacao*), tea (*Camellia senensis*), banana (*Musa* spp.), avacado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Prunus amygdalus*), sugar beets (*Beta vulgaris*), oats, barley, vegetables.

The present invention has uses in methods which require increased biomass in plants, for example where plant biomass is used in the manufacture of products such as biofuels and paper. The invention is not limited to methods of making these particular products, and it is envisaged that the invention will be applicable to the manufacture of a variety of plant based products. In addition, the invention is also useful in altering the characteristics of plant material, such that the plant material can be adapted for particular purposes. In one such embodiment, over expression of the ligand and/or receptor as defined herein may be used to increase the number of cells in the vascular tissue of a plant, but without increasing the actual biomass of the plant (i.e. the number of cells may be increased, but the size of these cells is smaller). This has the effect of increasing the density of the vascular tissue, and therefore producing a harder wood. Thus, the invention includes methods for the production of a wood product having a particular density. In addition, it is envisaged that by manipulating plant cells to differentiate their vascular tissue, and therefore grow, environmental growth signals may be bypassed and the present invention may be used to extend the growth season of plants, beyond that which would be possible in a native plant.

The embodiments described in relation to the each aspect apply to the other aspects of the invention, mutatis mutandis.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The present invention will now be described with reference to the following non-limiting examples:

EXAMPLES

DNA manipulation was carried out using standard methods. Over expression (35S) constructs for plant transformation were generated by cloning CLE41, CLE42, and PXY genomic DNA sequences into pK2GW7,0 (M. Karimi, D. Inze, A. Depicker, *Trends in Plant Science* 7, 193 (2002)) using gateway technology (invitrogen) with primers listed in the table. Sequences were amplified by PCR and cloned into pENTR-D-TOPO. Subsequently, reactions containing LR clonase II and pK2GW7,0 and the relevant TOPO vector, sequences were used to transfer sequences in pENTR-D-TOPO to the binary plasmid. pIRX3::CLE41/42 were constructed using the p3HSC Gateway destination vector (Atanassov et al. 2008) derived from pCB1300 by insertion of the 1.7 kb promoter sequences of irx3, the frame A (attR1/cmR/ccdB/attR2) cassette (Invitrogen) and the NOS terminator region from pGPTV-BAR. For SUC2::CLE41 we used overlapping PCR. The SUC2 promoter and CLE41 coding sequence were amplified separately with overlapping ends. These products were mixed, annealed and elongated prior to amplification with SUC2 and CLE41 forward and reverse oligos respectively. The resulting PCR product was cloned into pTF101.gw1 (Paz et al. 2004) via pENTR-D-TOPO. For tissue specific expression, promoters known to give xylem (IRX3; (Gardiner et al. 2003) or phloem (SUC2; (Truernit and Sauer 1995) specific expression were used.

Plasmids were sequenced and transformed into *Arabidopsis* using the method of Clough and Bent (S. J. Clough, A. F. Bent, *Plant Journal* 16, 735 (December, 1998)), In order to understand if over expression of PXY and CLE41 had the same effect in poplar, plants were transformed in tissue culture using *Agrobacterium* to transfer the constructs into poplar tissue using the method of Meilan and Ma (R. Meilan, C. Ma, *Methods in Molecular Biology* 344, 143 (2006). 35S::CLE41, SUC::CLE41 and wild type were grown in magenta boxes in the growth cabinet under the same conditions. Similarly, plasmids were transformed into *Nicotiana* using the method of Horsch et al (R. B. Horsch et al., *Science* 227, 1229 (Mar. 8, 1985, 1985). Maize was transformed with the plasmids by contracting out transformation services. Similar phenotypes were confirmed in 10 independent transgenic lines for 35S::CLE constructs in *Arabidopsis*. Increases in expression were confirmed in 5 lines per construct by RT-PCR. RT-PCR analysis was carried out using the gene-specific primers listed in the table. RNA was isolated using Trizol reagent (Invitrogen). cDNA synthesis, following DNase treatment, was performed using Superscript III reverse transcriptase (Invitrogen). Expression levels of CLE41 in wild type were compared to that of 35S::CLE41 by qRT-PCR. All samples were measured in technical triplicates on biological triplicates. The qRT-PCR reaction was performed using SYBR Green JumpStart Taq ReadyMix (Sigma) using an ABI Prism 7000 machine (Applied Biosystems). PCR conditions were as follows: 50° C. for 2 min, 95° C. for 10 min, and 40 cycles of 95° C. for 15 s and 60° C. for 60 s. A melting curve was produced at the end of every experiment to ensure that only single products were formed. Gene expression was determined using a version of the comparative threshold cycle (Ct) method. The average amplification efficiency of each target was determined using LinReg (M. Hardstedt et al., *Xenotransplantation* 12, 293 (2005)).

*Arabidopsis* lines which carried 35S::CLE41 35S::PXY and 35S::CLE42 35S::PXY were generated by crossing and identified in the F2 population. IRX3::CLE41 35S::PXY and SUC2::CLE41 35S::PXY lines were generated by directly transforming plants carrying the 35S::PXY construct with pIRX3::CLE41 or pSUC2::CLE41. SUC2::CLE41 and 35S::CLE41 cell counts were carried out on 10 independent T2's (2 bundles/plant) and 6 independent T1's (3 bundles/plant) respectively. 5 week plants were used. *Nicotiana* lines carrying 35S::CLE41 35S::PXY were also generated by crossing.

TABLE 1

Oligonucleotides used in Invention.

| Seq Id No. | Oligo Name | Sequence (5'-3') | Used for |
|---|---|---|---|
| 41 | CLE41F | CACCATGGCAACATCAAATGAC | 35S::CLE41 construct |
| 42 | CLE41R | AAACCAGATGTGCCAACTCA | 35S::CLE41 construct and genotyping |
| 43 | CLE42F | CACCATGAGATCTCCTCACATC | 35S::CLE42 construct |
| 44 | CLE42R | TGAATCAAACAAGCAACATAACAA | 35S::CLE42 construct and genotyping |
| 45 | PXY_ORF_f | CACCTTAAATCCACCATTGTCA | 35S::PXY construct |
| 46 | PXY_ORF_r | CCAAGATAATGGACGCCAAC | 35S::PXY construct |
| 47 | SUC2promFtopo | caccaacacatgttgccgagtca | SUC2::CLE41 overlap PCR entry clone |
| 48 | SUC2pro/CLE41(1) | GTCATTTGATGTTGCCATgaa atttctttgagagggtttttg | SUC2::CLE41 overlap PCR entry clone |
| 49 | SUC2pro/CLE41(2) | caaaaaccctctcaaagaaat ttcATGGCAACATCAAATGAC | SUC2::CLE41 overlap PCR entry clone |
| 50 | CLE41_RTF | CCATGACTCGTCATCAGTCC | RT-PCR |
| 51 | CLE41_RTR | TTTGGACCACTAGGAACCTCA | RT-PCR |
| 52 | CLE42_RTF | TCCAAACCCATCAAAGAACC | RT-PCR |
| 53 | CLE42_RTR | ATTGGCACCGATCATCTTTC | RT-PCR |
| 54 | PXY1_RTF | AACCTAGCAATATCCTCCTCGAC | RT-PCR |
| 55 | PXY1_RTR | GGTTCCACCGATCTTTTTCC | RT-PCR |
| 56 | ACT8-1 | ATGAAGATTAAGGTCGTGGCA | RT-PCR control |
| 57 | ACT8-2 | CCGAGTTTGAAGAGGCTAC | RT-PCR control |
| 58 | qCLE41f | TCAAGAGGGTTCTCCTCGAA | qRT-PCR |
| 59 | qCLE41r | TGTGCTAGCCTTTGGACGTA | qRT-PCR |
| 60 | 18s rRNA F | CATCAGCTCGCGTTGACTAC | qRT-PCR control |

TABLE 1-continued

Oligonucleotides used in Invention.

| Seq Id No. | Oligo Name | Sequence (5'-3') | Used for |
|---|---|---|---|
| 61 | 18s rRNA R | GATCCTTCCGCAGGTTCAC | qRT-PCR control |
| 62 | 35S promoter F | CGCACAATCCCACTATCCTT | Genotyping |
| 63 | pxy-3-r | TTACCGTTTGATCCAAGCTTG | Genotyping |

Histology

Analysis of tobacco, poplar and *Arabidopsis* vasculature was carried out using thin transverse sections cut from JB4 resin embedded material as described previously (Pinon et al. 2008). Tissue was fixed in 3% glutaraldehyde or FAA, dehydrated through an ethanol series to 100% ethanol and embedded in JB4 resin (Agar Scientific). Embedded tissue was sectioned at 3 µm and subsequently stained with 0.02% Toluidine Blue. For hand cut sections, tissue was stained with either aqueous 0.02% Toluidine Blue or 0.05M Aniline blue in 100 mM Phosphate buffer, pH7.2.

Stems were analyzed at 8 weeks for *Arabidopsis*, 50 days for *Nicotiana* and four weeks after transfer to rooting medium for poplar.

Comparison of Cell Numbers in 35S::CLE41/42 Lines in *Arabidopsis*.

At the base of 6 week old inflorescence stems, lines over-expressing either CLE41 or CLE42 had, on average, more undifferentiated cells in vascular tissue (105.7 and 89.1, respectively) than those of wild type (58.6). When assaying cell numbers in vascular bundles from multiple insertion lines, both 35S::CLE41 and 35S::CLE42 plants had more vascular cells, although only in the case of 35S::CLE41 plants was this result statistically significant. There was no difference in the number of differentiated vascular cells in either 35S::CLE41 or 35S::CLE42 plants compared to the wild type (Table 1). We analysed progeny from two of the stronger transformed lines which were also used in subsequent genetic analysis. Stems from these lines had significantly more cells per vascular bundle (318.7 and 373.7 for 35S::CLE41 and 35S::CLE42, respectively) than wild type (273.7) clearly demonstrating that these genes are capable of increasing procambial cell divisions. In the case of 35S::CLE42 lines there was also a statistically significant increase in the number of differentiated cells.

Figure 5:
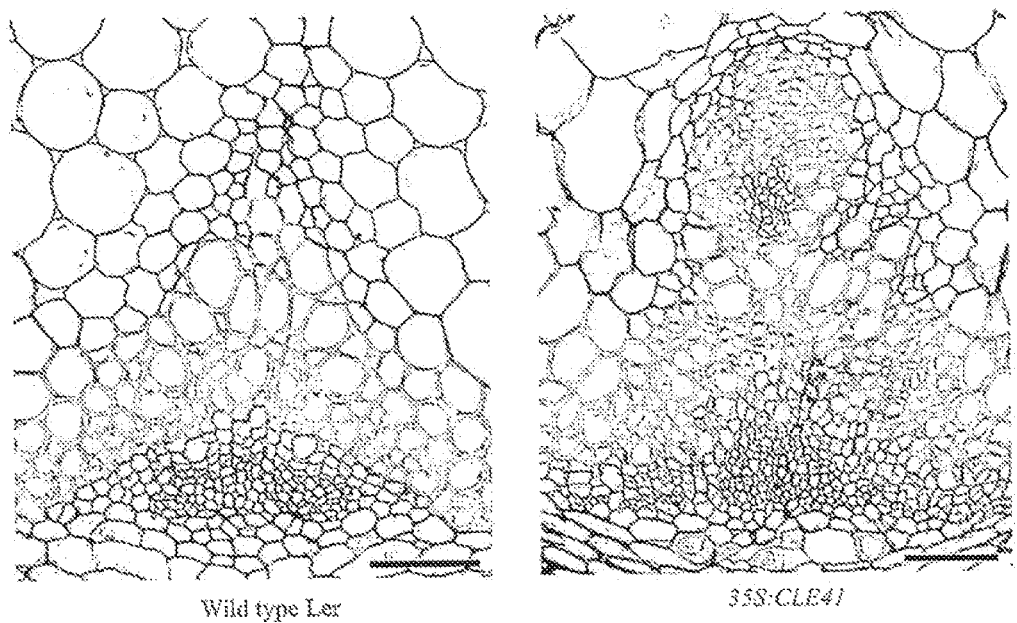
FIG. 5 shows the effect of over-expressing CLE41 on the stem vascular bundle of an *Arabidopsis* compared to the wild-type. Sections through stem vascular bundles of wild type, 35S::CLE41 and 35S::CLE42 from 50 day old plants. A large number of the extra cells in 35S::CLE41 plants (c.f.
Figure 6:
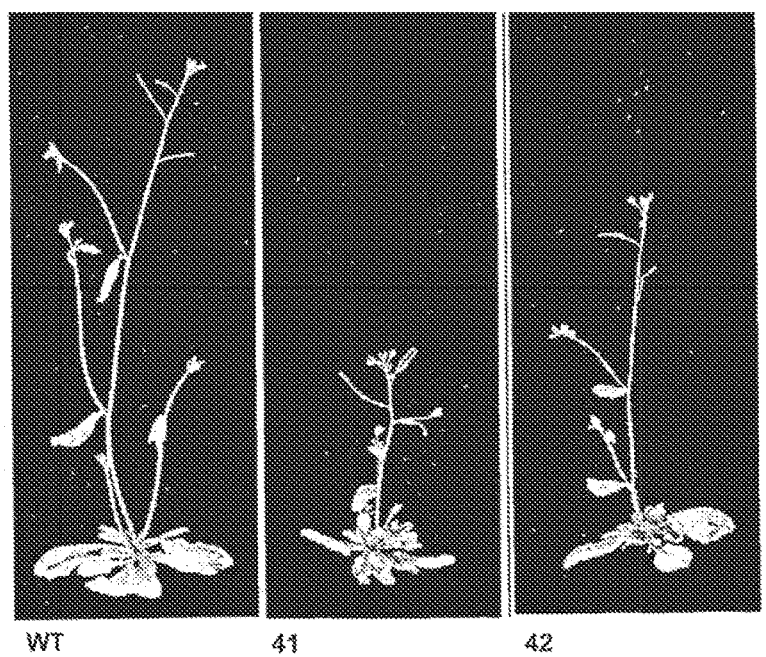
FIG. 6 shows the effects on plant stature of wild type compared to 35S::CLE41 and 35S::CLE42 in *Arabidopsis*.
Figure 7:
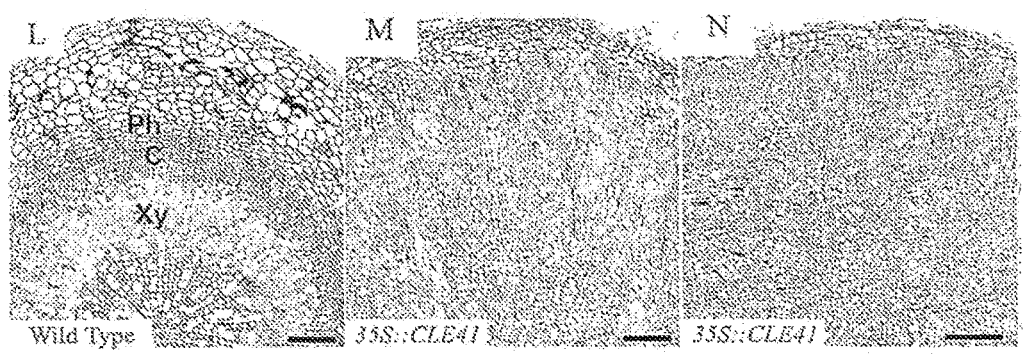
FIG. 7 shows the disrupted hypocotyl structure of a *Arabidopsis* plant where either CLE41 (M) or CLE42 (N) is over-expressed and compared with the wild type (L). In the transgenic lines (M, N), hypocotyls are much larger.

In order to determine whether these extra procambial cells would remain undifferentiated or would differentiate into xylem and phloem, we looked at the base of plant stems at senescence. In all genotypes the vast majority of vascular cells in the stem were fully differentiated (FIG. 5), including areas in 35S::CLE41/42 where large numbers of undifferentiated cells were present at earlier stages of development. Therefore, early on 35S::CLE41/42 plants have more undifferentiated cells but these ultimately become differentiated in inflorescence stems.

Mean vascular cell number from 19 independent transgenic lines.

|  | Col (n = 10) | 35S::CLE41 (n = 9) | 35S::CLE42 (n = 10) |
|---|---|---|---|
| Total Cells | 311.6 ± 15.6 | 373.2$^\varphi$ ± 24.3 | 341.8 ± 19.1 |
| Undifferentiated Cells | 58.6 ± 4.4 | 105.7* ± 9.8 | 89.0* ± 7.2 |
| Differentiated Cells (Xylem and Phloem) | 253 ± 12.6 | 267.5 ± 15.2 | 252.8 ± 14.4 |

*Significantly different from Col $P < 0.001$.
$^\varphi$Significantly different from Col $p < 0.05$.
± Standard error.

Figure 8:
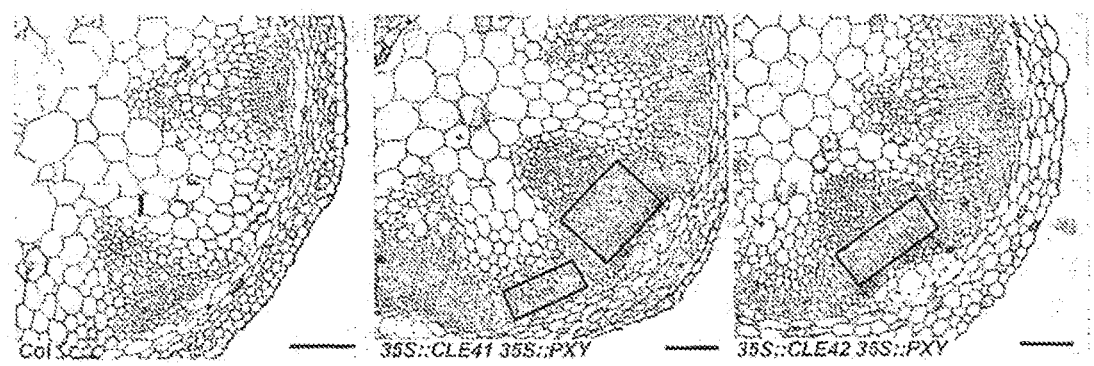
FIG. 8 shows the effect of over expressing both CLE41 and/or CLE42 and PXY on the structure and amount of cells in the vascular bundle and interfascicular region of stems from an *Arabidopsis thaliana* plant. Simultaneous over-expression of PXY and CLE41/42 gives increased in vascular cell number compared to plants over expressing CLE41/42 alone (c.f.
Figure 22:
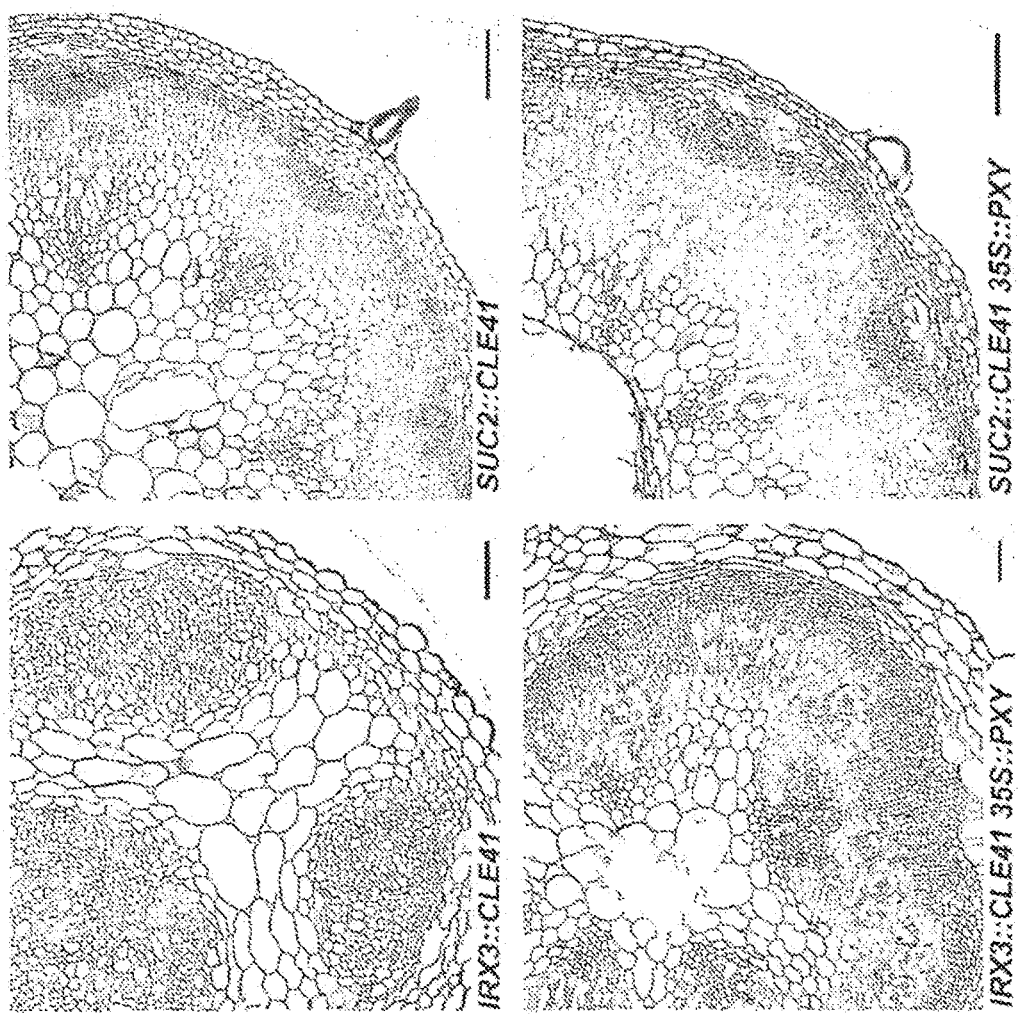
FIG. 22 shows the effect of phloem specific promoter SUC2 and xylem specific promoter IRX3 on cell organisation in *Arabidopsis*. IRX3::CLE41 plants have large vascular bundles. IRX3::CLE41 35S::PXY plants have large vascular bundles with large amounts of secondary growth (c.f.
Figure 23:
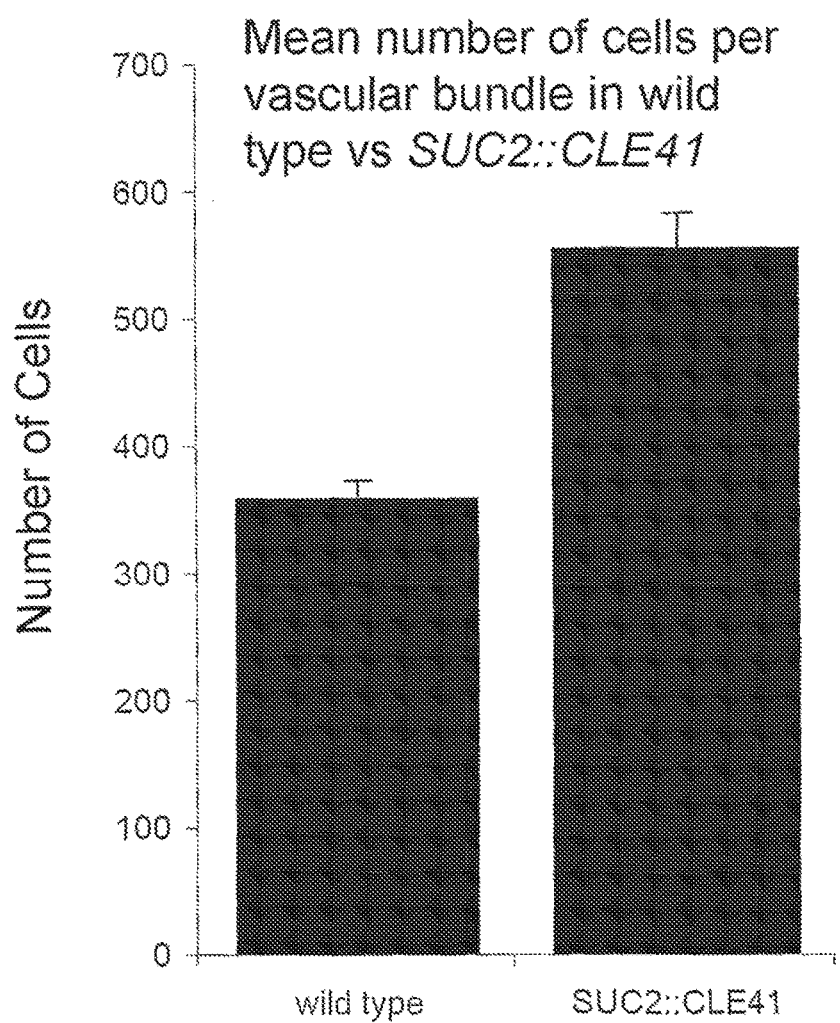
FIG. 23 is a graph showing the mean number of cells per vascular bundle. Expression of CLE41 in phloem cells under SUC2 gives more cells per vascular bundle in plants 6 week old *Arabidopsis* plants.
Figure 24:
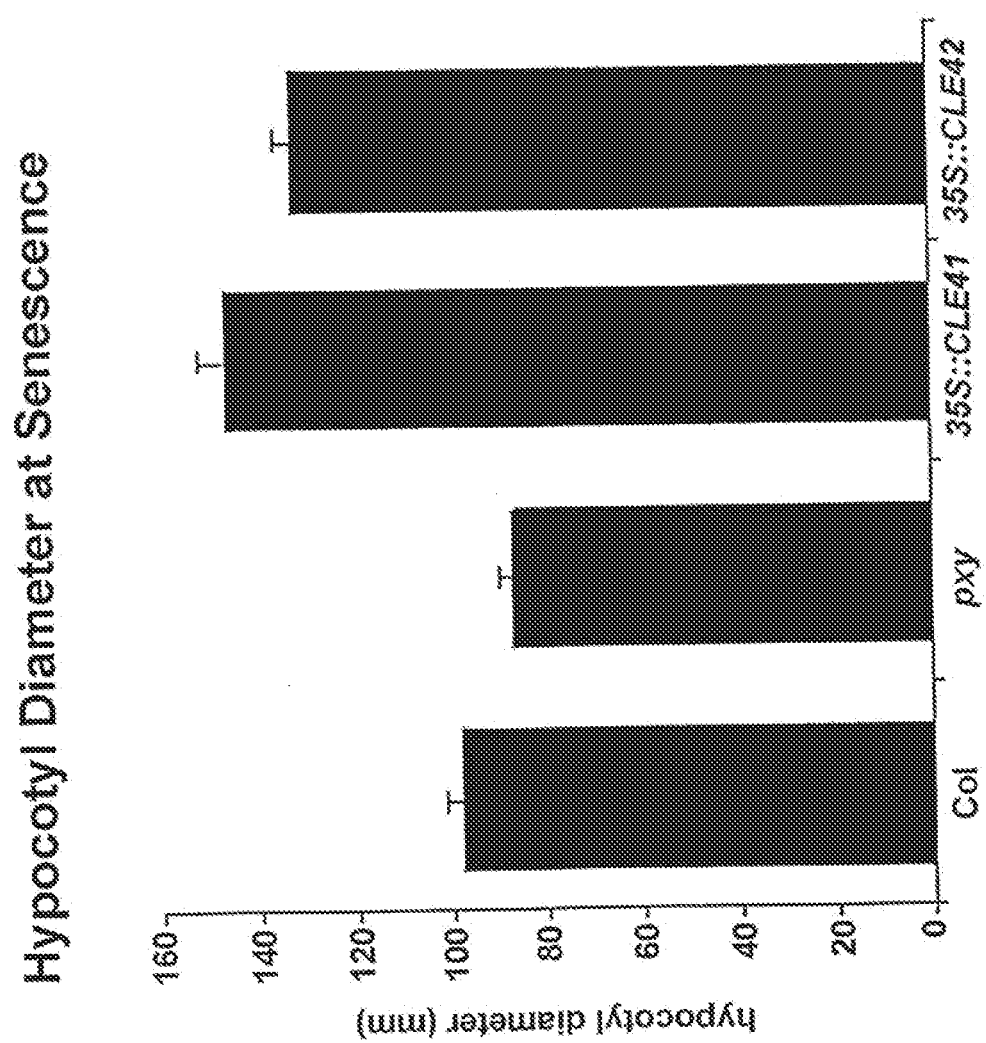
FIG. 24 is a graph showing the effect of over expression of CLE41 and CLE42 on hypocotyl diameter in *Arabidopsis*.
Figure 25:
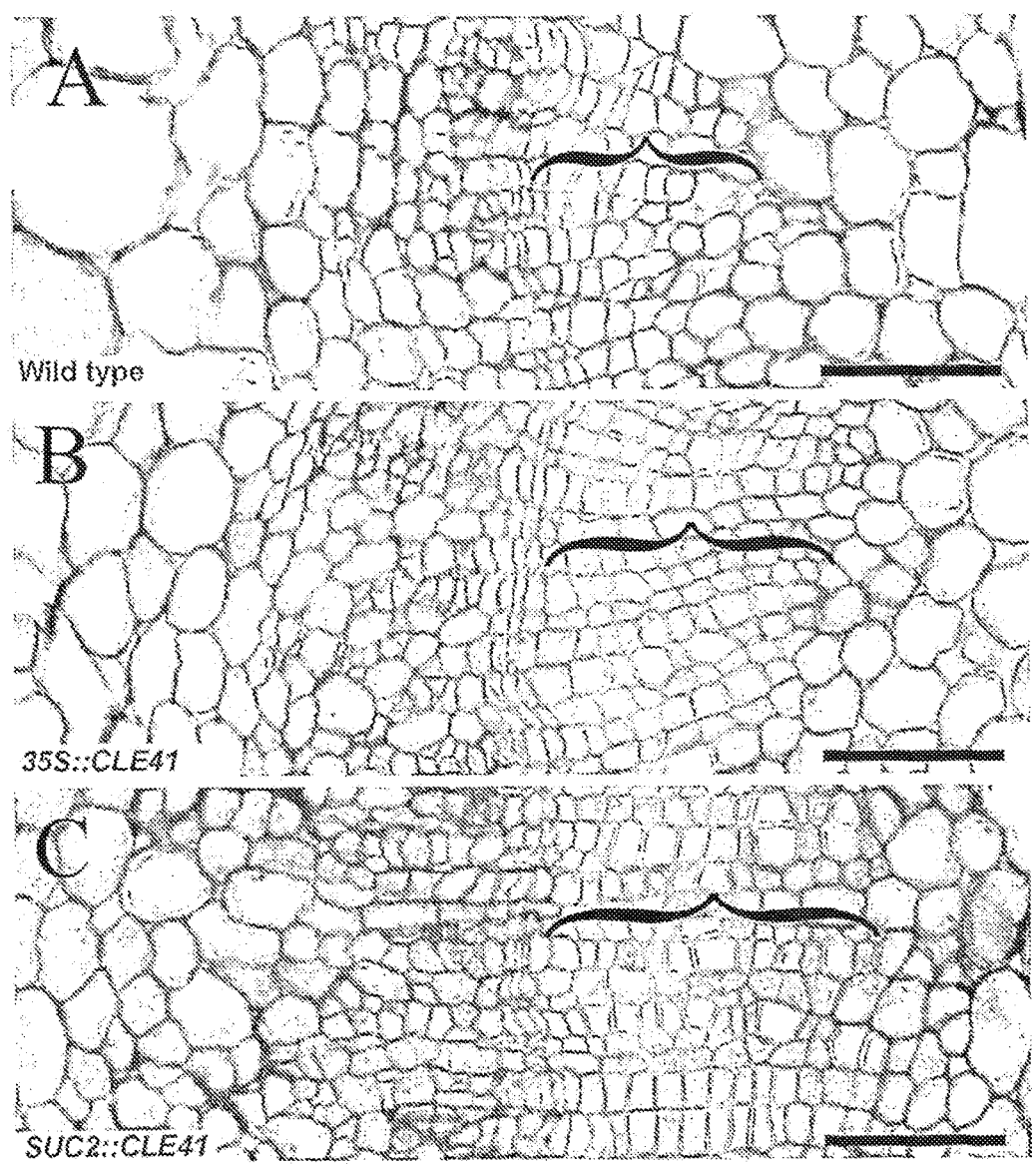
FIG. 25 shows the effect of over expression of CLE41 in poplar trees using the SUC2 or 35S promoters. The bracket denotes xylem cells, of which there are more in 35S::CLE41 and SUC2::CLE41 than wild type.

Over-Expression of CLE41 and CLE42 in Conjunction with PXY Further Enhances Effects on Secondary Growth We addressed the consequences of expressing PXY and CLE41 by using a 35S::PXY construct in a 35S::CLE41/42 background. The stems of 35S::CLE41/42 35S::PXY plants were characterised by dramatic increases in cell number in both the vascular bundle and in the interfascicular region such that a continuous ring of additional tissue within the stem. New cells were generated between the xylem and phloem in vascular bundles and also outside the interfascicular cells making the phenotype characteristic of dramatically increased secondary growth (FIG. 8). These results provide strong genetic evidence that CLE41/42 and PXY are sufficient for induction of vascular cell division within the procambium and elsewhere. Interestingly, the majority of increased cell divisions occurring when both CLE41/42 and PXY are over-expressed were relatively ordered, although aberrant cells divisions are still present. We made lines harbouring both IRX3::CLE41 and 35S::PXY constructs. We found that vascular organisation was disrupted in 35S::PXY IRX3::CLE41 plants (FIG. 25?), but increased secondary growth was also observed. 35S::PXY SUC2::CLE41 plants also demonstrated enhanced secondary growth (FIG. 22), but in contrast to 35S::PXY IRX3::CLE41, vascular tissue was highly ordered.

Figure 9:
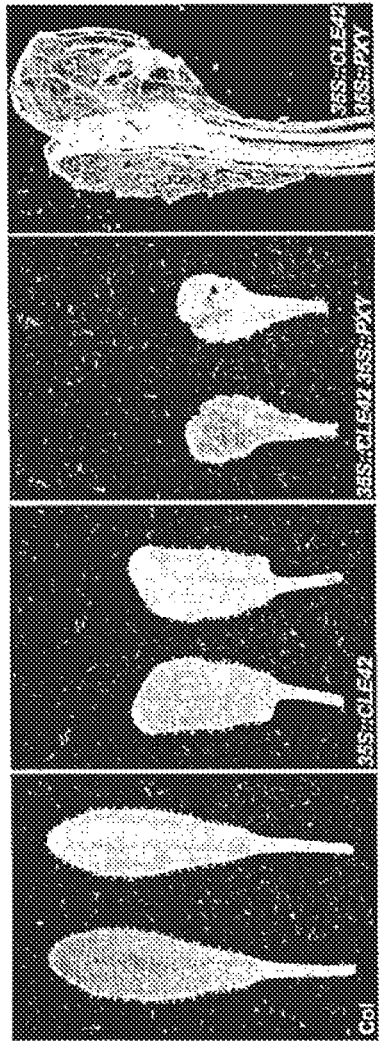
FIG. 9 shows the effect of over expression of both CLE41 and/or CLE42 and PXY on the leaf structure of an *Arabidopsis thaliana* plant. Multiple midveins in 35S::CLE42 35S::PXY plants demonstrate that expression of CLE42 and PXY can initiate vascular tissue.

An additional phenotype was observed in the leaves of 35S::CLE41/42 35S::PXY plants. In Col, 35S::CLE41/42 (FIG. 9) and 35S::PXY, leaves have a single midvein, however, in a minority of 35S::CLE42 35S::PXY plants the leaves appeared to exhibit increased vascular development. This additional vascular tissue develops together with the associated lamina suggesting development of ectopic vascular tissue.

Identification of CLE and PXY Homologues

Identification of *Populus Trichocarpa* CLE family was carried out by subjecting CLE41/42 to a WU-BLAST® algorithm search against green plant GB genomic (DNA) datasets using TBLASTN® algorithm: AA query to NTdb parameters on the TAIR website. All *Populus trichocarpa* hits (genomic region) with probability value (P) less than 1 were selected. These hits were subsequently on the *Populus* gene map ±1 kb from the WU-BLAST® algorithm hit region was then analyzed with the NCBI ORF finder and all coding regions containing similar 12 AA sequences to the output CLE sequence were examined. All putative proteins were aligned using the ClustalW algorithm using default settings.

The PXY homolog in *Oryza Sativa* was identified by locating PXY (At5g61480) in the homology tree from Shiu et al. (S.-H. Shiu et al., *Plant Cell* 16, 1220 (May 1, 2004, 2004)). The putative homolog was Osi056321.1 (*Oryza Sativa* Indica). This sequence was then subjected to a BLASTP® algorithm protein search against *O. sativa* (*japonica* cultivar-group) Non-RefSeq protein. The top hit was EAZ41508.1: hypothetical protein OsJ_024991 and was confirmed as being the PXY orthologue by performing a BLASTP® algorithm OsJ_024991 against Non-RefSeq protein database, *Arabidopsis Thaliana*, NCBI.

TABLE 2

| CLE | Representative | Synonyms | Organism | ID (representative seq) | Protein/Gene Annotation |
|---|---|---|---|---|---|
| 41 | AT_GEN_At3g24770.1 | CLE41 | *Arabidopsis thaliana* | AT_GEN_At3g24770.1 | At3g24770.1 68416.m03109 CLE41, putative CLAVATA/ESR-Related 41 (CLE41) |
|  |  |  |  | ATEST_TC255991_+1 | TC255991 |
|  |  |  |  | AT-TA_TA13011_3702_+1 | TA13011 3702 Putative CLE41 protein related cluster |
| 42 | ATEST_NP1098871_+1 | CLE42 | *Arabidopsis thaliana* | ATEST_NP1098871_+1 | NP1098871 putative CLAVATA3/ESR-related 42 precursor [*Arabidopsis thaliana*] |
| 44 | AT_GEN_At4g13195.1 | CLE44 | *Arabidopsis thaliana* | AT_GEN_At4g13195.1 | At4g13195.1 68417.m02052 expressed protein |
|  |  |  |  | ATEST_TC275167_+3 | TC275167 GB|AAO11557.1|27363276| BT002641 At4g13194/At4g13194 {*Arabidopsis thaliana;*}, complete |
| 51 | GMEST_TC171126_+3 |  | *Glycine max* | GMEST_TC171126_+3 | TC171126 similar to PIR|S61040|S61040 probable membrane protein YDL172c - yeast (*Saccharomyces cerevisiae*), partial (11%) |
|  |  |  |  | GM-TA_TA36215_3847_-3 | TA36215 3847 |
| 53 | GMEST_TC162846_+3 |  | *Glycine max* | GMEST_TC162846_+3 | TC162846 homologue to GP|21618281|gb|AAM67331.1 unknown {*Arabidopsis thaliana*}, partial (27%) |
|  |  |  |  | GMEST_TC162847_+1 | TC162847 homologue to GP|21618281|gb|AAM67331.1 unknown {*Arabidopsis thaliana*}, partial (19%) |
|  |  |  |  | GM-TA_BQ627547_-1 | BQ627547 Hypothetical protein CBG22664 related cluster |
|  |  |  |  | GM-TA_TA14900_3847_+1 | TA14900 3847 |
|  |  |  |  | GM-TA_TA8421_3847_+3 | TA8421 3847 SPBC215.13 protein related cluster |
| 60 | GMEST_BE658554_-3 |  | *Glycine max* | GMEST_BE658554_-3 | BE658554 homologue to PIR|H72173|H7217 D5L protein - *variola minor virus* (strain *Garcia*-1966), partial (23%) |
|  |  |  |  | GM-TA_BE658554_-3 | BE658554 |

TABLE 2-continued

| CLE | Representative | Synonyms | Organism | ID (representative seq) | Protein/Gene Annotation |
|---|---|---|---|---|---|
| 61 | GMEST_BM085374_+2 | | *Glycine max* | GMEST_BM085374_+2 | BM085374 homologue to GP|16945432|emb related to GLUCAN 1 3-BETA-GLUCOSIDASE PRECURSOR protein {*Neurospora crassa*}, partial (1%) |
| | | | | GM-TA_TA39380_3847_+1 | TA39380 3847 |
| 62 | GMEST_TC171467_+2 | | *Glycine max* | GMEST_TC171467_+2 | TC171467 |
| | | | | GM-TA_TA31733_3847_+2 | TA31733 3847 |
| 63 | GMEST_BU763224_+1 | | *Glycine max* | GMEST_BU763224_+1 | BU763224 similar to GP|21592472|gb|CLE gene family putative {*Arabidopsis thaliana*}, partial (15%) |
| | | | | GM-TA_BU763224_+1 | BU763224 |
| 64 | MT_GEN_IMGA|AC137080_19.1 | | *Medicago truncatula* | MT_GEN_IMGA|AC137080_19.1 | IMGA|AC137080_19.1 AC137080.13 104569-102347 E EGN_Mt041209 20041210 hypothetical protein |
| | | | | MT_GEN_IMGA|AC147499_5.1 | IMGA|AC147499_5.1 AC147499.5 26650-24428 E EGN_Mt041209 20041210 hypothetical protein |
| | | | | MTEST_BI311733_+1 | BI311733 |
| | | | | MT-TA_BI311733_+1 | BI311733 |
| 90 | OS_GEN_Os02g56490.1 | | *Oryza sativa* | OS_GEN_Os02g56490.1 | Os02g56490.1|11972.m33318| protein expressed protein |
| | | | | OSEST_TC278386_+3 | TC278386 *Oryza sativa* (*japonica* cultivar-group) cDNA clone: J033127D10, full insert sequence |
| | | | | OS-TA_TA21276_4530_+2 | TA21276 4530 Hypothetical protein OJ1520 C09.33 related cluster |
| 116 | PT_GEN_63277 | | *Populus trichocarpa* | PT_GEN_63277 fgenesh1_pg.C_LG_I000629 | jgi|Poptr1|63277| |
| 119 | PT_GEN_569594 | | *Populus trichocarpa* | PT_GEN_569594 | jgi|Poptr1|569594|eugene3.00120247 |
| 148 | ZMEST_DR801316_+1 | | *Zea mays* | ZMEST_DR801316_+1 | DR801316 |
| | | | | ZM-TA_DR801316_-1 | DR801316 Hypothetical protein P0617C02.125 related cluster |
| 149 | ZMEST_BM350390_-2 | | *Zea mays* | ZMEST_BM350390_-2 | BM350390 similar to UP|Q4NZF2 9DELT (Q4NZF2) PE-PGRS family protein, partial (4%) |
| | | | | ZM-TA_BM350390_+2 | BM350390 PE-PGRS family protein related cluster |
| 166 | STEST_TC114822_+3 | | *Solanum tuberosum* | STEST_TC114822_+3 | TC114822 TIGR Ath1|At4g13195.1 68417.m02052 expressed protein, partial (12%) |
| | | | | ST-TA_TA8910_4113_+3 | TA8910 4113 Hypothetical protein MTH423 related cluster |
| 167 | STEST_BF187584_+1 | | *Solanum tuberosum* | STEST_BF187584_+1 | BF187584 |
| | | | | ST-TA_TA17128_4113_+2 | TA17128 4113 Cluster related to UPI0000517AA3 |
| 168 | BN-TA_CX187708_+3 | | *Brassica napus* | BN-TA_CX187708_+3 | CX187708 F20P5.29 protein related cluster |

TABLE 2-continued

| CLE | Representative | Synonyms | Organism | ID (representative seq) | Protein/Gene Annotation |
|---|---|---|---|---|---|
| 169 | PV-TA_CV532906_+1 | | Phaseolus vulagaris | PV-TA_CV532906_+1 | CV532906 Hypothetical protein related cluster |
| 172 | STEST_TC129811_+3 | | Solanum tuberosum | STEST_TC129811_+3 | TC129811 similar to TIGR Ath1|At4g13195.1 68417.m02052 expressed protein, partial (12%) |
| | | | | ST-TA_TA11604_4113_+3 | TA11604 4113 Hypothetical protein related cluster |
| 173 | STEST_CV500295_+3 | | Solanum tuberosum | STEST_CV500295_+3 ST-TA_TA19709_4113_+3 | CV500295 TA19709 4113 Hypothetical protein related cluster |

*Nicotiana* Over Expressing CLE41/42 and PXY

In order to observe the phenotypic differences between the transgenic plants and wild type in *Nicotiana*, 35S::PXY, 35S::CLE41, 35S::CLE42 and wild type plants were grown in individual pots and places in the growth cabinet under same conditions. The height (from soil surface to the plant top in cM), hypocotyl width and stem width (diameter in mm) were measured when plants were 50 days old. The results of mean, standard error (SE), standard deviation (STD), minimum (Min) and maximum (Max) value were summarised in tables 3, 4, and 5. Single ANOVA between transgenic lines and wild type have been analysed and the P-value were given in the tables as well.

In table 3, the results show that the height of transgenic lines are highly significant difference between wild type (P<0.001****), the means of 35S::CLE41 and 35S::CLE42 are similar. 35S::CLE41 and 35S::CLE42 are also 20 cM and 12 cM shorter than wild type and 35S::PXY respectively. The results are consistent with the phenotypes being induced by over expression of CLE41 and CLE42.

TABLE 3

Height of Nicotiana at 50 days (cM)

| Name of plant | N | Mean | ±SE | STD | Min | Max | P-value |
|---|---|---|---|---|---|---|---|
| 35S::PXY | 10 | 26.70 | 1.10 | 3.49 | 18 | 30.5 | <0.001**** |
| 35S::CLE41 | 10 | 14.40 | 1.37 | 4.34 | 5.5 | 20 | <0.001**** |
| 35S::CLE42 | 8 | 15.98 | 3.32 | 9.38 | 6 | 29 | <0.001**** |
| Wild type | 10 | 35.35 | 1.20 | 3.79 | 27 | 39 | |

Table 4, shows that Hypocotyl width is not significantly different between 35S::PXY and wild type, however, there is a highly significant difference between 35S::CLE41 or 35S::CLE42 and Wild type (P<0.0001***). The means of 35S::CLE41 and 35S::CLE42 are about 2.3 mm thicker than wild type. The maximum hypocotyls width is 10.29 mm in 35S::CLE41 compared to 7.1 mm in wild type, there is a 3.19 mm difference, demonstrating that overexpression of CLE41 and CLE42 increases hypocotyl width.

TABLE 4

Hypocotyl width at 50 days (mm) (Nicotiana)

| Name of plant | N | Mean | ±SE | STD | Min | Max | P-value |
|---|---|---|---|---|---|---|---|
| 35S::PXY | 10 | 6.48 | 0.20 | 0.63 | 5.2 | 7.41 | >0.05 |
| 35S::CLE41 | 10 | 8.71 | 0.30 | 0.96 | 6.87 | 10.29 | <0.0001*** |
| 35S::CLE42 | 8 | 8.93 | 0.35 | 0.99 | 7.1 | 10.06 | <0.0001*** |
| Wild type | 10 | 6.34 | 0.14 | 0.45 | 5.3 | 7.1 | |

In table 5, the results show that there is no significant difference between 35S::PXY and wild type stem width, however, there is highly significant difference between 35S::CLE41 or 35S::CLE42 and Wild type (P<0.0001****). The maximum stem width is 8.62 mm in 35S::CLE41 compared with 5.92 mm in wild type, there is 2.7 mm different. The results shown that 35S::PXY did not affect the stem width, while the overexpression of CLE41 and CLE42 made the stem thicker than wild type.

TABLE 5

Stem width at 50 days (mm) (Nicotiana)

| Name of plant | N | Mean | ±SE | STD | Min | Max | P-Value |
|---|---|---|---|---|---|---|---|
| 35S::PXY | 10 | 5.23 | 0.22 | 0.68 | 4.3 | 6.67 | >0.05 |
| 35S::CLE41 | 10 | 7.06 | 0.33 | 1.03 | 5.24 | 8.62 | <0.001**** |
| 35S::CLE42 | 8 | 6.89 | 0.40 | 1.13 | 4.96 | 8.06 | <0.001**** |
| Wild type | 10 | 5.49 | 0.11 | 0.36 | 4.8 | 5.92 | |

In summary, over expression of PXY results in a significant change to the plant height compared to the wild type. However, over expression of CLE41 and CLE42 significantly alter the plants phenotype in terms of height, hypocotyl width and stem width.

2. *Nicotiana* Images

Figures 19, 20:
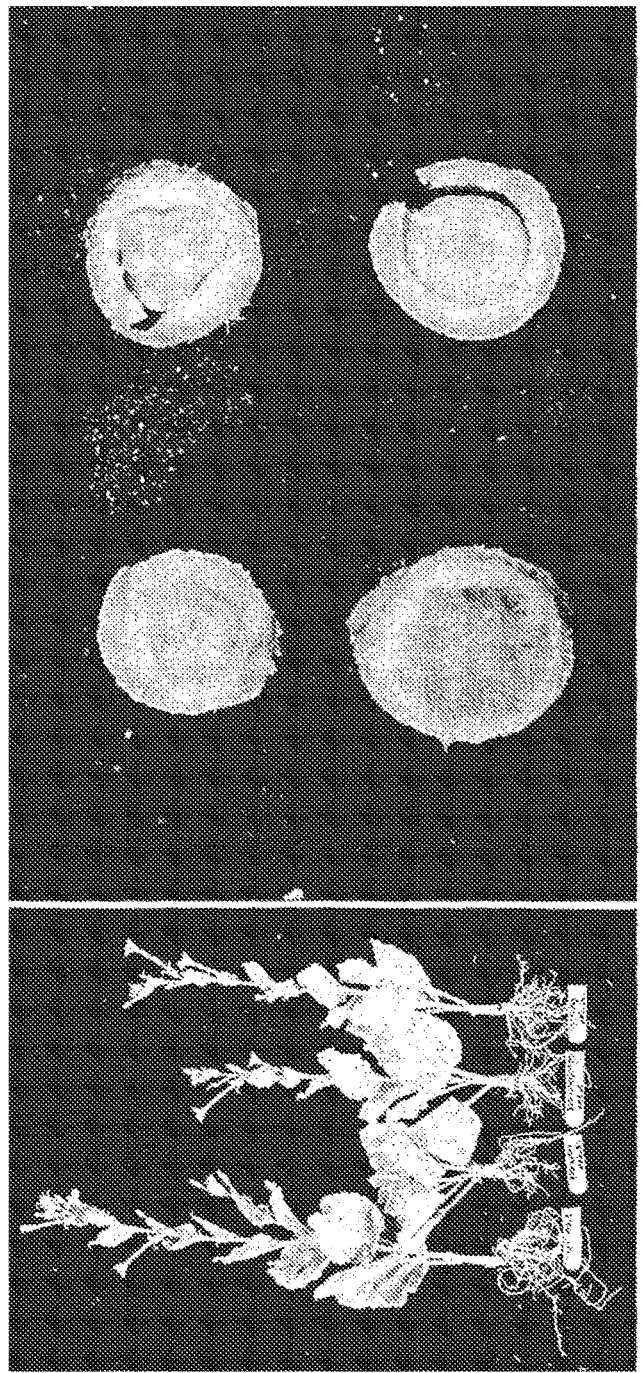
FIG. 19 the heights of *Nicotiana* plants which over express CLE41, PXY or both are shown. A height defect is associated with plants carrying the 35S::CLE41 construct. Normal plant height is restored when plants harbour both 35S::CLE41 and 35S::PXY cassettes.
FIG. 20 shows the cross section of the *Nicotiana* plants showing tissue structure and size. 35S::CLE41 35S::PXY plants have hypocotyls larger than wild type

In order to observe the phenotypic changes between the transgenic lines and wild type, the hypocotyl sections of transgenic lines 35S::PXY, 35S::CLE41, 35S::CLE42, 35S::CLE41 35S::PXY and wild type were cut when the plants were 50 days old. The images of whole plants and hypocotyl cross sections in FIGS. 19 and 20 illustrate the phenotypic differences between the lines. FIG. 19, shows that the over expression CLE41 results in a dwarf phenotype as documented in the table 4. The photographs demonstrate that this defect is much less when both CLE41 and PXY are over expressed.

In FIG. 20, cross sections of hypocotyls of plants demonstrates that plants over expressing PXY and CLE41 have thicker hypocotyls.

3. Histological Analysis of *Nicotiana* Hypocotyl Sections.

Figure 21:
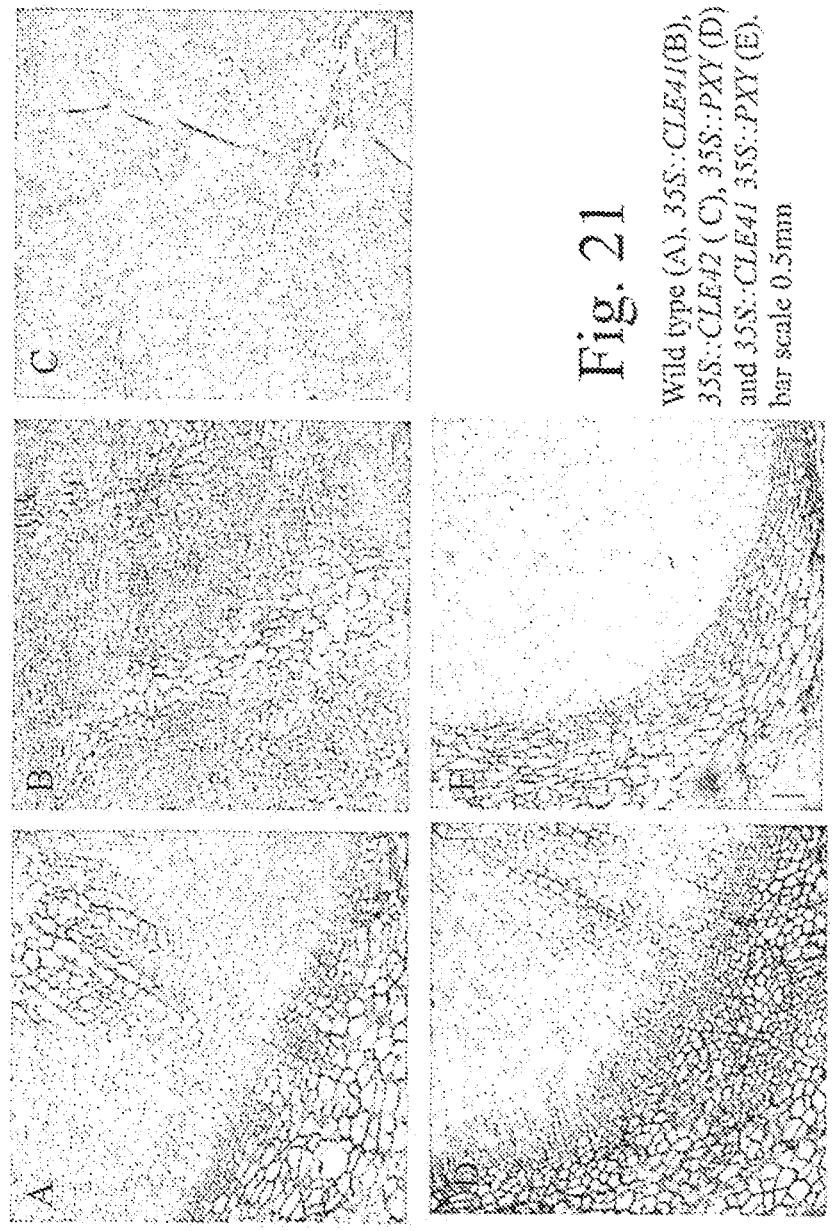
FIG. 21 shows cell organisation in *Nicotiana* plants in transverse section. 35S::CLE41 and 35S::CLE42 plants have more vascular tissue than wild type, but it is not ordered. 35S::CLE41 35S::PXY plants have ordered vasculature. Given that these plants have larger hypocotyls than wild type (see FIG. 20), and are of normal height (see FIG. 19), these plants clearly have more vascular tissue than wild type.

FIG. 21, wild type (A), 35S::CLE41 (B), 35S::CLE42 (C), 35S::PXY (D), 35S::CLE41 35S::PXY(E) Organisation is lost in plants over expressing CLE41/CLE42. Organisation is restored in plants over expressing both CLE41 and PXY.

A further experiment illustrates differences between single over expression of PXY, CLE41 and both PXY and CLE41. 10 plants of genotypes 35S::PXY, 35S::CLE41, 35S::CLE41 35S::PXY and wild type were planted in an individual pots and grown in a growth cabinet in identical conditions. The height (from soil surface to the plant top in cm), hypocotyl width and stem width (diameter in mm) were measured when plants were 42 days old. The results of mean, standard error (SE), standard deviation (STD), minimum (Min) and maximum (Max) value are presented in tables 6, 7, and 8. Single ANOVA between transgenic lines and wild type have been analysed and the P-value were given in the tables.

TABLE 6

Height at 42 days (cM)
Table 6. The height of 35S::CLE41 plants are significantly smaller than wild type ($P < 0.001$****), however, there is no difference between 35S::CLE41 35S::PXY and wild type in height.

| Name | N | Mean | SE | STD | Min | Max | P-value |
|---|---|---|---|---|---|---|---|
| 35S::CLE41 | 10 | 9.6 | 0.42 | 1.34 | 7 | 11.5 | $P < 0.0001$**** |
| 35S::PXY | 10 | 23.8 | 1.34 | 4.26 | 16 | 31.5 | $P < 0.01$** |
| 35S::CLE41 35S::PXY | 10 | 16.95 | 1.45 | 4.58 | 12 | 23 | $P > 0.05$ |
| Wild type | 10 | 19.12 | 0.62 | 1.98 | 16.5 | 22 | |

TABLE 7

Nicotiana Hypocotyls at 42 days (mm)
Table 7. Hypocotyl width was significantly larger in 35S::CLE41 and 35S::CLE41 35S::PXY compared to Wild type ($P < 0.0001$***).
The mean of 35S::CLE41 is about 2.4 mm thicker than wild type. The mean of 35S::CLE41 35S::PXY is 2.7 mm thicker than wild type.

| Name | N | Mean | SE | STD | Min | Max | P-value |
|---|---|---|---|---|---|---|---|
| 35S::CLE41 | 10 | 9.81 | 0.35 | 1.11 | 8.27 | 11.58 | $P < 0.0001$**** |
| 35S::PXY | 10 | 8.31 | 0.39 | 1.25 | 6.47 | 9.86 | $P > 0.05$ |
| 35S::CLE41 35S::PXY | 10 | 10.22 | 0.39 | 1.24 | 8.19 | 11.58 | $P < 0.0001$**** |
| Wild type | 10 | 7.45 | 0.27 | 0.87 | 5.99 | 8.87 | |

TABLE 8

Stem width at 42 days (mm)
Table 8. There is highly significant difference between 35S::CLE41 and 35S::CLE41 35S::PXY compared to wild type ($P < 0.0001$****). There is also a significant difference between 35S:PXY and Wild type. The maximum stem width is 9.43 mm in 35S::CLE41 compare 6.74 mm in wild type, a difference of 2.7 mm. The results demonstrate that overexpression of both CLE41 and PXY increase stem thickness compared to wild type.

| Name | N | Mean | SE | STD | Min | Max | P-value |
|---|---|---|---|---|---|---|---|
| 35S::CLE41 | 10 | 8.49 | 0.22 | 0.70 | 7.33 | 9.43 | $P < 0.0001$**** |
| 35S::PXY | 10 | 6.81 | 0.37 | 1.19 | 4.58 | 8.27 | $P < 0.05$* |
| 35S::CLE41 35S::PXY | 10 | 8.18 | 0.36 | 1.14 | 6.86 | 9.69 | $P < 0.0001$**** |
| Wild type | 10 | 5.88 | 0.16 | 0.53 | 5.14 | 6.74 | |

Poplar Harbouring 35S::CLE41 or SUC2::CLE41 Constructs Generate More Vascular Tissue than Wild Type.

Poplar transformed with 35S::CLE41 or SUC2::CLE41 were in JB4 sections were found to have more xylem tissue (see brackets in FIG. 25) demonstrating increases in vascular tissue.

The invention claimed is:

1. A method of manipulating the growth and/or structure of a plant, the method comprising modulating the level of Clavata3/Endosperm Surrounding Region (ESR)-related 41 (CLE41) in the plant, wherein the levels of CLE 41 are modulated by introducing into a cell of the plant:
I) a recombinant genetic construct comprising a nucleic acid molecule selected from the group consisting of:
i) a nucleic acid molecule that encodes a polypeptide comprising the amino acid sequence of amino acids 124 to 137 of the consensus sequence of SEQ ID NO:12 and a hydrophobic region at the amino terminus, and the nucleic acid molecule has at least 90% sequence identity to the nucleotide sequence of CLE 41 of SEQ ID NO:22, and;
ii) a nucleic acid molecule that hybridizes under stringent conditions of hybridization in 6x sodium chloride/sodium citrate at about 45° C. followed by one or more washes in 0.2xSSC 0.2% (w/v) SDS at 50° C. to the nucleotide sequence of Ii;
in combination with
II) a recombinant genetic construct comprising a nucleic acid molecule selected from the group consisting of:
i) a nucleic acid molecule that encodes a polypeptide comprising the consensus sequence of SEQ ID NO:20 and having at least 90% sequence identity to the nucleotide sequence of SEQ ID NO: 26 or SEQ ID NO: 27, and
ii) a nucleic acid molecule that hybridizes under stringent conditions of hybridization in 6x sodium chloride/sodium citrate at about 45° C. followed by one or more washes in 0.2xSSC 0.2% (w/v) SDS at 50° C. to the nucleotide sequence IIi), and
thereby manipulating the growth and/or structure of the plant.

2. The method according to claim 1, wherein the levels of CLE41 are upregulated.

3. A method of manipulating the growth and/or structure of a plant, the method comprising the steps of:
i) providing a cell manipulated to express:
1) a CLE41 polypeptide, in combination with a recombinant genetic construct according to claim 1 (II);
2) a polypeptide selected from the group consisting of:
a) a polypeptide comprising amino acids 124 to 137 of the consensus sequence of SEQ ID NO:12, a hydrophobic region at the amino terminus, and having at least 90% sequence identity to the amino acid sequence of CLE 41 of SEQ ID NO: 21, and
b) a polypeptide comprising the consensus sequence of SEQ ID NO:12, a hydrophobic region at the amino terminus, and encoded by a nucleic acid molecule having at least 90% sequence identity to the nucleotide sequence of CLE 41 of SEQ ID NO:22, in combination with a recombinant genetic construct according to claim 1 (II); or
3) a recombinant genetic construct according to claim 1 (I) in combination with a recombinant genetic construct according to claim 1 (II) or a polypeptide according selected from the group consisting of:
a) a polypeptide comprising the consensus sequence of SEQ ID NO:20 and having at least 90% sequence identity to the Phloem Intercalating with Xylem (PXY) sequence of SEQ ID NO:25, and
b) a polypeptide comprising the consensus sequence of SEQ ID NO:20 and encoded by a nucleic acid molecule that is at least 90% identical to the PXY nucleotide sequence of SEQ ID NO:26 or SEQ ID NO:27;
ii) regenerating said cell into a plant; and optionally
iii) monitoring the levels of CLE41 or a receptor thereof, and/or PXY in said regenerated plant, and
thereby manipulating the growth and/or structure of the plant.

4. A method of producing a plant-derived product, the method comprising:
  i) manipulating the growth and/or structure of a plant produced according to claim 1;
  ii) growing the plant until it reaches a pre-determined lateral size; and optionally
  iii) harvesting the plant-derived product produced by the plant.

5. A method of altering the mechanical properties of a plant or plant derived product, the method comprising:
  i) manipulating the growth and/or structure of a plant according to claim 1;
  ii) growing the plant until it reaches a pre-determined size; and optionally
  iii) harvesting a plant-derived product wherein the mechanical properties of the plant or the plant-derived product are altered.

\* \* \* \* \*